(12) United States Patent
Hung et al.

(10) Patent No.: US 7,723,104 B2
(45) Date of Patent: May 25, 2010

(54) CANCER SPECIFIC PROMOTERS

(75) Inventors: Mien-Chie Hung, Houston, TX (US);
Chi-Ping Day, Houston, TX (US);
Kun-Ming Rau, Houston, TX (US);
Xiaoming Xie, Houston, TX (US);
Zheng Li, Pearland, TX (US)

(73) Assignee: Board of Regents, The University Of Texas System, Austin, TX (US)

( * ) Notice: Subject to any disclaimer, the term of this patent is extended or adjusted under 35 U.S.C. 154(b) by 285 days.

(21) Appl. No.: 11/626,655

(22) Filed: Jan. 24, 2007

(65) Prior Publication Data

US 2008/0286860 A1 Nov. 20, 2008

Related U.S. Application Data

(62) Division of application No. 11/096,622, filed on Apr. 1, 2005.

(60) Provisional application No. 60/559,111, filed on Apr. 2, 2004.

(51) Int. Cl.
*C12N 15/63* (2006.01)
*C07H 21/04* (2006.01)
*C12N 15/85* (2006.01)

(52) U.S. Cl. .............. 435/320.1; 536/24.1; 435/325

(58) Field of Classification Search ............... 435/320.1
See application file for complete search history.

(56) References Cited

U.S. PATENT DOCUMENTS 6,638,762 B1 10/2003 Chang et al.

FOREIGN PATENT DOCUMENTS

| AU | 5742198 | 8/1998 |
|---|---|---|
| EP | 1009820 | 6/2000 |
| JP | 2001218587 | 8/2001 |
| WO | WO-98/33903 | 8/1998 |
| WO | WO-98/37207 | 8/1998 |
| WO | WO-99/16787 | 4/1999 |
| WO | WO-00/26343 | 5/2000 |
| WO | WO-02/40687 | 11/2001 |
| WO | WO-01/94600 | 12/2001 |
| WO | WO-03/074692 | 9/2003 |
| WO | WO-2004/089981 | 10/2004 |

OTHER PUBLICATIONS

Templeton N Vector Targeting for Therapeutic Gene Delivery, Edited by Curiel et al. published on Mar. 2003 by John Wiley & Sons, Inc. pp. 1-13.*
Xu et al. BBA 2003, vol. 1621, pp. 266-271.*
Segawa et al. Cancer Research 1998, vol. 58, pp. 2282-2287.*
Iyer et al. PNAS 2001 vol. 98, No. 25, pp. 14597-14600.*
Anderson et al., "Breast cancer-specific expression of the *Candida albicans* cytosine deaminase gene using a transcriptional targeting approach," *Cancer Gene Therapy*, 7(6): 845-852, 2000.

Bartke et al., "p53 upregulates cFLIP, inhibits transcription of NF-κB-regulated genes and induces caspase-8-independent cell death in DLD-1 cells," *Oncogene*, 2D: 571-580, 2001.
Bauman et al., "Differential Immunohistochemical Staining for DNA Topoisomerase II α and β in Human Tissues and for DNA Topoisomerase II β in Non-Hodgkin's Lymphomas," *Mod. Pathol.*, 10(3): 168-175, 1997.
Boyd et al., "Bik, a novel death-inducing protein shares a distinct sequence motif with Bcl-2 family proteins and interacts with viral and cellular survival-promoting proteins," *Oncogene*, 11: 1921-1928, 1995.
Casey et al., "Deletional analysis of the promoter region of the human transferrin receptor gene," *Nucleic Acids Research*, 16(2): 629-646, 1988.
Daniel, Peter T. et al. "Expression of the death gene bik/Nbk promotes sensitivity to drug-induced apoptosis in corticosteroid-resistant t-cell lymphoma and prevents tumor growth in severe combined immunodeficient mice," *Neoplasia*, 94(3): 1100-1107, 1999.
Donello et al., "Woodchuck Hepatitus Virus Contains a Tripartite Posttranscriptional Regulatory Element," *J. Virology*, 72(6): 5085-5092, 1998.
Elangovan et al., "Functional dissection of the pro-apoptotic protein bik: Heterodimerization with anti-apoptosis proteins is insufficient for induction of cell death," *J. Biol. Chem.*, 272(39): 24494-24498, 1997.
Friedman, Debbie, et al.; Ecteinascidin-743 inhibits activated but not constitutive transcription, Cancer Research, (Jun. 2002) vol. 62, pp. 3377-3381.
Fuernkranz et al., "Differential issue localization of oviduct and erythroid transferrin receptors," *Proc. Natl. Acad. Sci. USA*, 88:7505-7508, 1991.
Guillou et al., "Sertoli Cell-specific Expression of the Human Transferrin Gene: Comparison with the Liver-specific Expression," *J. Biol. Chem.*, 266(15): 9876-9884, 1991.
Han, Jeonghoon, et al.; Induction of apoptosis by human Nbk/Bik, a BH3-containing protein that interacts with E1B 19K, Molecular and Cellular Biology (Oct. 1996), pp. 5857-5864.
Hirsch et al., "Mitogenic activation of the transferrin receptor gene promoter I modulated by inhibitors of tyrosine kinases and tyrosine phosphatases," *Recept Signal Transduct.*, 6(3-4): 121-9, 1996.

(Continued)

*Primary Examiner*—Mondesi Robert
*Assistant Examiner*—Bao Qun Li
(74) *Attorney, Agent, or Firm*—Fulbright & Jaworski L.L.P.

(57) ABSTRACT

The present invention regards cancer-specific control sequences that direct expression of a polynucleotide encoding a therapeutic gene product for treatment of the cancer. Specifically, the invention encompasses breast cancer-, prostate cancer-, and pancreatic cancer-specific control sequences. Two breast cancer-specific sequences utilize specific regions of topoisomerase IIα and transferrin receptor promoters, particularly in combination with an enhancer. The prostate cancer-specific and pancreatic cancer-specific control sequences utilize composites of tissue-specific control sequences, a two-step transcription amplification sequence, and a post-transcriptional control sequence. In more particular embodiments, these polynucleotides are administered in combination with liposomes.

11 Claims, 28 Drawing Sheets

OTHER PUBLICATIONS

Hochhauser et al., "Cloning and characterization of the 5' flanking region of the human topoisomerase II alpha gene," *J. Biol. Chem.*, 267(26): 18961-5, 1992.

Idzerda et al., "Expression from the Transferrin Gene Promoter in Transgenic Mice," *Mol. Cell. Biol.*, 9(11): 5154-5162, 1989.

Isomura et al., "The Human Cytomegalovirus Major Immediate-Early Enhancer Determines the Efficiency of Immediate-Early Gene Transcription and Viral Replication in Permissive Cells at Low Multiplicity of Infection," *Journal of Virology*, 77(6): 3602-3614, 2003.

Iyer et al., "Two-step transcriptional amplification as a method for imaging reporter gene expression using weak promoters," *PNAS*, 98(25): 14595-14600, 2001.

Katabi et al., "Hexokinase Type II: A Novel Tumor-Specific Promoter for Gene-Targeted Therapy Differentially Expressed and Regulated in Human Cancer Cells," *Human Gene Therapy*, 10: 155-164, 1999.

Kawabata, "Regulation of expression of murine transferrin receptor 2," *Blood*, 98(6): 1949-1954, 2001.

Kugler et al., "Tissue-specificity of liver gene expression: a common liver-specific promoter element," *Nucleic Acids Research*, 16(8): 3165-3174, 1988.

Li et al., "Enhancement of *Bik* Antitumor Effect by *Bik* Mutants," *Cancer Res.*, 63: 7630-7633, 2003.

Lu et al., "Enhanced Gene Expression in Breast Cancer Cells in Vitro and Tumors in Vivo," *Molecular Therapy*, 6(6): 783-792, 2002.

Maeda et al., "A minimum c-erbB-2 promoter-mediated expression of herpes simplex virus thymidine kinase gene confers selective cytotoxicity of human breast cancer cells to ganciclovir," *Cancer Gene Therapy*, 8(11): 890-896, 2001.

Mendelzon et al., "The binding site for the liver-specific transcription factor Tf-LF1 and the TATA box of the human transferrin gene promoter are the only elements necessary to direct liver-specific transcription in vitro," *Nucleic Acids Research*, 18(19): 5717-5721, 1990.

Mo et al., "Overexpression of human DNA topoisomerase II alpha by fusion to enhanced green fluorescent protein," *Biotechn.*, 25(6): 1052-7, 1998.

Panaretakis, Theocharis, et al.; Activation of bak, bax, and BH3-only proteins in the apoptotic response to doxorubicin, Journal of Bio. Chem. (Nov. 2002), vol. 277, No. 46, pp. 44317-44326.

Qiao et al., "Tumor-specific transcriptional targeting of suicide gene therapy," *Gene Therapy*, 9: 168-175, 2002.

Radetzki et al., "The apoptosis promoting Bcl-2 homologues Bak and Nbk/Bik overcome drug resistance in Mdr-1-negative and Mdr-1-overexpressing breast cancer cell lines," *Oncogene*, 21(2): 227-38, 2002.

Sandford et al., "Rat Cytomegalovirus Major Immediate-Early Enhancer Switching Results in Altered Growth Characteristics," *Journal of Virology*, 75(11): 5076-5083, 2001.

Sato et al., "Optimization of adenoviral vectors to direct highly amplified prostate-specific expression for imaging and gene therapy," *Mol. Ther.*, 8(5): 726-37, 2003.

Shindelman et al., "Demonstration of the Transferrin Receptor in human breast cancer tissue. Potential marker for identifying dividing cells," *Int. J. Cancer*, 27:329-334, 1981.

Shterman et al., "Comparison of Transferrin Receptors, Iron Content and Isoferritin profile in normal and malignant human breast cell lines," *Pathobiol.*, 59: 19-25, 1991.

Theisen et al., "A C/EBP-Binding Site in the Transferring Promoter is Essential for Expression in the Liver but Not the Brain of Transgenic Mice," *Mol. Cell. Biol.*, 13(12): 7666-7676, 1993.

Tong et al., "The Pro-apoptotic Protein, Bik, Exhibits Potent Antitumor Activity That Is Dependent on Its BH3 Domain," *Molecular Cancer Therapeutics*, 1: 95-102, 2001.

Verma et al., "Phosphorylation of the Pro-apoptotic Protein BIK," *J. Biol. Chem.*, 276(7): 4671-4676, 2001.

Verma et al., "Structural analysis of the human pro-apoptotic gene *Bik*: Chromosomal localization, genomic organization and localization of promoter sequences," *Gene*, 254(1-2): 157-162, 2000.

Xie et al., "Adenovirus-mediated tissue-targeted expression of a caspase-9-based artificial death switch for the treatment of prostate cancer," *Cancer Res.*, 61(18): 6795-804, 2001.

Zakin, "Regulation of transferrin gene expression," *The FASEB Journal*, 6:3253-3258, 1992.

Zhang et al., "A Gene-Specific Promoter in Transgenic Mice Directs Testis-Specific Demethylation Prior to Transcriptional Activation in Vivo," *Biology of Reproduction*, 59: 284-292, 1998.

Zhang et al., "A small composite probasin promoter confers high levels of prostate-specific gene expression through regulation by androgens and glucocorticoids in vitro and in vivo," *Endocrinology*, 141(12): 4698-710, 2000.

Zhang et al., "Molecular engineering of a two-step transcription amplification (TSTA) system for transgene delivery in prostate cancer," *Mol. Ther.*, 5(3): 223-32, 2002.

Zou, Yiyu, et al., "Systemtic tumor suppression by the proapoptotic gene bik,"*Cancer Research* , 62: 8-12, 2002.

Xie et al., "Targeted Expression of BikDD Eradicates Pancreatic Tumors in Noninvasive Imaging Models"; pp. 52-65; Cell Press; Cancer Cell Article 12, Jul. 2007.

* cited by examiner

A

B

A

B

C

SEQUENCE LISTING

<160> NUMBER OF SEQ ID NOS: 24

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence:
    Synthetic Primer

<400> SEQUENCE: 1
aggacccagg tacctatgtt caaaagtgcc tc                                    32

<210> SEQ ID NO 2

```
<211> LENGTH: 28
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 2
ccttgcctgc tgctttccac caagtgct                                           28

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 3
caggttggga aaatggtcag ccctcctgaa a                                       31

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 4
cgttctgagg cgggcaatca aatgacctat                                         30

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 5
cccgctagcc taattttatt ttattttaa ttc                                      33

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 6
cccctcgagg tattttggaa aaatgtcctt atctag                                  36

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 7
cgcacgcgta ggcatcagct ctctacaatt c                                       31

<210> SEQ ID NO 8
<211> LENGTH: 32
```

```
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 8
agcctcgagc aggatctgag ataagaacca cg                                    32

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 9
acggcgctcg agtccatcag ttctcatc                                         28

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 10
ttacttaagc ttgtgtagga cgcctgtc                                         28

<210> SEQ ID NO 11
<211> LENGTH: 452
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 11
tacgggccag atatacgcgt tgacattgat tattgactag ttattaatag taatcaatta      60
cggggtcatt agttcatagc ccatatatgg agttccgcgt tacataactt acggtaaatg    120
gcccgcctgg ctgaccgccc aacgaccccc gcccattgac gtcaataatg acgtatgttc    180
ccatagtaac gccaataggg actttccatt gacgtcaatg ggtggagtat ttacggtaaa    240
ctgcccactt ggcagtacat caagtgtatc atatgccaag tacgccccct attgacgtca    300
atgacggtaa atggcccgcc tggcattatg cccagtacat gaccttatgg actttcctta    360
cttggcagta catctacgta ttagtcatcg ctattaccat ggtgatgcgg ttttggcagt    420
acatcaatgg gcgtggatag cggtttgact ca                                   452

<210> SEQ ID NO 12
<211> LENGTH: 180
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 12
agacggtgag agcgagtcag ggattggctg gtctgcttcg ggcgggctaa aggaaggttc      60
aagtggagct ctcctaaccg acgcgcgtct gtggagaagc ggcttggtcg ggggtggtct    120
cgtggggtcc tgcctgttta gtcgctttca gggttcttga gccccttcac gaccgtcacc    180
```

<210> SEQ ID NO 13
<211> LENGTH: 231
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 13

```
cggccgccag tgtgatggat atctgcagaa ttcgcccttg cgatctgtca gagcacctcg      60
cgagcgtacg tgcctcagga agtgacgcac agccccctg ggggccgggg gcggggccag     120
gctataaacc gccggttagg ggccgccatc ccctcagagc gtcgggatat cgggtgaagg    180
gcgaattcca gcacactggc ggccgttact agtggatccg agctcggtac c             231
```

<210> SEQ ID NO 14
<211> LENGTH: 1757
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 14

```
ccttgcctgc tgctttccac caagtgctgg agagctggtg aattgctcac tcccggctca      60
ttcctctaat gaccgaagcg tctcgcagat gcaacctgcc gtggaggagc agggagggag    120
tgatttccag gtgtgggctt tttcagccat tcctaaaggc gacttgagtt cacctcactc    180
actccagcat ttgtactcct gttgtggaaa aggcagtgag cacaagccaa gcccgctcca    240
ccttcacccc gccccacctc ccccggccct ttcctgggcc agtcttaggg ccctgagtac    300
agacagcctg gctacccgtt aaccattctc agcgtgtggc tgcttttac acacatgtgt    360
acatatgcac ggacacacac acacacacag aggcttcccc agtactcctc tatataggaa    420
cccgtcacca tcccagacat atgcagaaga aagcccaaac cggctgtgtg agacaggaac    480
aattaacacg gtaacagatc cgataatgca gaccatcagg cctaaagaac acggagggac    540
tgtgttctac ctccttatag aaaagcaatt agtgcctttt tagctttgga accatgcccg    600
gtggtgtgtg tgtggacaga actgctggct ggttgttaag ttgctactaa acacagtgtt    660
gtttctcgtg gtctctgccc ttgttaacta ggattgaggc acttttgaac ataggtacct    720
gggtcctaag ggcgaattcc agcacactgg cggccgttac tagtggatcc gagctcggta    780
ccaagctcca gctgggaata gagataggag gggacccagc tggatgcagt gggcagtggg    840
ggtcatagag tcaagagggt acagaataca atggggtcct agtatcatgg tggaggtcag    900
aaagagccct aaaagagagg gtcaaggtag gaggttagtg aaggtccacc tccaccctct    960
ccaggacagg gacatcaggc cacaattaat ttctctgcag ttggtgagtg gtcatggtct    1020
ctggagtccc cagcatccag agtgtccctg gtctagtggt ccccccttc tgagccacag    1080
ccactttctc catcaaatga ggccagtaat acccatccca tagtgatgct gtgaggatga    1140
gatgagcatc tgtaagtgct gaagataatc cctgacacat cccaagcatt cagcagtgca    1200
agcatacact tacacggcac tccccagagc caggcatgtg ctggtgcctc atacacgtga    1260
ccacatttga tcgtcacaat gaccctgtga gggagactgt gcaacagagg actgaccttg    1320
ctcaaagacc tcaggcgttt ccctcgagag cctgagaggt catctctttt tttttttttt    1380
tttcctttct ttcttttct tttccatttc ttttctttg caagaggtca tctctaatgc    1440
```

-continued

```
tttggaatat cctgccagat tagagtccct ttgttcacct gaaggtttgg gccacaccag    1500
atagtctaac ggtgtgattt gtgctgaagg ttttgagcca cactatatca gctagatttc    1560
tagagcggcc ggccgcaata aaatatcttt attttcatta catctgtgtg ttggttttttt   1620 gtgtgaatcg atagtactaa catacgctct ccatcaaaac aaaacgaaac aaaacaaact    1680
agcaaaatag gctgtcccca gtgcaagtgc aggtgccaga acatttctct atcgataggt    1740
accgagctca tttaggt                                                    1757

<210> SEQ ID NO 15
<211> LENGTH: 646
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 15
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga ctttcgcttt ccccctccct   300
attgccacgg cggaactcat cgccgcctgc cttgcccgct gctggacagg gctcggctg    360 ttgggcactg acaattccgt ggtgttgtcg gggaagctga cgtcctttcc atggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc tggaattcga   600
gctcggtacg ggctcgacta gagtcggggc ggccggccgc ttcgag                   646

<210> SEQ ID NO 16
<211> LENGTH: 819
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 16
ttatgtcaca ccacagaagt aaggttcctt cacaaagatc ccaagctgtc gatcgacatt     60
tctagaggat ctcggacccg gggaatcccc gtcccccaac atgtccagat cgaaatcgtc    120
tagcgcgtcg gcatgcgcca tcgccacgtc ctcgccgtca agtgcagct cgtcccccag     180 gctgacatcg gtcgggggg cggatctcgg acccggggaa tcccgtccc caacatgtc      240 cagatcgaaa tcgtctagcg cgtcggcatg cgccatcgcc acgtcctcgc cgtctaagtg   300
gagctcgtcc cccaggctga catcggtcgg ggggcggat ccccgggct gcaggaattc     360 cggcgataca gtcaactgtc tttgaccttt gttactactc tcttccgatg atgatgtcgc    420
acttattcta tgctgtctca atgttagagg catatcagtc tccactgaag ccaatctatc    480
tgtgacggca tctttattca cattatcttg tacaaataat cctgttaaca atgctttat    540 atcctgtaaa gaatccattt tcaaaatcat gtcaaggtct tctcgaggaa aaatcagtag    600
aaatagctgt tccagtcttt ctagccttga ttccacttct gtcagatgtg ccctagtcag    660
cggagacctt ttggttttgg gagagtagcg acactcccag ttgttcttca gacacttggc    720
```

```
gcacttcggt ttttctttgg agcacttgag cttttttaagt cggcaaatat cgcatgcttg    780
ttcgatagaa gacagtagct tcatctttca ggaggctag                            819

<210> SEQ ID NO 17
<211> LENGTH: 1352
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 17
acagacattg acattgtgtc atctagtata caaataggtt cttggagtac tttactaggc     60
atggacaatg cccaatgcct gtcccattct tcaggcatat tttttatttgt gggctttatg   120 tccctattaa gaaaaagact aagaacaaga tgctatcata ttttcttaac tggaatggta   180
gatgtttaaa catgatgact accaagcttg gctagaacat tgtgtcatct agtatacaaa   240
taggttcttg gagtacttta ctaggcatgg acaatgccca atgcctgtcc cattcttcag   300
gcatattttt atttgtgggc tttatgtccc tattaagaaa aagactaaga acaagatgct   360
atcataagct ccaagcttat cgccagctgg gaatagagat aggaggggac ccagctggat   420
gcagtgggca gtggggtca tagagtcaag agggtacaga atacaatggg gtcctagtat   480
catggtggag gtcagaaaga gccctaaaag agagggtcaa ggtaggaggt tagtgaaggt   540
ccacctccac cctctccagg acagggacat caggccacaa ttaatttctc tgcagttggt   600
gagtggtcat ggtctctgga gtccccagca tccagagtgt ccctggtcta gtggtccccc   660
ctttctgagc cacagccact ttctccatca aatgaggcca gtaatacccca tcccatagtg   720 atgctgtgag gatgagatga gcatctgtaa gtgctgaaga taatccctga cacatcccaa   780
gcattcagca gtgcaagcat acacttacac ggcactcccc agagccaggc atgtgctggt   840
gcctcataca cgtgaccaca tttgatcgtc acaatgaccc tgtgagggag actgtgcaac   900
agaggactga ccttgctcaa agacctcagg cgtttcccct cagagcctga gaggtcatct   960 ctttttttt ttttttttcc tttctttctt tttcttttcc atttcttttt ctttgcaaga  1020
ggtcatctct aatgctttgg aatatcctgc cagattagag tccctttgtt cacctgaagg  1080
tttgggccac accagatagt ctaacggtgt gatttgtgct gaaggtttgg agccacacta  1140
tatcagctag atttctagag cggccggccg caataaaata tctttatttt cattacatct  1200
gtgtgttggt tttttgtgtg aatcgatagt actaacatac gctctccatc aaaacaaaac  1260
gaaacaaaac aaactagcaa aataggctgt ccccagtgca agtgcaggtg ccagaacatt  1320
tctctatcga taggtaccga gctcatttag gt                                 1352

<210> SEQ ID NO 18
<211> LENGTH: 496
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 18
ggccgcccca cgtgcgcagc aggacgcagc gctgcctgaa actcgcgccg cgaggagagg    60
gcggggccgc ggaaaggaaa gggggggct gggaggcccg gagggggctg gccggggac    120 ccgggagggg tcgggacggg gcggggtccg cgcggaggag gcggagctgg aaggtgaagg   180
```

-continued

| | |
|---|---|
| ggcaggacgg gtgcccgggt ccccagtccc tccgccacgt ggggagcgcg gtcctgggcg | 240 |
| tctgtgcccg cgaatccact gggagcccgg cctggccccg acagcgcagc tgctccgggc | 300 |
| ggacccgggg gtctgggccg cgcttccccg cccgcgcgcc gctcgcgctc ccagggtgca | 360 |
| gggacgccag cgagggcccc agcggagaga ggtcgaatcg gcctaggctg tggggtaacc | 420 |
| cgagggaggg gcctctagat ataagggcga attccagcac actggcggcc gttactagtg | 480 |
| gatccgagct cggtac | 496 |

<210> SEQ ID NO 19
<211> LENGTH: 857
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 19

| | |
|---|---|
| ttatgtcaca ccacagaagt aaggttcctt cacaaagatc ccaagctgtc gatcgacatt | 60 |
| tctagaggat ctcggacccg ggaatcccc gtcccccaac atgtccagat cgaaatcgtc | 120 |
| tagcgcgtcg gcatgcgcca tcgccacgtc ctcgccgtct aagtggagct cgtcccccag | 180 |
| gctgacatcg gtcgggggg cggatctcgg acccggggaa tccccgtccc caacatgtc | 240 |
| cagatcgaaa tcgtctagcg cgtcggcatg cgccatcgcc acgtcctcgc cgtctaagtg | 300 |
| gagctcgtcc cccaggctga catcggtcgg ggggcggat ccccgggct gcaggaattc | 360 |
| cggcgataca gtcaactgtc tttgaccttt gttactactc tcttccgatg atgatgtcgc | 420 |
| acttattcta tgctgtctca atgttagagg catatcagtc tccactgaag ccaatctatc | 480 |
| tgtgacggca tctttattca cattatcttg tacaaataat cctgttaaca atgcttttat | 540 |
| atcctgtaaa gaatccattt tcaaaatcat gtcaaggtct tctcgaggaa aaatcagtag | 600 |
| aaatagctgt tccagtcttt ctagccttga ttccacttct gtcagatgtg ccctagtcag | 660 |
| cggagacctt ttggttttgg gagagtagcg acactcccag ttgttcttca gacacttggc | 720 |
| gcacttcggt ttttctttgg agcacttgag ctttttaagt cggcaaatat cgcatgcttg | 780 |
| ttcgatagaa gacagtagct tcatctttca ggaggctagg gccgccagtg tgatggatat | 840 |
| ctgcagaatt cgcccctt | 857 |

<210> SEQ ID NO 20
<211> LENGTH: 8512
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 20

| | |
|---|---|
| ggtacgggag gtacttggag cggccgcgat ccagacatga taagatacat tgatgagttt | 60 |
| ggacaaacca caactagaat gcagtgaaaa aaatgcttta tttgtgaaat ttgtgatgct | 120 |
| attgctttat ttgtaaccat tataagctgc aataaacaag ttaacaacaa caattgcatt | 180 |
| cattttatgt ttcaggttca gggggaggtg tgggaggttt tttaaagcaa gtaaaacctc | 240 |
| tacaaatgtg gtatggctga ttatgatcat gaacagactg tgaggactga ggggcctgaa | 300 |
| atgagccttg ggactgtgaa tttaaaatac acaaacaatt agaatcagta gtttaacaca | 360 |
| ttatacactt aaaaattta tatttacctt agagctttaa atctctgtag gtagtttgtc | 420 |
| caattatgtc acaccacaga agtaaggttc cttcacaaag atcccaagct gtcgatcgac | 480 |

-continued

```
atttctagag gatctcggac ccggggaatc cccgtccccc aacatgtcca gatcgaaatc    540
gtctagcgcg tcggcatgcg ccatcgccac gtcctcgccg tctaagtgga gctcgtcccc    600
caggctgaca tcgtcgggg gggcggatct cggacccggg gaatcccgt ccccaacat    660
gtccagatcg aaatcgtcta gcgcgtcggc atgcgccatc gccacgtcct cgccgtctaa    720
gtggagctct cccccaggc tgacatcggt cggggggcg gatccccgg gctgcaggaa    780
ttccggcgat acagtcaact gtctttgacc tttgttacta ctctcttccg atgatgatgt    840
cgcacttatt ctatgctgtc tcaatgttag aggcatatca gtctccactg aagccaatct    900
atctgtgacg gcatctttat tcacattatc ttgtacaaat aatcctgtta acaatgcttt    960
tatatcctgt aaagaatcca ttttcaaaat catgtcaagg tcttctcgag gaaaaatcag   1020
tagaaatagc tgttccagtc tttctagcct tgattccact tctgtcagat gtgccctagt   1080
cagcggagac cttttggttt tgggagagta gcgacactcc cagttgttct tcagacactt   1140
ggcgcacttc ggttttctt tggagcactt gagcttttta agtcggcaaa tatcgcatgc   1200
ttgttcgata aagacagta gcttcatctt tcaggaggct agggccgcca gtgtgatgga   1260
tatctgcaga attcgccctt ccttgcctgc tgctttccac caagtgctgg agagctggtg   1320
aattgctcac tcccggctca ttcctctaat gaccgaagcg tctcgcagat gcaacctgcc   1380
gtggaggagc agggagggag tgatttccag gtgtgggctt tttcagccat tcctaaaggc   1440
gacttgagtt cacctcactc actccagcat ttgtactcct gttgtggaaa aggcagtgag   1500
cacaagccaa gcccgctcca ccttcacccc gccccacctc cccgccct ttcctgggcc   1560
agtcttaggg ccctgagtac agacagcctg gctacccgtt aaccattctc agcgtgtggc   1620
tgcttttac acacatgtgt acatatgcac ggacacacac acacacacag aggcttcccc   1680
agtactcctc tatataggaa cccgtcacca tcccagacat atgcagaaga aagcccaaac   1740
cggctgtgtg agacaggaac aattaacacg gtaacagatc cgataatgca gaccatcagg   1800
cctaaagaac acggagggac tgtgttctac ctccttatag aaaagcaatt agtgcctttt   1860
tagctttgga accatgcccg gtggtgtgtg tgtggacaga actgctggct ggttgttaag   1920
ttgctactaa acacagtgtt gtttctcgtg gtctctgccc ttgttaacta ggattgaggc   1980
acttttgaac ataggtacct gggtcctaag ggcgaattcc agcacactgg cggccgttac   2040
tagtggatcc gagctcggta ccaagctcca gctgggaata gagataggag gggacccagc   2100
tggatgcagt gggcagtggg ggtcatagag tcaagagggt acagaataca atggggtcct   2160
agtatcatgg tggaggtcag aaagagccct aaaagagagg gtcaaggtag gaggttagtg   2220
aaggtccacc tccaccctct ccaggacagg gacatcaggc cacaattaat ttctctgcag   2280
ttggtgagtg gtcatggtct ctggagtccc cagcatccag agtgtccctg gtctagtggt   2340
ccccccttc tgagccacag ccactttctc catcaaatga ggccagtaat acccatccca   2400
tagtgatgct gtgaggatga gatgagcatc tgtaagtgct gaagataatc cctgacacat   2460
cccaagcatt cagcagtgca agcatacact tacacggcac tccccagagc caggcatgtg   2520
ctggtgcctc atacacgtga ccacatttga tcgtcacaat gaccctgtga gggagactgt   2580
gcaacagagg actgaccttg ctcaaagacc tcaggcgttt ccctcagag cctgagaggt   2640
catctctttt tttttttttt tttcctttct ttcttttct tttccatttc ttttctttg   2700
caagaggtca tctctaatgc tttgaatat cctgccagat tagagtccct tgttcacct   2760
gaaggtttgg gccacaccag atagtctaac ggtgtgattt gtgctgaagg ttttgagcca   2820
```

```
cactatatca gctagatttc tagagcggcc ggccgcaata aaatatcttt attttcatta    2880
catctgtgtg ttggttttt gtgtgaatcg atagtactaa catacgctct ccatcaaaac    2940
aaaacgaaac aaaacaaact agcaaaatag gctgtcccca gtgcaagtgc aggtgccaga    3000
acatttctct atcgataggt accgagctca tttaggtgac actatagaat acaagcttgc    3060
atgcctgcag gtccgaggga cagtactccg ctcggaggac agtactccgc tcggaggaca    3120
gtactccgct cggaggacag tactccgctc ggaggacagt actccgactc tagaggatcc    3180
ccagtcctat atatactcgc tctgcacttg gccctttttt acactgtgac tgattgagct    3240
ggtgccgtgt cgagtggtgt ctcgagatct gcgatctaag taagcttggc attccggtac    3300
tgttggtaaa gccaccatgg aagacgccaa aaacataaag aaaggcccgg cgccattcta    3360
tccgctggaa gatggaaccg ctggagagca actgcataag gctatgaaga gatacgccct    3420
ggttcctgga acaattgctt ttacagatgc acatatcgag gtggacatca cttacgctga    3480
gtacttcgaa atgtccgttc ggttggcaga agctatgaaa cgatatgggc tgaatacaaa    3540
tcacagaatc gtcgtatgca gtgaaaactc tcttcaattc tttatgccgg tgttgggcgc    3600
gttatttatc ggagttgcag ttgcgcccgc gaacgacatt tataatgaac gtgaattgct    3660
caacagtatg ggcatttcgc agcctaccgt ggtgttcgtt tccaaaaagg ggttgcaaaa    3720
aattttgaac gtgcaaaaaa agctcccaat catccaaaaa attattatca tggattctaa    3780
aacggattac cagggatttc agtcgatgta cacgttcgtc acatctcatc tacctcccgg    3840
ttttaatgaa tacgattttg tgccagagtc cttcgatagg gacaagacaa ttgcactgat    3900
catgaactcc tctggatcta ctggtctgcc taaaggtgtc gctctgcctc atagaactgc    3960
ctgcgtgaga ttctcgcatg ccagagatcc tattttggc aatcaaatca ttccggatac    4020
tgcgatttta agtgttgttc cattccatca cggttttgga atgtttacta cactcggata    4080
tttgatatgt ggatttcgag tcgtcttaat gtatagattt gaagaagagc tgtttctgag    4140
gagccttcag gattacaaga ttcaaagtgc gctgctggtg ccaaccctat tctccttctt    4200
cgccaaaagc actctgattg acaaatacga tttatctaat ttacacgaaa ttgcttctgg    4260
tggcgctccc ctctctaagg aagtcgggga agcggttgcc aagaggttcc atctgccagg    4320
tatcaggcaa ggatatgggc tcactgagac tacatcagct attctgatta cacccgaggg    4380
ggatgataaa ccgggcgcgg tcggtaaagt tgttccattt tttgaagcga aggttgtgga    4440
tctggatacc gggaaaacgc tgggcgttaa tcaaagaggc gaactgtgtg tgagaggtcc    4500
tatgattatg tccggttatg taaacaatcc ggaagcgacc aacgccttga ttgacaagga    4560
tggatggcta cattctggag acatagctta ctgggacgaa gacgaacact tcttcatcgt    4620
tgaccgcctg aagtctctga ttaagtacaa aggctatcag gtggctcccg ctgaattgga    4680
atccatcttg ctccaacacc ccaacatctt cgacgcaggt gtcgcaggtc ttcccgacga    4740
tgacgccggt gaacttcccg ccgccgttgt tgttttggag cacggaaaga cgatgacgga    4800
aaaagagatc gtggattacg tcgccagtca agtaacaacc gcgaaaaagt tgcgcggagg    4860
agttgtgttt gtggacgaag taccgaaagg tcttaccgga aaactcgacg caagaaaaat    4920
cagagagatc ctcataaagg ccaagaaggg cggaaagatc gccgtgtaat tctaggtacc    4980
gagctcttac gcgtgctagc cctcgacaat caacctctgg attacaaaat ttgtgaaaga    5040
ttgactggta ttcttaacta tgttgctcct tttacgctat gtggatacgc tgctttaatg    5100
cctttgtatc atgctattgc ttcccgtatg gctttcattt tctcctcctt gtataaatcc    5160
tggttgctgt ctctttatga ggagttgtgg cccgttgtca ggcaacgtgg cgtggtgtgc    5220
```

```
actgtgtttg ctgacgcaac ccccactggt tggggcattg ccaccacctg tcagctcctt    5280
tccgggactt tcgctttccc cctccctatt gccacggcgg aactcatcgc cgcctgcctt    5340
gcccgctgct ggacaggggc tcggctgttg ggcactgaca attccgtggt gttgtcgggg    5400
aagctgacgt cctttccatg gctgctcgcc tgtgttgcca cctggattct gcgcgggacg    5460
tccttctgct acgtcccttc ggccctcaat ccagcgacc ttccttcccg cggcctgctg    5520
ccggctctgc ggcctcttcc gcgtcttcgc cttcgccctc agacgagtcg gatctccctt    5580
tgggccgcct ccccgcctgg aattcgagct cggtacgggc tcgactagag tcggggcggc    5640
cggccgcttc gagcagacat gataagatac attgatgagt ttggacaaac cacaactaga    5700
atgcagtgaa aaaatgctt tatttgtgaa atttgtgatg ctattgcttt atttgtaacc    5760
attataagct gcaataaaca agttaacaac aacaattgca ttcattttat gtttcaggtt    5820 caggggggagg tgtgggaggt tttttaaagc aagtaaaacc tctacaaatg tggtaaaatc    5880
gataaggatc cgtcgaccga tgcccttgag agccttcaac ccagtcagct ccttccggtg    5940 ggcgcgggc atgactatcg tcgccgcact tatgactgtc ttctttatca tgcaactcgt    6000
aggacaggtg ccggcagcgc tcttccgctt cctcgctcac tgactcgctg cgctcggtcg    6060
ttcggctgcg gcgagcggta tcagctcact caaaggcggt aatacggtta tccacagaat    6120
caggggataa cgcaggaaag aacatgtgag caaaaggcca gcaaaggcc aggaaccgta    6180 aaaaggccgc gttgctggcg tttttccata ggctccgccc ccctgacgag catcacaaaa    6240
atcgacgctc aagtcagagg tggcgaaacc cgacaggact ataaagatac caggcgtttc    6300
cccctggaag ctccctcgtg cgctctcctg ttccgaccct gccgcttacc ggatacctgt    6360
ccgcctttct cccttcggga agcgtggcgc tttctcaatg ctcacgctgt aggtatctca    6420
gttcggtgta ggtcgttcgc tccaagctgg gctgtgtgca cgaaccccc gttcagcccg    6480 accgctgcgc cttatccggt aactatcgtc ttgagtccaa cccggtaaga cacgacttat    6540
cgccactggc agcagccact ggtaacagga ttagcagagc gaggtatgta ggcggtgcta    6600
cagagttctt gaagtggtgg cctaactacg gctacactag aaggacagta tttggtatct    6660
gcgctctgct gaagccagtt accttcggaa aaagagttgg tagctcttga tccggcaaac    6720
aaaccaccgc tggtagcggt ggtttttttg tttgcaagca gcagattacg cgcagaaaaa    6780
aaggatctca agaagatcct ttgatctttt ctacggggtc tgacgctcag tggaacgaaa    6840
actcacgtta agggattttg gtcatgagat tatcaaaaag gatcttcacc tagatccttt    6900
taaattaaaa atgaagtttt aaatcaatct aaagtatata tgagtaaact tggtctgaca    6960
gttaccaatg cttaatcagt gaggcaccta tctcagcgat ctgtctattt cgttcatcca    7020
tagttgcctg actccccgtc gtgtagataa ctacgatacg ggagggctta ccatctggcc    7080
ccagtgctgc aatgataccg cgagacccac gctcaccggc tccagattta tcagcaataa    7140
accagccagc cggaagggcc gagcgcagaa gtggtcctgc aactttatcc gcctccatcc    7200
agtctattaa ttgttgccgg gaagctagag taagtagttc gccagttaat agtttgcgca    7260
acgttgttgc cattgctaca ggcatcgtgg tgtcacgctc gtcgtttggt atggcttcat    7320
tcagctccgg ttcccaacga tcaaggcgag ttacatgatc ccccatgttg tgcaaaaaag    7380
cggttagctc cttcggtcct ccgatcgttg tcagaagtaa gttggccgca gtgttatcac    7440
tcatggttat ggcagcactg cataattctc ttactgtcat gccatccgta agatgctttt    7500
ctgtgactgg tgagtactca accaagtcat tctgagaata gtgtatgcgg cgaccgagtt    7560
```

| | |
|---|---|
| gctcttgccc ggcgtcaata cgggataata ccgcgccaca tagcagaact ttaaaagtgc | 7620 |
| tcatcattgg aaaacgttct tcggggcgaa aactctcaag gatcttaccg ctgttgagat | 7680 |
| ccagttcgat gtaacccact cgtgcaccca actgatcttc agcatctttt actttcacca | 7740 |
| gcgtttctgg gtgagcaaaa acaggaaggc aaaatgccgc aaaaaaggga ataagggcga | 7800 |
| cacggaaatg ttgaatactc atactcttcc tttttcaata ttattgaagc atttatcagg | 7860 |
| gttattgtct catgagcgga tacatatttg aatgtattta gaaaaataaa caaatagggg | 7920 |
| ttccgcgcac atttccccga aaagtgccac ctgacgcgcc ctgtagcggc gcattaagcg | 7980 |
| cggcgggtgt ggtggttacg cgcagcgtga ccgctacact tgccagcgcc ctagcgcccg | 8040 |
| ctcctttcgc tttcttccct tcctttctcg ccacgttcgc cggctttccc cgtcaagctc | 8100 |
| taaatcgggg gctccctta gggttccgat ttagtgcttt acggcacctc gaccccaaaa | 8160 |
| aacttgatta gggtgatggt tcacgtagtg ggccatcgcc ctgatagacg gttttcgcc | 8220 |
| ctttgacgtt ggagtccacg ttctttaata gtggactctt gttccaaact ggaacaacac | 8280 |
| tcaaccctat ctcggtctat tcttttgatt tataagggat tttgccgatt tcggcctatt | 8340 |
| ggttaaaaaa tgagctgatt taacaaaaat ttaacgcgaa ttttaacaaa atattaacgt | 8400 |
| ttacaatttc ccattcgcca ttcaggctgc gcaactgttg ggaagggcga tcggtgcggg | 8460 |
| cctcttcgct attacgccag cccaagctac catgataagt aagtaatatt aa | 8512 |

<210> SEQ ID NO 21
<211> LENGTH: 8565
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 21

| | |
|---|---|
| cgccattcag gctgcgcaac tgttgggaag ggcgatcggt gcgggcctct tcgctattac | 60 |
| gccagcccaa gctaccatga taagtaagta atattaaggt acgggaggta cttggagcgg | 120 |
| ccgcgatcca gacatgataa gatacattga tgagtttgga caaccacaa ctagaatgca | 180 |
| gtgaaaaaaa tgctttattt gtgaaatttg tgatgctatt gctttatttg taaccattat | 240 |
| aagctgcaat aaacaagtta acaacaacaa ttgcattcat tttatgtttc aggttcaggg | 300 |
| ggaggtgtgg gaggttttt aaagcaagta aaacctctac aaatgtggta tggctgatta | 360 |
| tgatcatgaa cagactgtga ggactgaggg gcctgaaatg agccttggga ctgtgaattt | 420 |
| aaaatacaca aacaattaga atcagtagtt aacacattta tacacttaaa aatttttatat | 480 |
| ttaccttaga gctttaaatc tctgtaggta gtttgtccaa ttatgtcaca ccacagaagt | 540 |
| aaggttcctt cacaaagatc ccaagctgtc gatcgacatt tctagaggat ctcggacccg | 600 |
| gggaatcccc gtccccaac atgtccagat cgaaatcgtc tagcgcgtcg gcatgcgcca | 660 |
| tcgccacgtc ctcgccgtct aagtggagct cgtccccag gctgacatcg gtcgggggg | 720 |
| cggatctcgg acccggggaa tccccgtccc ccaacatgtc cagatcgaaa tcgtctagcg | 780 |
| cgtcggcatg cgccatcgcc acgtcctcgc cgtctaagtg gagctcgtcc cccaggctga | 840 |
| catcggtcgg gggggcggat ccccgggct gcaggaattc cggcgataca gtcaactgtc | 900 |
| tttgaccttt gttactactc tcttccgatg atgatgtcgc acttattcta tgctgtctca | 960 |
| atgttagagg catatcagtc tccactgaag ccaatctatc tgtgacggca tctttattca | 1020 |
| cattatcttg tacaaataat cctgttaaca atgctttat atcctgtaaa gaatccattt | 1080 |

```
tcaaaatcat gtcaaggtct tctcgaggaa aaatcagtag aaatagctgt tccagtcttt    1140
ctagccttga ttccacttct gtcagatgtg ccctagtcag cggagacctt ttggttttgg    1200
gagagtagcg acactcccag ttgttcttca gacacttggc gcacttcggt ttttctttgg    1260
agcacttgag ctttttaagt cggcaaatat cgcatgcttg ttcgatagaa gacagtagct    1320
tcatctttca ggaggctagg gccgccccac gtgcgcagca ggacgcagcg ctgcctgaaa    1380
ctcgcgccgc gaggagaggg cggggccgcg gaaaggaaag ggggggggctg ggaggcccgg    1440 aggggggctgg gccggggacc cgggagggggt cgggacgggg cggggtccgc gcggaggagg    1500
cggagctgga aggtgaaggg gcaggacggg tgcccgggtc cccagtccct ccgccacgtg    1560
gggagcgcgg tcctgggcgt ctgtgcccgc gaatccactg ggagcccggc ctggccccga    1620
cagcgcagct gctccgggcg gacccggggg tctgggccgc gcttccccgc ccgcgcgccg    1680
ctcgcgctcc cagggtgcag ggacgccagc gagggcccca gcggagagag gtcgaatcgg    1740
cctaggctgt ggggtaaccc gagggaggggg cctctagata taagggcgaa ttccagcaca    1800
ctggcggccg ttactagtgg atccgagctc ggtacacaga cattgacatt gtgtcatcta    1860
gtatacaaat aggttcttgg agtactttac taggcatgga caatgcccaa tgcctgtccc    1920
attcttcagg catattttta tttgtgggct ttatgtccct attaagaaaa agactaagaa    1980
caagatgcta tcatattttc ttaactggaa tggtagatgt ttaaacatga tgactaccaa    2040
gcttggctag aacattgtgt catctagtat acaaataggt tcttggagta ctttactagg    2100
catggacaat gcccaatgcc tgtcccattc ttcaggcata ttttatttg tgggctttat    2160 gtccctatta agaaaaagac taagaacaag atgctatcat aagctccaag cttatcgcca    2220
gctgggaata gagataggag gggacccagc tggatgcagt gggcagtggg ggtcatagag    2280
tcaagagggt acagaataca atggggtcct agtatcatgg tggaggtcag aaagagccct    2340
aaaagagagg gtcaaggtag gaggttagtg aaggtccacc tccaccctct ccaggacagg    2400
gacatcaggc cacaattaat ttctctgcag ttggtgagtg gtcatggtct ctggagtccc    2460
cagcatccag agtgtccctg gtctagtggt cccccctttc tgagccacag ccactttctc    2520
catcaaatga ggccagtaat acccatccca tagtgatgct gtgaggatga gatgagcatc    2580
tgtaagtgct gaagataatc cctgacacat cccaagcatt cagcagtgca agcatacact    2640
tacacggcac tccccagagc caggcatgtg ctggtgcctc atacacgtga ccacatttga    2700
tcgtcacaat gaccctgtga gggagactgt gcaacagagg actgaccttg ctcaaagacc    2760
tcaggcgttt cccctcagag cctgagaggt catctctttt ttttttttt tttccttct    2820 ttcttttct tttccatttc tttttctttg caagaggtca tctctaatgc tttggaatat    2880
cctgccagat tagagtccct ttgttcacct gaaggtttgg gccacaccag atagtctaac    2940
ggtgtgattt gtgctgaagg ttttgagcca cactatatca gctagatttc tagagcggcc    3000
ggccgcaata aaatatcttt attttcatta catctgtgtg ttggtttttt gtgtgaatcg    3060
atagtactaa catacgctct ccatcaaaac aaaacgaaac aaaacaaact agcaaaatag    3120
gctgtcccca gtgcaagtgc aggtgccaga acatttctct atcgataggt accgagctca    3180
tttaggtgac actatagaat acaagcttgc atgcctgcag gtccggagga cagtactccg    3240 ctcgaggac agtactccgc tcggaggaca gtactccgct cggaggacag tactccgctc    3300
ggaggacagt actccgactc tagaggatcc ccagtcctat atatactcgc tctgcacttg    3360
gccctttttt acactgtgac tgattgagct ggtgccgtgt cgagtggtgt ctcgagatct    3420
gcgatctaag taagcttggc attccggtac tgttggtaaa gccaccatgg aagacgccaa    3480
```

-continued

```
aaacataaag aaaggcccgg cgccattcta tccgctggaa gatggaaccg ctggagagca    3540
actgcataag gctatgaaga gatacgccct ggttcctgga acaattgctt ttacagatgc    3600
acatatcgag gtggacatca cttacgctga gtacttcgaa atgtccgttc ggttggcaga    3660
agctatgaaa cgatatgggc tgaatacaaa tcacagaatc gtcgtatgca gtgaaaactc    3720
tcttcaattc tttatgccgg tgttgggcgc gttatttatc ggagttgcag ttgcgcccgc    3780
gaacgacatt tataatgaac gtgaattgct caacagtatg ggcatttcgc agcctaccgt    3840
ggtgttcgtt tccaaaaagg ggttgcaaaa aattttgaac gtgcaaaaaa agctcccaat    3900
catccaaaaa attattatca tggattctaa aacggattac cagggatttc agtcgatgta    3960
cacgttcgtc acatctcatc tacctcccgg ttttaatgaa tacgattttg tgccagagtc    4020
cttcgatagg gacaagacaa ttgcactgat catgaactcc tctggatcta ctggtctgcc    4080
taaaggtgtc gctctgcctc atagaactgc ctgcgtgaga ttctcgcatg ccagagatcc    4140 tattttggc aatcaaatca ttccggatac tgcgatttta agtgttgttc cattccatca    4200
cggttttgga atgtttacta cactcggata tttgatatgt ggatttcgag tcgtcttaat    4260
gtatagattt gaagaagagc tgtttctgag gagccttcag gattacaaga ttcaaagtgc    4320
gctgctggtg ccaaccctat tctccttctt cgccaaaagc actctgattg acaaatacga    4380
tttatctaat ttacacgaaa ttgcttctgg tggcgctccc ctctctaagg aagtcgggga    4440
agcggttgcc aagaggttcc atctgccagg tatcaggcaa ggatatgggc tcactgagac    4500
tacatcagct attctgatta cacccgaggg ggatgataaa ccgggcgcgg tcggtaaagt    4560
tgttccattt tttgaagcga aggttgtgga tctggatacc gggaaaacgc tgggcgttaa    4620
tcaaagaggc gaactgtgtg tgagaggtcc tatgattatg tccggttatg taaacaatcc    4680
ggaagcgacc aacgccttga ttgacaagga tggatggcta cattctggag acatagctta    4740
ctgggacgaa gacgaaacact tcttcatcgt tgaccgcctg aagtctctga ttaagtacaa    4800
aggctatcag gtggctcccg ctgaattgga atccatcttg ctccaacacc ccaacatctt    4860
cgacgcaggt gtcgcaggtc ttcccgacga tgacgccggt gaacttcccg ccgccgttgt    4920
tgttttggag cacggaaaga cgatgacgga aaaagagatc gtggattacg tcgccagtca    4980
agtaacaacc gcgaaaaagt tgcgcggagg agttgtgttt gtggacgaag taccgaaagg    5040
tcttaccgga aaactcgacg caagaaaaat cagagagatc ctcataaagg ccaagaaggg    5100
cggaaagatc gccgtgtaat tctaggtacc gagctcttac gcgtgctagc cctcgacaat    5160
caacctctgg attacaaaat ttgtgaaaga ttgactggta ttcttaacta tgttgctcct    5220
tttacgctat gtggatacgc tgctttaatg cctttgtatc atgctattgc ttcccgtatg    5280
gctttcattt tctcctcctt gtataaatcc tggttgctgt ctctttatga ggagttgtgg    5340
cccgttgtca gcaacgtggc gtggtgtgc actgtgtttg ctgacgcaac ccccactggt    5400
tggggcattg ccaccacctg tcagctcctt tccgggactt tcgctttccc cctccctatt    5460
gccacggcgg aactcatcgc cgcctgcctt gcccgctgct ggacaggggc tcggctgttg    5520
ggcactgaca attccgtggt gttgtcgggg aagctgacgt cctttccatg gctgctcgcc    5580
tgtgttgcca cctggattct gcgcgggacg tccttctgct acgtcccttc ggccctcaat    5640
ccagcggacc ttccttcccg cggcctgctg ccggctctgc ggcctcttcc gcgtcttcgc    5700
cttcgccctc agacgagtcg gatctcccttt gggccgcct cccgcctgg aattcgagct    5760 cggtacgggc tcgactagag tcggggcggc cggccgcttc gagcagacat gataagatac    5820
```

```
attgatgagt tggacaaac cacaactaga atgcagtgaa aaaaatgctt tatttgtgaa    5880
atttgtgatg ctattgcttt atttgtaacc attataagct gcaataaaca agttaacaac    5940
aacaattgca ttcattttat gtttcaggtt caggggagg tgtgggaggt tttttaaagc    6000
aagtaaaacc tctacaaatg tggtaaaatc gataaggatc cgtcgaccga tgcccttgag    6060
agccttcaac ccagtcagct ccttccggtg ggcgcgggc atgactatcg tcgccgcact    6120
tatgactgtc ttctttatca tgcaactcgt aggacaggtg ccggcagcgc tcttccgctt    6180
cctcgctcac tgactcgctg cgctcggtcg ttcggctgcg gcgagcggta tcagctcact    6240
caaaggcggt aatacggtta ccacagaat caggggataa gcaggaaag aacatgtgag    6300 caaaaggcca gcaaaaggcc aggaaccgta aaaaggccgc gttgctggcg ttttccata    6360 ggctccgccc cctgacgag catcacaaaa atcgacgctc aagtcagagg tggcgaaacc    6420
cgacaggact ataaagatac caggcgtttc ccctggaag ctccctcgtg cgctctcctg    6480 ttccgacccct gccgcttacc ggatacctgt ccgcctttct cccttcggga agcgtggcgc    6540
tttctcaatg ctcacgctgt aggtatctca gttcggtgta ggtcgttcgc tccaagctgg    6600
gctgtgtgca cgaaccccc gttcagcccg accgctgcgc cttatccggt aactatcgtc    6660
ttgagtccaa cccggtaaga cacgacttat cgccactggc agcagccact ggtaacagga    6720
ttagcagagc gaggtatgta ggcggtgcta cagagttctt gaagtggtgg cctaactacg    6780
gctacactag aaggacagta tttggtatct gcgctctgct gaagccagtt accttcggaa    6840
aaagagttgg tagctcttga tccggcaaac aaaccaccgc tggtagcggt ggtttttttg    6900
tttgcaagca gcagattacg cgcagaaaaa aaggatctca agaagatcct ttgatctttt    6960
ctacggggtc tgacgctcag tggaacgaaa actcacgtta agggattttg gtcatgagat    7020
tatcaaaaag gatcttcacc tagatccttt taaattaaaa atgaagtttt aaatcaatct    7080
aaagtatata tgagtaaact tggtctgaca gttaccaatg cttaatcagt gaggcaccta    7140
tctcagcgat ctgtctattt cgttcatcca tagttgcctg actccccgtc gtgtagataa    7200
ctacgatacg ggagggctta ccatctggcc ccagtgctgc aatgataccg cgagacccac    7260
gctcaccggc tccagattta tcagcaataa accagccagc cggaagggcc gagcgcagaa    7320
gtggtcctgc aactttatcc gcctccatcc agtctattaa ttgttgccgg gaagctagag    7380
taagtagttc gccagttaat agtttgcgca acgttgttgc cattgctaca ggcatcgtgg    7440
tgtcacgctc gtcgtttggt atggcttcat tcagctccgg ttcccaacga tcaaggcgag    7500
ttacatgatc ccccatgttg tgcaaaaaag cggttagctc cttcggtcct ccgatcgttg    7560
tcagaagtaa gttggccgca gtgttatcac tcatggttat ggcagcactg cataattctc    7620
ttactgtcat gccatccgta agatgctttt ctgtgactgg tgagtactca accaagtcat    7680
tctgagaata gtgtatgcgg cgaccgagtt gctcttgccc ggcgtcaata cgggataata    7740
ccgcgccaca tagcagaact ttaaaagtgc tcatcattg aaaacgttct cggggcgaa    7800 aactctcaag gatcttaccg ctgttgagat ccagttcgat gtaacccact cgtgcaccca    7860
actgatcttc agcatctttt actttcacca gcgtttctgg gtgagcaaaa acaggaaggc    7920
aaaatgccgc aaaaaaggga ataagggcga cacggaaatg ttgaatactc atactcttcc    7980
tttttcaata ttattgaagc atttatcagg gttattgtct catgagcgga tacatatttg    8040
aatgtattta gaaaaataaa caaatagggg ttccgcgcac atttccccga aaagtgccac    8100
ctgacgcgcc ctgtagcggc gcattaagcg cggcgggtgt ggtggttacg cgcagcgtga    8160
ccgctacact tgccagcgcc ctagcgcccg ctcctttcgc tttcttccct tcctttctcg    8220
```

```
ccacgttcgc cggctttccc cgtcaagctc taaatcgggg gctcccttta gggttccgat    8280
ttagtgcttt acggcacctc gaccccaaaa aacttgatta gggtgatggt tcacgtagtg    8340
ggccatcgcc ctgatagacg ttttttcgcc ctttgacgtt ggagtccacg ttctttaata    8400
gtggactctt gttccaaact ggaacaacac tcaaccctat ctcggtctat tcttttgatt    8460
tataagggat tttgccgatt tcggcctatt ggttaaaaaa tgagctgatt taacaaaaat    8520
ttaacgcgaa ttttaacaaa atattaacgt ttacaatttc ccatt                   8565

<210> SEQ ID NO 22
<211> LENGTH: 279
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 22
gacactatag aatacaagct tgcatgcctg caggtccgga ggacagtact ccgctcggag     60
gacagtactc cgctcggagg acagtactcc gctcggagga cagtactccg ctcggaggac    120
agtactccga ctctagagga tccccagtcc tatatatact cgctctgcac ttggcccttt    180
tttacactgt gactgattga gctggtgccg tgtcgagtgg tgtctcgaga tctgcgatct    240
aagtaagctt ggcattccgg tactgttggt aaagccacc                           279

<210> SEQ ID NO 23
<211> LENGTH: 650
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 23
gctagctacg ggccagatat acgcgttgac attgattatt gactagttat taatagtaat     60
caattacggg gtcattagtt catagcccat atatggagtt ccgcgttaca taacttacgg    120
taaatggccc gcctggctga ccgcccaacg accccgccc attgacgtca ataatgacgt    180
atgttcccat agtaacgcca atagggactt tccattgacg tcaatgggtg gagtatttac    240
ggtaaactgc ccacttggca gtacatcaag tgtatcatat gccaagtacg ccccctattg    300
acgtcaatga cggtaaatgg cccgcctggc attatgccca gtacatgacc ttatgggact    360
ttcctacttg gcagtacatc tacgtattag tcatcgctat taccatggtg atgcggtttt    420
ggcagtacat caatgggcgt ggatagcggt ttgactcact cgagagacgg tgagagcgag    480
tcagggattg gctggtctgc ttcgggcggg ctaaaggaag gttcaagtgg agctctccta    540
accgacgcgc gtctgtggag aagcggcttg gtcgggggtg gtctcgtggg gtcctgcctg    600
tttagtcgct ttcagggttc ttgagcccct tcacgaccgt caccaagctt                650

<210> SEQ ID NO 24
<211> LENGTH: 678
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 24
gctagctacg ggccagatat acgcgttgac attgattatt gactagttat taatagtaat     60
```

```
caattacggg gtcattagtt catagcccat atatggagtt ccgcgttaca taacttacgg    120
taaatggccc gcctggctga ccgcccaacg accccgccc attgacgtca ataatgacgt     180
atgttcccat agtaacgcca atagggactt tccattgacg tcaatgggtg gagtatttac    240
ggtaaactgc ccacttggca gtacatcaag tgtatcatat gccaagtacg cccctattg    300 acgtcaatga cggtaaatgg cccgcctggc attatgccca gtacatgacc ttatgggact    360
ttcctacttg gcagtacatc tacgtattag tcatcgctat taccatggtg atgcggtttt    420
ggcagtacat caatgggcgt ggatagcggt ttgactcact cgagcggccg ccagtgtgat    480
ggatatctgc agaattcgcc cttgcgatct gtcagagcac ctcgcgagcg tacgtgcctc    540
aggaagtgac gcacagcccc cctgggggcc ggggcgggg ccaggctata aaccgccggt    600 tagggccgc catcccctca gagcgtcggg atatcgggtg aagggcgaat tccagcacac    660
tggcggccgt tactagtg                                                  678
```

CANCER SPECIFIC PROMOTERS

The present invention claims priority to U.S. Provisional Application Ser. No. 60/559,111, filed Apr. 2, 2004, which is incorporated by reference herein in its entirety.

FIELD OF THE INVENTION

The present invention is directed to the fields of cell biology, molecular biology, cancer biology, and medicine. More particularly, the present invention regards cancer-specific regulatory sequences for regulation of expression of a therapeutic polynucleotide useful for cancer therapy.

BACKGROUND OF THE INVENTION

The ability to control expression of particular polynucleotides upon gene transfer is a useful function, particularly for applications where specific localized activity is desired. Such is the case for cancer, where it is prudent to confine destructive or lethal gene products to the cancerous cells while preventing at least in part such activity in normal cells.

Breast Cancer Tissue-Specific Expression

Current breast cancer therapies, such as chemotherapy (CT) and radiotherapy, have low selectivity for tumor cells and side effects for normal tissues. To minimize the side effects, these therapies are generally given in an intermittent manner, allowing normal cells to recover between treatment cycles. However, during the recovery period, some surviving cancer cells become more resistant to the treatment because of gene mutation. Consequently, cancer recurrence or progression may occur. Tumor-targeting gene therapy minimizes treatment side effects and the risk of developing resistance by acting on the tumor-specific signaling pathways.

One breast cancer-specific promoter described herein comprises selected portions of the topoisomerase IIα gene. Although the 5' flanking region of the topoisomerase IIα gene has been known for some time Hochhauser et al., 1992), a particular active region described herein has not been demonstrated to be useful for breast cancer tissue, even when linked to cytomegalovirus enhancer (Mo et al., 1998).

Another breast cancer-specific promoter described herein comprises selected portions of the transferrin receptor promoter. Transferrin receptor expression has been localized in breast tissue (Fuernkranz et al., 1991; Shterman et al., 1991) and in breast cancer (Bauman et al., 1997; Shindelman et al., 1981), but a particular region that provides such activity has not been disclosed.

Prostate Cancer Tissue-Specific Expression

Prostate-specific promoters, such as PSA, probasin, and hK2, have been recently developed. The activities of these promoters are androgen-dependent and the use of androgen-responsive vectors to direct expression of therapeutic genes to prostatic tissue is helpful for numerous disease stages. Although such prostate-specific promoters responsive to androgen receptor have been developed by the present inventors (Xie et al., Cancer Res 2001) and other groups (Zhang et al., Mol Endocrinol 2000), these androgen-dependent promoters may be less active after castration or androgen ablation therapy, which are the main modalities for progressive prostate cancer treatment. Patients treated with compositions comprising these promoters may fail this kind of therapy and die of recurrent androgen-independent prostate cancer (AIPC). A novel promoter for prostate cancer gene therapy that will be active in both ADPC and AIPC to treat metastatic and recurrent hormonal refractory prostate cancer is lacking in the art.

Pancreatic Cancer Tissue-Specific Expression

Pancreatic cancer is one of the most aggressive human malignancies and the fifth cause of cancer death, given that no effective modalities are available. The present invention addresses such a need by providing a promoter effective to regulate expression of a therapeutic polynucleotide specifically in pancreatic cancer cells.

BRIEF SUMMARY OF THE INVENTION

The present invention provides novel tissue-specific promoters for regulation of expression of a therapeutic polynucleotide. These therapeutic compositions and methods that utilize them are helpful for cancer treatment, and a skilled artisan recognizes that any additional means in an arsenal to fight cancer is beneficial to public health.

In particular, the invention provides compositions, such as therapeutics, and methods of using same directed to cancer-specific regulated expression of a therapeutic polynucleotide in gene therapy for cancer, such as at least ovarian, breast, pancreatic, and prostate cancer, for example.

Thus, the present invention generally relates to methods for inhibiting proliferation in a cancer cell and/or tumor cell, the method comprising contacting the cell with a therapeutic polypeptide in an amount effective to inhibit proliferation utilizing a cancer-specific promoter, such as one described herein. Inhibition of proliferation may be indicated by, for example, an induction of apoptosis of a cell, such as, for example, in cell culture, inhibition of growth of a cancer cell line, reduction in size of a tumor, and/or an increase in survivability, in exemplary embodiments. More preferably, in some embodiments the cell in which proliferation is to be inhibited is a cell in a living organism, for example a human. The inhibition of such transformation has great utility in the prevention and/or treatment of such transformation-driven events as cancer, tumorigenesis, and/or metastasis.

The present invention encompasses polynucleotide constructs comprising control sequences that direct expression of a therapeutic polynucleotide in a particular tissue and/or type of cell. The polynucleotide may be contacted with or introduced to a cell through any of a variety of manners known to those of skill. The therapeutic polynucleotide may be introduced through direct introduction of the polynucleotide to a cell or tissue of interest. In this case, the therapeutic polynucleotide may be obtained through any method known in the art.

In specific aspects of the invention, RNA or DNA comprising the therapeutic polynucleotide may be introduced to the cell by any manner known in the art. In certain preferred embodiments, the therapeutic polynucleotide is introduced into the cell through the introduction of a DNA segment that encodes the therapeutic gene product. In some such embodiments, it is envisioned that the DNA segment comprising the therapeutic polynucleotide is operatively linked to the inventive control sequences. The construction of such gene/control sequence DNA constructs is well-known within the art and is described in detail herein.

In certain embodiments for introduction, the DNA segment may be located on a vector, for example, a plasmid vector or a viral vector. The virus vector may be, for example, retrovirus, adenovirus, herpesvirus, vaccina virus, and adeno-associated virus. Such a DNA segment may be used in a variety of methods related to the invention. The vector may be used to deliver a mutant bik polynucleotide to a cell in one of the gene-therapy embodiments of the invention, in specific embodiments. Also, such vectors can be used to transform cultured cells, and such cultured cells could be used, inter alia, for the expression of mutant Bik in vitro.

A skilled artisan recognizes that the promoters of the invention are useful in any context, including non-cancerous cell-specific expression or even expression of a polynucleotide that is not cell- or tissue-specific in nature.

In a particular embodiment, a therapeutic gene product is effective on the respective breast, pancreatic, or prostate cancer tissue. In exemplary embodiments, the present invention is useful for delivering genetic constructs that treat cancers that are estrogen receptor positive, EGF receptor overexpressing, Her2/neu-overexpressing, Her-2/neu-nonoverexpressing, Akt overexpressing, androgen dependent, and/or angrogen independent, for example. That is, the therapeutic gene product is effective on the respective cancer cells regardless of their status of oncogene overexpression, such as Her-2/neu, EGFR, AKT, or regardless of whether their growth is hormone dependent (such as, for example, MCF-7) or not (such as, for example, PC3).

A skilled artisan is aware of publicly available databases that provide therapeutic polynucleotide sequences, such as the National Center for Biotechnology Information's Gen-Bank database or commercially available databases, such as from Celera Genomics, Inc. (Rockville, Md.). Although there are a plethora of therapeutic polynucleotides that are known in the art that are later discovered that may be utilized in the invention, some examples include inhibitors of cellular proliferation, regulators of programmed cell death, tumor suppressors and antisense sequences of inducers of cellular proliferation. The therapeutic polynucleotide may encode small interfering RNAs or antisense sequences, for example. Particular exemplary therapeutic polynucleotides include those that encode mutant Bik, retinoblastoma, Blk, IL-12, IL-10, IFN-a, cytosine deaminase, GM-CSF, E1A, p53, and other pro-apoptotic proteins, for example. Also, a construct may comprise such therapeutic polynucleotides as TNFα or p53 or inducers of apoptosis including, but not limited to, Bik, p53, Bax, Bak, Bcl-x, Bad, Bim, Bok, Bid, Harakiri, Ad E1B, Bad and ICE-CED3 proteases. In specific aspects of the invention, a mutant Bik polynucleotide encoding an amino acid substitution at threonine 33, serine 35, or both is utilized. In particular aspects of these embodiments, the amino acids of the mutant Bik polypeptide are substituted with aspartate. In other particular aspects, one or more phosphorylation sites are defective in a mutant Bik. In additional embodiments, the mutant Bik retains anti-cell proliferative and/or pro-apoptotic activity.

In particular embodiments, a construct comprising the inventive therapeutic polynucleotide and respective cancer-specific control sequences is introduced into a cell that is a human cell. In many embodiments the cell is a tumor cell. In some presently preferred embodiments, the tumor cell is a breast tumor cell, an ovarian tumor cell, a prostate tumor cell, or a pancreatic tumor cell. In some embodiments, a construct comprising the therapeutic polynucleotide and respective cancer-specific control sequences is introduced by injection. In particular embodiments, the construct comprising the therapeutic polynucleotide and respective cancer-specific control sequences is comprised in a liposome.

In some embodiments of the present invention, a construct comprising the therapeutic polynucleotide and respective cancer-specific control sequences is used in combination with other anti-transformation/anti-cancer therapies. These other therapies may be known at the time of this application, or may become apparent after the date of this application. A construct comprising the therapeutic polynucleotide and respective cancer-specific control sequences may be used in combination with other therapeutic polypeptides, polynucleotides encoding other therapeutic polypeptides, chemotherapeutic agents, surgical methods, or radiation, for example.

A construct comprising the therapeutic polynucleotide and respective cancer-specific control sequences may be used in conjunction with any suitable chemotherapeutic agent. In one representative embodiment, the chemotherapeutic agent is Taxol. A construct comprising the therapeutic polynucleotide and respective cancer-specific control sequences also may be used in conjunction with radiotherapy. The type of ionizing radiation constituting the radiotherapy may comprise x-rays, γ-rays, and microwaves, for example. In certain embodiments, the ionizing radiation may be delivered by external beam irradiation or by administration of a radionuclide. The cancer-specific control sequence-regulated therapeutic gene product also may be used with other gene-therapy regimes. In particular embodiments, the construct comprising the therapeutic polynucleotide and respective cancer-specific control sequences is introduced into a tumor. The tumor may be in an animal, in particular, a mammal, such as a human.

Constructs having the inventive tissue-specific promoters regulating expression of a therapeutic gene product and polynucleotides of the present invention may also be introduced using any suitable method. A "suitable method" of introduction is one that places a therapeutic gene product in a position to reduce the proliferation of a tumor cell, preferably in the tissue or cells of interest and/or to ameliorate at least one cancer symptom. For example, injection, oral, and inhalation methods may be employed, with the skilled artisan being able to determine an appropriate method of introduction for a given circumstance, and the tissue-specific control sequences of the present invention direct expression of the therapeutic polynucleotide at least primarily in the tissue or cells of interest. In the embodiments where injection will be used, this injection may be intravenous, intraperitoneal, intramuscular, subcutaneous, intratumoral, or intrapleural, for example, or of any other appropriate form.

In certain other aspects of the present invention, there are provided therapeutic kits comprising in a suitable container a pharmaceutical formulation of a construct comprising the inventive control sequences. In additional aspects, a polynucleotide comprising the inventive control sequences comprises one or more cloning sites such that a desired polynucleotide, such as a polynucleotide of interest, may be cloned into the site. In particular embodiments, in a polynucleotide having a 5' to 3' orientation the one or more cloning sites may be located 5' of control sequence or 3' of the control sequence. In additional aspects, one or more therapeutic polynucleotides are also comprised in the kit, such as on the same nucleic acid molecule as the control sequences of the present invention. Such a kit may further comprise a pharmaceutical formulation of a therapeutic polypeptide, polynucleotide encoding a therapeutic polypeptide, and/or chemotherapeutic agent.

The anti-tumor activity, anti-cell proliferation activity, and/or pro-apoptotic activity provided by the gene product of the therapeutic polynucleotide may be useful for an organism other than the one from which the therapeutic polynucleotide is derived. For example, a murine therapeutic polynucleotide may be used alternatively or in addition for human treatment.

Thus, the present invention provides cancer-specific control sequences for targeted expression of a therapeutic polynucleotide, and, therefore, the present invention is directed to a novel improvement to the overall arts of cell growth control, including inhibition of cell proliferation and/or facilitation of cell death. In a specific embodiment, the inhibition of a cell proliferation comprises a delay in its rate of proliferation, a delay in its total cell numbers of proliferation, or both.

In an additional object of the present invention, there is a method of preventing growth of a cell in an individual comprising the step of administering to the individual a construct comprising cancer-specific control sequences that regulate expression of a therapeutic polynucleotide. In another specific embodiment, the administration of the construct comprising the inventive controls sequences is by a liposome.

In another object of the present invention, there is a method of preventing growth of a cell in an individual comprising the step of administering to the individual a nucleic acid comprising a tissue-specific control sequence encompassed by the present invention. In another specific embodiment, the administration of the nucleic acid is by a vector selected from the group consisting of a plasmid, a retroviral vector, an adenoviral vector, an adeno-associated viral vector, a liposome, and a combination thereof. The composition comprising the nucleic acid may be dispersed in a pharmacologically acceptable excipient, and the composition may be administered to an animal having a proliferative cell disorder.

In a further object of the invention, a therapeutic polynucleotide is regulated by a tissue-specific promoter, such as one that targets cancerous tissue. Although any promoter that targets cancerous tissue preferentially over non-cancerous tissue, in a specific embodiment the cancer-specific promoter is a breast cancer specific promoter, a prostate cancer-specific promoter, or a pancreatic-specific promoter, for example.

In a particular embodiment, a breast cancer-specific promoter comprises a breast cancer-specific sequence and, in further embodiments, an enhancer sequence that augments expression, such as the expression level, of the tissue-specific sequence. In a particular embodiment, a CMV promoter enhancer sequence is linked with a breast cancer-specific segment from the exemplary topoisomerase IIα (topoIIα) promoter or the exemplary transferrin receptor promoter. The inventors show herein that both of these composite promoters drive gene expression selectively in breast cancer cells and possess activity comparable to the CMV promoter. They are useful for gene targeting to target and treat primary and metastatic breast cancers with less toxicity to normal tissues.

In another embodiment, the expression of a therapeutic polynucleotide is regulated by a pancreatic-cancer specific promoter. In a particular embodiment, a novel pancreatic cancer specific promoter is utilized, such as one referred to herein as CTP, which is comprised of the minimal Cholecystokinin A receptor (CCKAR, −726 to +1 nucleotides) and the post-transcriptional regulatory element of the woodchuck hepatitis virus (WPRE). This engineered construct has a strong promoter activity and demonstrates specificity to pancreatic cancer cells in vitro and in vivo.

In another specific embodiment of the present invention, a prostate cancer-specific promoter regulates expression of a therapeutic polynucleotide. In a particular embodiment, the invention utilizes a novel prostate cancer specific promoter, such as one referred to herein as ATTP, comprised of the minimal human telomerase reverse transcriptase promoter (hTert), the post transcriptional regulatory element of the woodchuck hepatitis virus (WPRE), and the ARR2 element derived from plasmid ARR2PB, which is responsive to androgen stimulation. This engineered construct has a strong promoter activity and demonstrates specificity to both androgen-dependent and androgen-independent prostate cancer cells in vitro. This promoter can be used to specifically drive gene expression of a therapeutic polynucleotide in prostate cancer in vivo.

In one object of the invention, there is a polynucleotide construct comprising a breast cancer-specific control sequence, said control sequence comprising a selected portion of the topoisomerase IIα promoter or a selected portion of the transferrin receptor promoter. In particular, the control sequence comprises a selected portion of the topoisomerase IIα promoter, such as one comprising SEQ ID NO:12. The control sequence can also comprise a selected portion of the transferrin receptor promoter, such as one comprising SEQ ID NO:13.

In particular embodiments, constructs of the present invention comprise an enhancer, such as cytomegalovirus (CMV) enhancer, Glyceraldehyde-3-phosphate dehydrogenase promoter (GAPDH), or the β-actin promoter. The construct may further comprise a post-transcriptional regulatory sequence, such as, for example, woodchuck hepatitis virus post-transcriptional regulatory element (WPRE). In additional embodiments, a construct of the present invention comprises a two-step transcriptional amplification (TSTA) sequence, wherein the TSTA sequence includes a DNA binding domain, such as Gal1, Gal4, or LexA, and an activation domain, such as VP2 or VP16, for example. In particular aspects of the invention, the TSTA sequence is GAL4-VP2 or GAL4-VP16, for example.

In other particular embodiments, the control sequence is operably linked to a polynucleotide encoding a therapeutic gene product, such as one that is an inhibitor of cell proliferation, a regulator of programmed cell death, or a tumor suppressor, or one encompassing two of more of these activities. Constructs of the present invention may be comprised in a liposome.

In another object of the invention, a polynucleotide construct comprises a prostate cancer-specific control sequence that comprises at least two of the following sequences: a prostate tissue-specific control sequence; a cancer-specific control sequence; and a two-step transcriptional amplification (TSTA) sequence, said TSTA sequence including a DNA binding domain and an activation domain. In particular embodiments, the prostate tissue-specific control sequence comprises SEQ ID NO:17. In other particular embodiments, the cancer-specific control sequence comprises SEQ ID NO:18. Again, the DNA binding domain of the TSTA sequence may be Gal1, Gal4, or LexA, and the activation domain may be VP2 or VP16. In particular, the TSTA sequence is GAL4-VP2 or GAL4-VP16.

In a specific aspect of the invention, a polynucleotide construct that comprises a prostate cancer-specific control sequence further comprises a post-transcriptional regulatory sequence, such as woodchuck hepatitis virus post-transcriptional regulatory element (WPRE) sequence. The control sequence is operably linked to a polynucleotide encoding a therapeutic gene product, in some embodiments, such as an inhibitor of cell proliferation, a regulator of programmed cell death, or a tumor suppressor, or one encompassing two or more of these activities. The polynucleotide construct comprising a prostate cancer-specific control sequence may be comprised in a liposome.

In an additional object of the invention, there is a polynucleotide construct comprising a pancreatic cancer-specific control sequence comprising: a pancreatic tissue-specific control sequence, such as, for example, one comprising SEQ ID NO:14; and a two-step transcriptional amplification (TSTA) sequence, said TSTA sequence including a DNA binding domain and an activation domain. In the polynucleotide construct comprising a pancreatic cancer-specific control sequence, the DNA binding domain of the TSTA can be Gal1, Gal4, or LexA, and the activation domain of the TSTA can be VP2 or VP16. In particular, the TSTA sequence is GAL4-VP2 or GAL4-VP 16.

In particular, the construct may comprise a post-transcriptional regulatory sequence, such as the woodchuck hepatitis virus post-transcriptional regulatory element (WPRE). The control sequence can be operably linked to a polynucleotide encoding a therapeutic gene product, such as one that is an inhibitor of cell proliferation, a regulator of programmed cell death, or a tumor suppressor, or one encompassing one or more of these activities. The construct may be comprise in a liposome.

In an additional object of the invention, there is a method of inhibiting breast cancer cell proliferation, comprising contacting a breast cancer cell with an effective amount of a polynucleotide construct that comprises a selected portion of the topoisomerase IIα promoter or a selected portion of the transferrin receptor, wherein the selected portion may be operably linked to a polynucleotide encoding a gene product effective to inhibit the cell proliferation. The selected portion of the topoisomerase IIα promoter may comprise, for example, SEQ ID NO:12. The selected portion of the transferrin receptor may comprise SEQ ID NO:13, for example. In particular aspects of the invention, the construct further comprises an enhancer, such as CMV, Glyceraldehyde-3-phosphate dehydrogenase promoter (GAPDH), or the β-actin promoter.

In another object of the invention, there is a method of inhibiting prostate cancer cell proliferation, comprising contacting a prostate cancer cell with an effective amount of a polynucleotide construct having at least two of the following sequences: a prostate cell-specific control sequence; a two-step transcriptional amplification sequence; and a cancer cell-specific sequence, wherein the sequences are operably linked to a polynucleotide encoding a gene product effective to inhibit the prostate cancer cell proliferation. The construct may further comprise a post-transcriptional control sequence operably linked to the polynucleotide encoding a gene product effective to inhibit the prostate cancer cell proliferation, such as a WPRE sequence, for example.

In an additional object of the invention, there is a method of inhibiting pancreatic cancer cell proliferation, comprising contacting a pancreatic cancer cell with an effective amount of a polynucleotide construct comprising a pancreatic cell-specific sequence and a two-step amplification sequence, both of which are operably linked to a polynucleotide encoding a gene product effective to inhibit the cell proliferation. The construct may further comprise a post-transcriptional control sequence operably linked to the polynucleotide encoding a gene product effective to inhibit the cell proliferation, such as a WPRE sequence, for example.

In a further object of the invention, there is a method of treating breast cancer in an individual having the cancer, comprising contacting at least one breast cancer cell of the individual with a therapeutically effective amount of a polynucleotide construct comprising a selected portion of the topoisomerase IIα promoter or a selected portion of the transferrin receptor, wherein the selected portion is operably linked to a polynucleotide encoding a gene product effective to treat breast cancer. The construct may comprise a selected portion of the topoisomerase IIα promoter being one that comprises SEQ ID NO:12. The construct may also comprise a selected portion of the transferrin receptor promoter, such as one comprising SEQ ID NO:13. The construct may further comprise an enhancer, such as CMV enhancer, and the polynucleotide may be comprised in a liposome.

In another object of the present invention, there is a method of treating prostate cancer in an individual having the cancer, comprising contacting at least one prostate cancer cell of the individual with a therapeutically effective amount of a polynucleotide construct comprising at least two of the following: a prostate cell-specific control sequence; a cancer cell-specific control sequence; and a two-step transcriptional amplification sequence, wherein the sequences are operably linked to a polynucleotide encoding a gene product effective to treat prostate cancer. The polynucleotide construct may further comprise a post-transcriptional control sequence, such as a WPRE sequence, and the polynucleotide may be comprised in a liposome.

In a further object of the invention, there is a method of treating pancreatic cancer in an individual having the cancer, comprising contacting at least one pancreatic cancer cell of the individual with a therapeutically effective amount of a polynucleotide construct comprising a pancreatic cell-specific control sequence and a two-step transcriptional amplification sequence, both of which are operably linked to a polynucleotide encoding a gene product effective to treat pancreatic cancer. The construct may further comprise a post-transcriptional control sequence, such as a WPRE sequence. The polynucleotide may be comprised in a liposome.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 11A shows in vivo imaging of mice. The representative imaging of mice are shown. FIG. 11B shows firefly luciferase activity in tissue extracts was quantified with a luminometer and expressed as relative luciferase units per milligram of total protein. The ratio was calculated by comparing the level of luciferase activity of CTP mice to CMV mice.

FIG. 13A shows that an androgen responsive element ARR2 was placed upstream of hTERTp of hTERTp-TSTA-Luc or hTERTp-TSTA-Luc-WPRE composites. ARR2PB-driven Luc was as control. FIG. 13B demonstrates activity of hTERTp-based composites in prostate cancer cells. The data represent means of four independent experiments; bar, SD.

In FIG. 17A, there is BikDD expression in heart tissues from CMV-BikDD- and CT90-BikDD-treated mice (left and right panels, respectively). The samples in upper panels were stained with antisense BikDD probes, and the deep brown color indicated the positive signals. The lower panels showed the negative control experiments stained with sense BikDD probes. In FIG. 17B, there is BikDD expression in tumor tissues from CMV-BikDD- and CT90-BikDD-treated mice (left and right panels, respectively). The samples in upper panels were stained with antisense BikDD probes, and the arrows indicate positive cells. The lower panels showed the negative control experiments stained with sense BikDD probes. In FIG. 17C, the CT90 promoter drives expression of BikDD in comparable level to that from the CMV promoter. MCF7 cells were transfected with CMV-BikDD and CT90-BikDD by electroporation method. After 24 hours, cells in each experiment were harvested and lysed for Western blot.

In FIG. 18A, there are constructs of candidates for pancreatic cancer-specific promoter. CCKAR, orphan G protein-coupled receptor (RDC1), urokinase-type plasminogen activator receptor (uPAR), and chymotrypsinogen B1 (CTRB1) were polymerase chain reaction-amplified and subcloned into the reporter plasmid pGL3-basic, driving a firefly luciferase gene. In FIG. 18B, PANC-1 and AsPC-1 cells were transiently co-transfected with the plasmid DNA indicated and pRL-TK. Forty-eight hours later, the dual luciferase ratio was measured and shown as relative light units (RLU) normalized to the Renilla luciferase control. The data represent the mean of four independent experiments. Bar, SD.

In FIG. 19A, there is a schematic diagram of engineered CCKAR-based constructs including pGL3-CCKAR-Luc-WPRE (CCKAR-P-Luc)), pGL3-CCKAR-TSTA-Luc (CCKAR-T-Luc), and pGL3-CCKAR-TSTA-Luc-WPRE (CTP-Luc). In FIG. 19B, there is activity of CCKAR-based promoters in pancreatic cancer cells. AsPC-1, PANC-1 and PanO2 cells were transiently co-transfected with plasmid DNA and pRL-TK. Forty-eight hours later, the dual luciferase ratio was measured. The percentage relative to the activity of the CMV promoter is shown. The data represent the mean of four independent experiments. In FIG. 19C, there is tissue specificity of CCKAR-based promoter composites. Non-pancreatic cancer (LNCaP, PC-3, SKOV3.ip1, MDA-MB-468, and HeLa), and normal and immortalized (WI-38, 184A1, and E6E7) cell lines were transiently co-transfected with the plasmids indicated and pRL-TK. Forty-eight hours later, the dual luciferase ratio was measured. The percentage relative to the activity in AsPC-1 cells is shown. The data represent the mean of four independent experiments. RLU, relative light units.

In FIG. 20A, there is in vivo imaging of mice. Mice were anesthetized and imaged for 5 min using an IVIS imaging system 10 minutes after intraperitoneal injection of D-luciferin. In FIG. 20B, there is tissue distribution of luciferase expression. Tissue specimens from tumors and organs as shown were dissected and measured for luciferase activity with a luminometer. Data were expressed as relative luciferase units per milligram of total protein. CMV, pGL3-CMV-Luc; CTP, pGL3-CTP-Luc; bar, SD; RLU, relative light units; n=4 mice each group.

In FIG. 21A, there is a schematic diagram of expression constructs in the pUK21 backbone. CMV-BikDD, pUK21-CMV-BikDD; CTP-BikDD, pUK21-CTP-BikDD. In FIG. 21B, the killing effects of BikDD driven by CMV or CTP are provided. A panel of pancreatic cancer (AsPC-1, PANC-1, MDA-Panc28, and PanO2), immortalized human pancreatic epithelial E6E7 cells were co-transfected with 2 µg of pUK21 (negative control), pUK21-CMV-BikDD (positive control), or pUK21-CTP-BikDD, plus 100 ng of pGL3-CMV-Luc. Forty-eight hours after transfection, the luciferase activity was imaged for 2 min using an IVIS imaging system following a 5-minute incubation with 5 ng/ml of D-luciferin. Representative images were shown in the upper panel. The percentage of the signal compared with the negative control (set as 100%) was calculated (lower panel). The data represent the mean of three independent experiments. 1, pUK21; 2, CMV-BikDD; 3, CTP-BikDD; bar, SD.

In FIG. 22A, there is a schematic diagram of reporter constructs. In FIG. 22B, prostate cancer LNCaP and PC-3, and normal human fibroblast WI-38 cells lines were transiently co-transfected with reporter plasmid DNA and the internal control vector pRL-TK. Forty eight hours later, the dual luciferase ratio was measured. Shown are the luciferase activities (folds) in relative to the CMV promoter (setting at 1).

In FIG. 23A, there is a schematic diagram of reporter constructs. In FIG. 23B, cells were transiently co-transfected with reporter plasmid DNA and the internal control vector pRL-TK. Forty eight hours after incubation with R1881, the dual luciferase ratio was measured. Shown are the luciferase activities (folds) in relative to that of the CMV promoter (setting at 1).

In FIG. 24A, mice were then immediately dissected and imaged ex vivo for 2 min. In FIG. 24B, the dissected tumors were then immediately imaged for 10 min (FIG. 24C). In FIG. 24D, ex vivo PC-3 tumors were imaged (as C) after systemic delivery of CMV-Luc or ATTP-Luc plasmid DNA to the PC-3 tumor-bearing mice. The quantitative signal was presented (right). In FIG. 24E, there is in vivo biodistribution of luciferase expression in the LNCaP tumor model. Tissue specimens from tumor and organs as shown were dissected and measured for luciferase activity with a luminometer.

In FIG. 25A, dominant-negative Cdk2 mutant (Cdk2-dn) blocked topoIIα promoter activity in breast cancer cells. The control vector or Cdk2-dn expression vector was cotransfected into cells with the topoIIα-pGL3 reporter vector, and then luciferase assay was performed to determine topoIIα promoter activity. The ratio of topoIIα promoter activity in the Cdk2-dn group to that in the control group was shown. The cell lines used are described above. BC, breast cancer cells. In FIG. 25B, Cyclin A activates the topoIIα promoter in breast cancer cells. The control or cyclin A (CCNA) expression vector was cotransfected into SKBR3 cells with the topoIIα-pGL3 reporter vector, and then the luciferase assay was performed to determine topoIIα promoter activity. The ratio of topoIIα promoter activity in the Cdk2-dn group to that in the control group is shown. In FIG. 25C, the design of topoIIα promoter deletion mutants (−572, −182, −90, −60) and ICB1-mutated topoIIα promoter (mICB1). Circled x, the mutation at ICB1 site. In FIG. 25D, ICB1 can mediate the activation of topoIIα promoter by cyclin A/cdk2 signal in breast cancer cells. Left panel, The topoIIα promoter deletion mutants were cotransfected with the cyclin A expression vector or the control vector into the various cell lines, and their activity was determined by luciferase assay. The ratio of promoter activity in the cyclin A group to that in the control group (CCNA/Ctrl) is shown. Right panel, The ICB1 site of the topoIIα promoter was mutated as described in Materials and Methods. The ICB1-mutated promoter (mICB1-T2A) was cotransfected with the cyclin A expression vector or the control vector into the various cell lines, and the activation were determined as described above. In FIG. 25E, the −90 deletion mutant of topoIIα promoter retains breast cancer-specific activity. Upper panel, The T2A90-pGL3 was transfected into cell lines, and its promoter activity was determined by using the dual luciferase assay. BE, normal breast epithelial cells; BC, breast cancer cells; LF, normal lung fibroblasts; HC, normal hepatocytes; PC, pancreatic cancer cells; OC, ovarian cancer cells. Lower panel, T2A-90 promoter activity relative to that of the CMV promoter in various cell lines. The promoter activity ratio of T2A-90 to CMV (topoIIα/CMV) in each cell line was calculated as described in FIG. 25B.

In FIG. 26A, design of CT572, CT182, and CT90 is provided. The CMV promoter enhancer sequence from the pCDNA3.1 vector was PCR amplified and cloned upstream to the topoIIα −182, or −90 promoters in pGL3 reporter construct, forming the fusion promoters CT572, CT182, and CT90, respectively. In FIG. 26B, there is activity of CT572, CT182, and CT90 in cell lines. The promoter activity in each cell line were determined as described above. FIG. 26C shows activity of CT572, CT182, and CT90 relative to the CMV promoter in cell lines. The promoter activity ratios of CT572 to CMV (CT572/CMV), CT182 to CMV (CT182/CMV), and CT90 to CMV (CT90/CMV) in each cell line were determined as described above. FIG. 26D shows CT90 in vivo activity in MDA-MB-231 orthotopic breast cancer xenograft mouse model. The liposome-complexed luciferase reporter constructs controlled by CT90 (CT90-luc) or CMV promoter (CMV-luc) were injected into tumor-bearing mice by tail vein injection. Mice were killed to remove tumor and major organs 48 hours after injection. Upper panel, absolute values of luciferase activity from the CMV and CT90 promoters in tumor and normal organs. Lower panel, the activity ratio of the CT90 promoter to the CMV promoter (CT90/CMV). All values were calculated as described earlier in FIG. 25B. FIG. 26E shows CT90 activity in MDA-MB-231 breast cancer xenograft mice by intratumoral injection. The CT90-luc or CMV-luc construct complexed with DOTAP:Chol liposome was injected into MDA-MB-231 tumors on mice. Mice were killed to remove tumor and major organs 48 hours after injection. Left panel, absolute values of luciferase activity from the CMV and CT90 promoters in tumor and normal organs. Right panel, the activity ratio of the CT90 promoter to the CMV promoter (CT90/CMV). All values were calculated as described earlier in FIG. 25B.

DETAILED DESCRIPTION OF THE INVENTION

Figure 1:
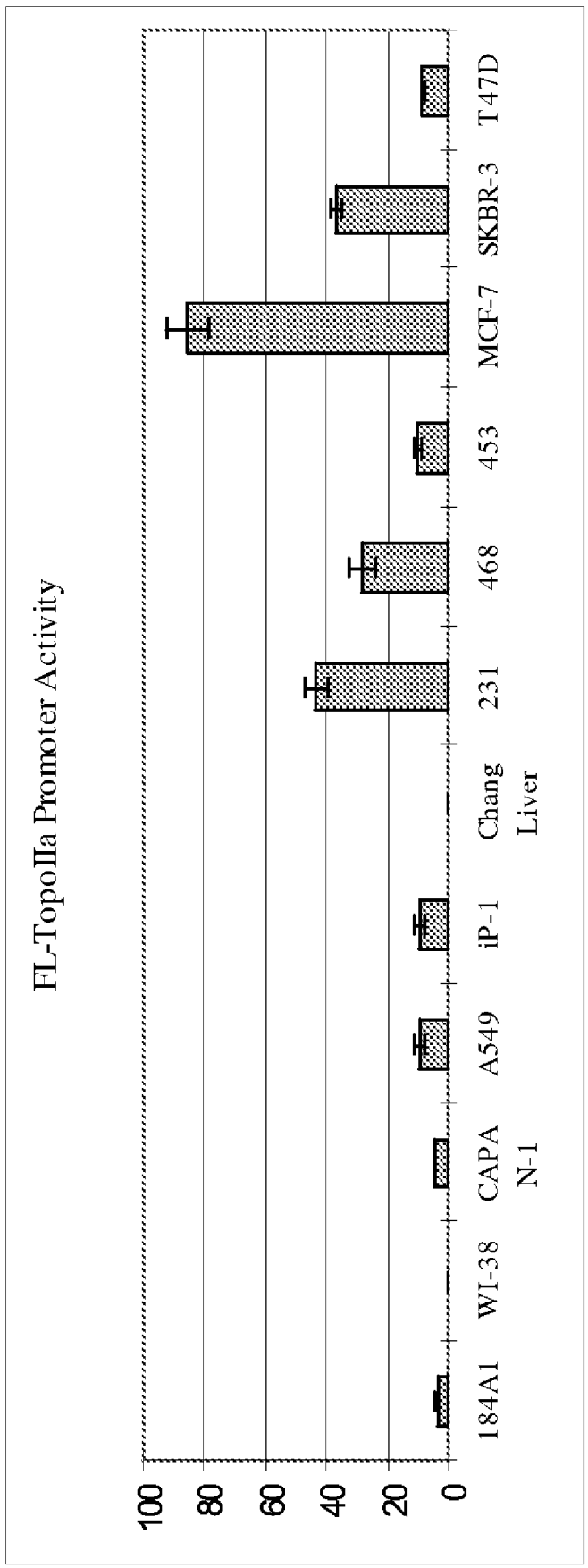
FIG. 1 shows the activity of full-length (FL) topoIIα promoter with luciferase reporter assay in cell lines including normal breast epithelium cell (184A1), normal liver cell (Chang liver), fibroblast (WI38), lung cancer (A549), pancreatic cancer (CAPAN-1), ovarian cancer (iP-1), and breast cancer (MD-MBA-231, MD-MBA-468, MD-MBA-453, SKBR3, T47D, MCF-7) cells.

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" one or more sequences of the invention, for example.

In some embodiments a polynucleotide comprising the inventive control sequences is delivered by, for example, either a viral or non-viral delivery system into an appropriate recipient animal to suppress tumor growth and development. In one exemplary embodiment of the present invention, the delivered therapeutic gene product acts through an apoptosis mechanism to suppress tumor growth and development.

In one aspect of the invention, a therapeutic polypeptide comprised in a construct including a tissue-specific control sequence is administered as a polynucleotide targeted for expression in breast cancer, pancreatic cancer, or prostate cancer, for example. In certain aspects of the invention, a breast cancer-specific promoter controls expression of the therapeutic polynucleotide. As used herein, the term "therapeutic polynucleotide" refers to a polynucleotide that encodes a therapeutic gene product, which may be an RNA, protein, polypeptide, or peptide, for example.

In a specific embodiment, the control sequences of the present invention comprise a composite (chimeric) promoter. For example, breast cancer specific promoters comprised of a CMV promoter enhancer sequence linked with breast cancer specific segments in either topoisomerase IIα promoter (named as CT90) or transferrin receptor promoter (named as CTR116) may be utilized. Both of these chimeric promoters drive gene expression selectively in breast cancer cells and possess activity levels comparable to the CMV promoter. Constructs employing the CT90 or CTR116 chimeric promoters are used in gene transfer to target and treat primary and metastatic breast cancers with less toxicity to normal tissues, preferably by selectively killing breast cancer cells and/or significantly reducing breast tumor growth and/or growth rate.

In other aspects of the invention, a prostate cancer-specific or pancreatic cancer-specific promoter controls expression of a therapeutic polynucleotide. In a particular embodiment of the invention there is a composite prostate cancer-specific or pancreatic cancer-specific. For example, the prostate cancer-specific promoter may comprise an ARR2 control sequence, whereas the pancreatic cancer-specific promoter may comprise a CCKAR control sequence.

Any promoter or control sequence utilized to regulate expression of a therapeutic polynucleotide may utilize specific regulatory sequences that enhance expression and/or post-transcriptional processes, for example. Particular but exemplary sequences include enhancers, a two-step transcriptional amplification system, elements that regulate RNA polyadenylation, half-life, and so forth, such as the WPRE, and/or others in the art.

In other embodiments of the present invention, there are methods of preventing growth of a cell in an individual comprising administering to the individual a construct of the present invention. In specific embodiments, the construct is administered in a liposome and/or the therapeutic gene product may further comprise a protein transduction domain (Schwarze et al., 1999), such as HIV Tat or penetratin, for example. The therapeutic polynucleotide may be administered in a vector such as a plasmid, retroviral vector, adenoviral vector, adeno-associated viral vector, liposome, or a combination thereof, for example.

I. Nucleic Acid-Based Expression Systems

The present invention utilizes, in some embodiments, systems for expressing therapeutic polynucleotides, particularly for cancer treatment. Particular exemplary aspects for these polynucleotides are described herein.

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. In a specific embodiment, a control sequence, such as a promoter, regulates the tissue specificity within which the nucleic acid sequence is expressed. A promoter, or control sequence, may comprise genetic elements at which regulatory proteins and molecules may bind, such as RNA polymerase and other transcription factors. The phrases "operatively positioned," "operatively linked," "under control," and "under transcriptional control" mean that a promoter or other control sequence is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202; U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The identity of tissue-specific promoters or elements, as well as assays to characterize their activity, is well known to those of skill in the art. Tissue-specific promoters utilized to control expression targeting and/or levels of a therapeutic gene product may be comprise wild-type nucleic acid sequence, mutant nucleic acid sequence, or synthetic nucleic acid sequence, so long as the expression of the therapeutic polynucleotide is preferentially retained in one or more tissues of interest compared to tissues that are not the desired target. Control sequences, such as promoters, may be composite sequences, wherein multiple regions are derived from different sources. Synthetic control sequences may be further defined as composite promoters, wherein at least two separate regions originating from different endogenous and/or synthetic promoters yet operably linked to control expression of a therapeutic polynucleotide. In a particular embodiment, the tissue specificity refers to specificity for cancerous tissue, as opposed to non-cancerous tissue. The term "cancerous tissue" as used herein refers to a tissue comprising at least one cancer cell.

a. Breast Cancer Tissue-Specific Promoter

Most of the promoters currently used in cancer gene therapy possess strong but unselective activity (e.g. CMV and β-actin promoters) in both normal and tumor cells. Thus, in some aspects of the present invention, a breast tissue-specific promoter is utilized in the invention, such as to control expression of a therapeutic polynucleotide, including a mutant form of Bik, such as the exemplary BikT33D, BikS35D, and Bik T33DS35D mutants. These Bik mutants are described herein but provided in further detail in U.S. Nonprovisional patent application Ser. No. 10/816,698, entitled "Antitumor Effect of Mutant Bik" by Mien-Chie Hung, Yan Li, and Yong Wen, incorporated by reference herein in its entirety. In a particular aspect, the breast cancer-specific promoter of the present invention targets expression of a polynucleotide encoding a therapeutic gene product specifically to breast cancer tissue.

In one particular embodiment of the present invention, composite promoters utilizing either topoisomerase IIα (topoIIα) and transferrin receptor (TfR) breast cancer-specific control sequences are employed. The topoisomerase IIα (topoIIα) and transferrin receptor (TfR) levels are elevated in breast cancer, as determined using SAGE analysis and cDNA microarray, for example. The present inventors identified a 90 base pair segment (SEQ ID NO:12) and a 116 base pair segment (SEQ ID NO:13) in the 5'-end of topoIIα and TfR promoter, respectively, as a minimally required breast-cancer specific control sequence. As described in the Examples herein, the promoter activity was enhanced by connecting these two short promoters with an enhancer sequence, such as the cytomegalovirus (CMV) promoter enhancer sequence (SEQ ID NO:11); these chimeric promoters are referred to herein as CT90 and CTR116, respectively. The full CT90 promoter is comprised in SEQ ID NO:23, and the full CTR116 promoter is comprised in SEQ ID NO:24.

The CT90 and CTR116 reporter assay in breast cancer cell lines and/or in xenograft mouse models showed that these two promoters possessed not only strong activity, but also specificity for breast cancer tissue and cells therein. In specific embodiments, the promoter activity of CTR116 in cells is further enhanced under hypoxic condition, which usually occurs inside solid tumors. To demonstrate its use in cancer gene therapy, the present inventors generated a DNA construct using CT90 to drive apoptotic gene expression. When transfected into cell lines, this construct selectively killed breast cancer cells. Moreover, the present inventors demonstrated that this construct had an anti-tumor effect on breast tumor xenograft in mouse by intravenous injection with an exemplary non-viral delivery system. This indicates that CT90 can drive the expression of a therapeutic gene, such as mutant Bik, selectively in breast cancer cells.

Regarding tumor specificity, given that most of the current cancer-specific promoters have either pretty weak activity compared to the CMV promoter (e.g. Anderson et al., 2000; Katabi et al., 1999; Lu et al., 2002; Maeda et al., 2001), or insufficient tumor specificity (e.g. CMV-enhanced GAPDH (Qiao et al., 2002), they are not clinically useful. On the contrary, the activities of CT90 and hypoxia-induced CTR116 promoters are comparable to CMV promoter (about 0.5- to 2-fold) while being specific for breast cancer cells. Thus, the current invention encompasses breast cancer-specific promoters for control of expression of mutant Bik to target breast cancer cells for treatment that is less toxic or non-toxic to normal tissues.

b. Pancreatic Cancer Tissue-Specific Promoter

Pancreatic cancer-specific promoters are useful to target pancreatic cancer cells while leaving pancreatic non-cancerous cells unaffected. The present inventors developed strong and pancreatic cancer-specific promoters for targeted expression of polynucleotides encoding therapeutic gene products, including mutant Bik, such as the exemplary BikT33D, BikS35D, and Bik T33DS35D mutants. These Bik mutants are described herein but provided in further detail in U.S. Nonprovisional patent application Ser. No. 10/816,698, entitled "Antitumor Effect of Mutant Bik" by Mien-Chie Hung, Yan Li, and Yong Wen, incorporated by reference herein in its entirety.

However, the present inventors developed a pancreatic cancer-specific promoter as follows. According to literature and the Series Analysis of Gene Expression database of the National Canter for Biotechnology Information, the present inventors preliminarily screened a series of promoters that target genes overexpressed in human pancreatic cancer, including Cholecystoskinin A receptor (CCKAR), orphan G protein-coupled receptor (RDC1), urokinase-type plasminogen activator receptor (uPAR), carboxypeptidase A1 (CPA1) and chymotrypsinogen B1 (CTRB1), for example. These were assayed for control of firefly luciferase expression through luciferase activity in pancreatic cancer cells as well as immortalized normal cells. The CCKAR promoter ranging from nt −726 to +1 (SEQ ID NO:14) was identified as having optimal activity and specificity among these promoters. However, the activity of this minimal CCKAR promoter was much weaker than that of the commonly used CMV enhancer/promoter. The present inventors then engineered a series of composites based on CCKAR promoter by using the exemplary GAL4-VP 16 or GAL4-VP2 fusion protein, referred to as a two-step transcriptional amplification (TSTA) system (Iyer et al., 2001; Zhang et al., 2002; Sato et al., 2003; and references cited therein), to augment the transcriptional activity; the post-transcriptional regulatory element of the woodchuck hepatitis virus (WPRE) (SEQ ID NO:15) was utilized to modify RNA polyadenylation signal, RNA export, and/or RNA translation. A skilled artisan recognizes that the term "two-step transcriptional amplification (TSTA) system" may also be referred to as "two-step transcriptional activation (TSTA) system" or "recombinant transcriptional activation approach" (Nettelbeck et al., 2000). In a particular aspect, the CCKAR-TSTA-WPRE (CTP) promoter is utilized, and an example of such a composite promoter is comprised in SEQ ID NO:20. Thus, the molecularly engineered CTP promoter is employed for effective treatment modalities for pancreatic cancer gene therapy.

The activity of CCKAR promoter was increased 3.9-fold and 820-fold by WPRE and TSTA, respectively. Surprisingly, for combined TSTA and WPRE, the activity of CCAKAR-TSTA-WPRE (CTP) was 0.7-fold in PANC-1 cells and even 2.8-fold in AsPC-1 cells compared to CMV promoter, retaining stringent pancreatic cancer specificity. Further, to determine whether CTP had high activity and strict specificity in vivo after systemic delivery, nu/nu nude mice bearing subcutaneous (s.c) or orthotopic (o.t) pancreatic tumor of AsPC-1 cells were tail-vein-injected once a day for three consecutive days with CTP-Luc or CMC-Luc plasmid DNA-DOTOP:Chol complexes, and in vivo and ex vivo bioluminescently images with a non-invasive IVIS™ Imaging System were obtained. Bioluminescent imaging showed very brilliantly in the areas of thorax (lung/heart) in CMV-Luc injected mice but was almost non-captured in CTP-Luc injected mice. The activity of luciferase, detected with a luminometer, demonstrated 1.4- and 2.0-fold greater activity in the o.t. tumors and s.c. tumors, respectively. The ratio of CTP Luciferase expression level to CMV luciferase expression level is 0.37, 0.006, 0.04, 0.37, 0.63, and 0.19 in pancreas, lung, heart, liver, spleen, and kidney, respectively, in the o.t. model, demonstrating improved tissue specificity. Taken together, molecularly engineered CTP promoter surpasses CMV enhancer/promoter in activity in pancreatic cancer cells and retains its specificity in vitro and in vivo, thereby providing safer and more effective treatment modalities for pancreatic cancer gene therapy.

c. Prostate Cancer Tissue-Specific Promoter

Prostate cancer-specific promoters can be used to control expression of polynucleotides that encode therapeutic gene products, including mutant Bik. These Bik mutants are described herein but provided in further detail in U.S. Nonprovisional patent application Ser. No. 10/816,698, entitled "Antitumor Effect of Mutant Bik" by Mien-Chic Hung, Yan Li, and Yong Wen, incorporated by reference herein in its entirety. The activities of these promoters are androgen-dependent. For numerous disease stages, patients are androgen-dependent (ADPC), allowing the use of androgen-responsive vectors to direct expression of therapeutic genes to prostatic tissue. Although robust prostate-specific promoters responsive to androgen receptor have been developed by the present inventors (Xie et al., Cancer Res 2001) and other groups (Zhang et al., Mol Endocrinol 2000), these androgen-dependent promoters may be less active after castration or androgen ablation therapy, which are the main modalities for progressive prostate cancer treatment. Patients treated with compositions comprising these promoters may fail this kind of therapy and die of recurrent androgen-independent prostate cancer (AIPC).

The inventors have developed novel promoters for gene therapy that will be active in both ADPC and AIPC to treat metastatic and recurrent hormonal refractory prostate cancer. The promoter, referred to herein as ATTP, comprises at least a prostate cell-specific control sequence, such as the exemplary ARR2 regulatory element (SEQ ID NO:17) from ARR2 gene. The promoter may also comprise at least the minimal promoter fragment (hTERTp) of the human telomerase reverse transcriptase (hTERT) (SEQ ID NO:18) operably linked to a two-step transcriptional amplification (TSTA) system, such as the exemplary GAL4-VP16 or GAL4-VP2 (two examples of GAL4-VP2 are comprised in SEQ ID NO:16 or SEQ ID NO:19) fusion protein-encoding sequences. The therapeutic polynucleotide may also be operatively linked to a post-transcriptional control sequence, such as the post-transcriptional regulatory element of the woodchuck hepatitis virus (WPRE) to modify RNA polyadenylation signal, RNA export, and/or RNA translation. These regulatory sequences are effective in both ADPC and AIPC cell lines. Given that in most cases of recurrent prostate cancers the AR gene is amplified and/or AR is overexpressed, this particular promoter greatly improves the effective index for the embodiment wherein the activity of this system is stimulated by androgen. In particular embodiments, the TSTA-hTERT-ARR2 and WPRE elements are utilized as the prostate cancer-specific control sequences, which in specific embodiments are comprised in SEQ ID NO:21.

Toward the generation of this promoter, the minimal promoter fragment (hTERTp) of the human telomerase reverse transcriptase (hTERT) (SEQ ID NO:18) was PCR-amplified from the DNA extracts of LNCaP cells and tested for activity in luciferase reporter system. The hTERTp is active in both LNCaP and PC-3 cells, but its activity was very weak compared to CMV enhancer/promoter. A series of composites based on hTERTp promoter were then engineered by using the GAL4-VP16 or GAL4-VP2 fusion protein through a two-step transcriptional amplification (TSTA) system to augment the transcriptional activity and the post-transcriptional regulatory element of the woodchuck hepatitis virus (WPRE) to modify RNA polyadenylation signal, RNA export, and/or RNA translation. The exemplary GAL4-VP2 fusion protein is encoded by a polynucleotide comprising SEQ ID NO:16 or SEQ ID NO:19.

WPRE increased the activity by about 2-fold. Surprisingly, the TSTA system can boost the activity up to 67% of CMV activity in LNCaP cell and 90% in PC-3 cells. When the TSTA system is utilized in combination with WPRE, the activity is comparable to CMV in PC-3, and is even 1.5-fold higher in LNCaP cells. In contrast, its activity remains silent in lung fibroblast WI-38 cells. This demonstrated that the hTERTp-TSTA-WPRE system works in both ADPC and AIPC cell lines. In most cases of recurrent prostate cancers, the AR gene is amplified and/or AR is overexpressed. Therefore, in specific embodiments it greatly improves the effective index if the activity of this system can be stimulated by androgen.

To accomplish this goal, the ARR2 element (SEQ ID NO:17) derived from plasmid ARR2PB was fused to the hTERTp promoter of phTERTp-TSTA-Luc and phTERTp-TSTA-Luc-WPRE, to produce plasmid pARR2.hTERTp-TSTA-Luc and pARR2.hTERTp-TSTA-Luc-WPRE (ATTP-Luc). As expected, the activity of ARR2.hTERTp-TSTA and ARR2.hTERTp-TSTA-WPRE composites was increased in an androgen-dependent manner, by 15- and 24-fold greater at 10 nm of androgen analog R1881, respectively, than that of CMV in LNCaP cells, without there being a significant change in PC-3 cells.

Thus, the present inventors have developed a novel prostate cancer specific regulatory system that will target polynucleotides that encode therapeutic gene products to not only ADPC but also AIPC.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

5. Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

B. Host Cells

The promoters of the present invention may be used in any manner so long as they regulate expression of a particular polynucleotide. Although they are useful for tissue-specific expression, they are by nature promoters/control sequences and, thus, may be used in any cell environment for expressing any polynucleotide.

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and Solopack™ Gold Cells (Stratagene®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available. Although the promoters of the present invention are useful for tissue-specific expression, they are by nature promoters/control sequences and, thus, may be used in any expression system so long as they regulate expression of a particular polynucleotide.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MaxBac® 2.0 from Invitrogen® and BacPack™ Baculovirus Expression System From Clontech®.

Other examples of expression systems include Stratagene®'s Complete Control™ Inducible Mammalian Expression System, which involves a synthetic ecdysone-inducible receptor, or its pET Expression System, an E. coli expression system. Another example of an inducible expression system is available from Invitrogen®, which carries the T-Rex™ (tetracycline-regulated expression) System, an inducible mammalian expression system that uses the full-length CMV promoter. Invitrogen® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

II. Nucleic Acid Compositions

In certain embodiments of the present invention, particular sequences are employed in the inventive polynucleotide constructs and uses thereof. Although a skilled artisan recognizes that these specific sequences may be employed exactly as provided herein, in other embodiments sequences that are similar to those exemplary sequences provided herein are useful at least in part for tissue-specific cancer regulatory sequences.

Certain embodiments of the present invention concern a tissue-specific regulatory nucleic acid (which may interchangeably be used with the term "polynucleotide"). In other aspects, an expression construct nucleic acid comprises a nucleic acid segment of the exemplary SEQ ID NO:12, SEQ ID NO:13, SEQ ID NO:17, SEQ ID NO:18, or a biologically functional equivalent thereof.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

1. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moeities comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like.

A nucleobase may be comprised in a nucleoside or nucleotide, using any chemical or natural synthesis method described herein or known to one of ordinary skill in the art.

2. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

3. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

4. Nucleic Acid Analogs

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as fluorescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moeity which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moiety replacing phosphodiester backbone moiety used for improved nuclease resistance, cellular uptake and regulating RNA expression; U.S. Pat. No. 5,858,988 which describes hydrophobic carrier agent attached to the 2'-O position of oligonuceotides to enhanced their membrane permeability and stability; U.S. Pat. No. 5,214,136 which describes oligonucleotides conjugaged to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154 which describes RNA linked to a DNA to form a DNA-RNA hybrid.

5. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

6. Purification of Nucleic Acids

A nucleic acid may be purified on polyacrylamide gels, cesium chloride centrifugation gradients, or by any other means known to one of ordinary skill in the art (see for example, Sambrook et al., 1989, incorporated herein by reference).

In certain aspect, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

7. Nucleic Acid Segments

In certain embodiments, the nucleic acid is a nucleic acid segment. As used herein, the term "nucleic acid segment," are smaller fragments of a nucleic acid, such as for non-limiting example, those that comprise only part of the regulatory sequences for a given transcribed polynucleotide.

8. Nucleic Acid Complements

The present invention also encompasses a nucleic acid that is complementary to a nucleic acid of the invention. In particular embodiments the invention encompasses a nucleic acid or a nucleic acid segment complementary to the sequence set forth in SEQ ID NO:12, SEQ ID NO:13, SEQ ID NO:17, and SEQ ID NO:18, for example. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

9. Hybridization

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). As used herein, a "nucleic acid construct" is a nucleic acid engineered or altered by the hand of man, and generally comprises one or more nucleic acid sequences organized by the hand of man.

In a non-limiting example, one or more nucleic acid constructs may be prepared that include a contiguous stretch of nucleotides identical to or complementary to SEQ ID NO:12, SEQ ID NO:13, SEQ ID NO:17, or SEQ ID NO:18, for example. A nucleic acid construct may be about 3, about 5, about 8, about 10 to about 14, or about 15, about 20, about 30, about 40, about 50, about 100, about 200, about 500, about 1,000, about 2,000, about 3,000, about 5,000, about 10,000, about 15,000, about 20,000, about 30,000, about 50,000, about 100,000, about 250,000, about 500,000, about 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges", as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, etc.; about 1,001, about 1002, etc; about 50,001, about 50,002, etc; about 750,001, about 750,002, etc.; about 1,000,001, about 1,000, 002, etc. Non-limiting examples of intermediate ranges include about 3 to about 32, about 150 to about 500,001, about 3,032 to about 7,145, about 5,000 to about 15,000, about 20,007 to about 1,000,003, etc.

The term "a sequence essentially as set forth in SEQ ID NO:12" or "a sequence essentially as set forth in SEQ ID NO:13", for example, means that the sequence substantially corresponds to a portion of SEQ ID NO:12 and SEQ ID NO:13 and has relatively few nucleotides that are not identical to, or a biologically functional equivalent of, the respective nucleotides of SEQ ID NO:12 and/or SEQ ID NO:13. Thus, "a sequence essentially as set forth in SEQ ID NO:12" or "a sequence essentially as set forth in SEQ ID NO:13" encompasses nucleic acids, nucleic acid segments, and genes that comprise part or all of the nucleic acid sequences as set forth in SEQ ID NO:12 and/or SEQ ID NO:13.

The term "biologically functional equivalent" is well understood in the art and is further defined in detail herein. Accordingly, a sequence that has between about 70% and about 80%; or more preferably, between about 81% and about 90%; or even more preferably, between about 91% and about 99%; of nucleotides that are identical or functionally equivalent to the nucleotides of sequences referred to herein, such as the exemplary SEQ ID NO:12, SEQ ID NO:13, SEQ ID NO:17 or SEQ ID NO:18 will be a sequence that is respectively "essentially as set forth in the SEQ ID NO:12, SEQ ID NO:13, SEQ ID NO:17 or SEQ ID NO:18", provided the biological activity of the sequences is maintained.

In certain other embodiments, the invention concerns at least one recombinant vector that include within its sequence a nucleic acid sequence essentially as set forth in SEQ ID NO:12, SEQ ID NO:13, SEQ ID NO:17, or SEQ ID NO:18.

III. Therapeutic Polynucleotides

The therapeutic polynucleotide which expression is controlled by the inventive control sequences encompassed by the invention may be of any kind, so long as the gene product encoded thereby generates an anticancer effect. Anticancer effects include inducing apoptosis in at least one cancer cell, inhibiting proliferation of at least one cancer cell, ameliorating at least once symptom of cancer in an individual, and so forth. In particular embodiments, the therapeutic polynucleotide encodes a mutant form of Bik, including the exemplary BikT33D, BikS35D, and Bik T33DS35D mutants, which are described in U.S. patent application Ser. No. 10/816,698, incorporated by reference herein in its entirety.

The therapeutic polynucleotide may be of any kind known to those of skill in the art or discovered later. In particular embodiments, they encode inhibitors of cellular proliferation, regulators of programmed cell death, tumor suppressors and/or antisense sequences of inducers of cellular proliferation. The therapeutic polynucleotide may encode small interfering RNAs or antisense sequences. Examples of therapeutic polynucleotides include those encoding TNFα or p53 or that encode polypeptide inducers of apoptosis including, but not limited to, Bik, p53, Bax, Bak, Bcl-x, Bad, Bim, Bok, Bid, Harakiri, Ad E1B, Bad and ICE-CED3 proteases. Other exemplary therapeutic polynucleotides include those that encode retinoblastoma, Blk, IL-12, IL-10, IFN-a, cytosine deaminase, GM-CSF, E1A, and other pro-apoptotic proteins, for example. A polynucleotide encoding an amino acid substitution at threonine 33, serine 35, or both of mutant Bik may be utilized. In particular aspects of these embodiments, the amino acids of the mutant Bik polypeptide are substituted with aspartate. In other particular aspects, one or more phosphorylation sites are defective in a mutant Bik. Additional therapeutic polynucleotides include TNFα or p53 or inducers of apoptosis including, but not limited to, Bik, p53, Bax, Bak, Bcl-x, Bad, Bim, Bok, Bid, Harakiri, Ad E1B, Bad and ICE-CED3 proteases.

IV. Nucleic Acid Delivery

The general approach to the aspects of the present invention concerning compositions and/or therapeutics is to provide a cell with a gene construct encoding a specific and/or desired mutant Bik protein, polypeptide, or peptide, thereby permitting the desired activity of the protein, polypeptide, or peptide to take effect. While it is conceivable that the gene construct and/or protein may be delivered directly, a preferred embodiment involves providing a nucleic acid encoding a specific and desired protein, polypeptide, or peptide to the cell. Following this provision, the proteinaceous composition is synthesized by the transcriptional and translational machinery of the cell, as well as any that may be provided by the expression construct. In providing antisense, ribozymes and other inhibitors, the preferred mode is also to provide a nucleic acid encoding the construct to the cell.

In certain embodiments of the invention, the nucleic acid encoding the gene may be stably integrated into the genome of the cell. In yet further embodiments, the nucleic acid may be stably maintained in the cell as a separate, episomal segment of DNA. Such nucleic acid segments and "episomes" encode sequences sufficient to permit maintenance and replication independent of and in synchronization with the host cell cycle. How the expression construct is delivered to a cell and/or where in the cell the nucleic acid remains is dependent on the type of expression construct employed.

A. DNA Delivery Using Viral Vectors

The ability of certain viruses to infect cells and enter cells via receptor-mediated endocytosis, and to integrate into host cell genome and/or express viral genes stably and/or efficiently have made them attractive candidates for the transfer of foreign genes into mammalian cells. Preferred gene therapy vectors of the present invention will generally be viral vectors.

Although some viruses that can accept foreign genetic material are limited in the number of nucleotides they can accommodate and/or in the range of cells they infect, these viruses have been demonstrated to successfully effect gene expression. However, adenoviruses do not integrate their genetic material into the host genome and/or therefore do not require host replication for gene expression, making them ideally suited for rapid, efficient, heterologous gene expression. Techniques for preparing replication-defective infective viruses are well known in the art.

Of course, in using viral delivery systems, one will desire to purify the virion sufficiently to render it essentially free of undesirable contaminants, such as defective interfering viral particles and endotoxins and other pyrogens such that it will not cause any untoward reactions in the cell, animal and/or individual receiving the vector construct. A preferred means of purifying the vector involves the use of buoyant density gradients, such as cesium chloride gradient centrifugation.

1. Adenoviral Vectors

A particular method for delivery of the expression constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and/or (b) to ultimately express a tissue and/or cell-specific construct that has been cloned therein.

The expression vector comprises a genetically engineered form of adenovirus. Knowledge of the genetic organization and adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and/or no genome rearrangement has been detected after extensive amplification.

Adenovirus is particularly suitable for use as a gene transfer vector because of its mid-sized genome, ease of manipulation, high titer, wide target-cell range and/or high infectivity. Both ends of the viral genome contain 100-200 base pair inverted repeats (ITRs), which are cis elements necessary for viral DNA replication and/or packaging. The early (E) and/or late (L) regions of the genome contain different transcription units that are divided by the onset of viral DNA replication. The E1 region (E1A and/or E1B) encodes proteins responsible for the regulation of transcription of the viral genome and/or a few cellular genes. The expression of the E2 region (E2A and/or E2B) results in the synthesis of the proteins for viral DNA replication. These proteins are involved in DNA replication, late gene expression and/or host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and/or all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and/or examine its genomic structure.

Generation and/or propagation of the current adenovirus vectors, which are replication deficient, depend on a unique helper cell line, designated 293, which was transformed from human embryonic kidney cells by Ad5 DNA fragments and constitutively expresses E1 proteins (E1A and/or E1B; Graham et al., 1977). Since the E3 region is dispensable from the adenovirus genome (Jones and Shenk, 1978), the current adenovirus vectors, with the help of 293 cells, carry foreign DNA in either the E1, the D3 and both regions (Graham and Prevec, 1991). Recently, adenoviral vectors comprising deletions in the E4 region have been described (U.S. Pat. No. 5,670,488, incorporated herein by reference).

In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and/or E3 regions, the maximum capacity of the current adenovirus vector is under 7.5 kb, and/or about 15% of the total length of the vector. More than 80% of the adenovirus viral genome remains in the vector backbone.

Helper cell lines may be derived from human cells such as human embryonic kidney cells, muscle cells, hematopoietic cells and other human embryonic mesenchymal and epithelial cells. Alternatively, the helper cells may be derived from the cells of other mammalian species that are permissive for human adenovirus. Such cells include, e.g., Vero cells and other monkey embryonic mesenchymal and/or epithelial cells. As stated above, the preferred helper cell line is 293.

Recently, Racher et al. (1995) disclosed improved methods for culturing 293 cells and/or propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcaniers (Bibby Sterlin, Stone, UK) (5 g/l) is employed as follows. A cell inoculum, resuspended in 5 ml of medium, is added to the carrier (50 ml) in a 250 ml Erlenmeyer flask and/or left stationary, with occasional agitation, for 1 to 4 h. The medium is then replaced with 50 ml of fresh medium and/or shaking initiated. For virus production, cells are allowed to grow to about 80% confluence, after which time the medium is replaced (to 25% of the final volume) and/or adenovirus added at an MOI of 0.05. Cultures are left stationary overnight, following which the volume is increased to 100% and/or shaking commenced for another 72 h.

Other than the requirement that the adenovirus vector be replication defective, and at least conditionally defective, the nature of the adenovirus vector is not believed to be crucial to the successful practice of the invention. The adenovirus may be of any of the 42 different known serotypes and subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) and in the E4 region where a helper cell line and helper virus complements the E4 defect.

Adenovirus growth and/or manipulation is known to those of skill in the art, and/or exhibits broad host range in vitro and in vivo. This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and/or therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991a; Stratford-Perricaudet et al., 1991b; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and/or stereotactic inoculation into the brain (Le Gal La Salle et al., 1993). Recombinant adenovirus and adeno-associated virus (see below) can both infect and transduce non-dividing human primary cells.

2. AAV Vectors

Adeno-associated virus (AAV) is an attractive vector system for use in the cell transduction of the present invention as it has a high frequency of integration and it can infect nondividing cells, thus making it useful for delivery of genes into mammalian cells, for example, in tissue culture (Muzyczka, 1992) and in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. No. 5,139,941 and/or U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and/or in vivo transduction of marker genes (Kaplitt et al., 1994; Lebkowski et al., 1988; Samulski et al., 1989; Yoder et al., 1994; Zhou et al., 1994; Hermonat and Muzyczka, 1984; Tratschin et al., 1985; McLaughlin et al., 1988) and genes involved in human diseases (Flotte et al., 1992; Luo et al., 1994; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus and a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome and from a recombinant plasmid, and/or a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and/or an expression plasmid containing the wild type AAV coding sequences without the terminal repeats, for example pIM45 (McCarty et al., 1991; incorporated herein by reference). The cells are also infected and transfected with adenovirus and plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions and cell lines containing the AAV coding regions and some and all of the adenovirus helper genes could be used (Yang et al., 1994; Clark et al., 1995). Cell lines carrying the rAAV DNA as an integrated provirus can also be used (Flotte et al., 1995).

3. Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and/or directs synthesis of viral proteins. The integration results in the retention of the viral gene sequences in the recipient cell and/or its descendants. The retroviral genome contains three genes, gag, pol, and/or env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and/or stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Gene delivery using second generation retroviral vectors has been reported. Kasahara et al. (1994) prepared an engineered variant of the Moloney murine leukemia virus, that normally infects only mouse cells, and modified an envelope protein so that the virus specifically bound to, and infected, human cells bearing the erythropoietin (EPO) receptor. This was achieved by inserting a portion of the EPO sequence into an envelope protein to create a chimeric protein with a new binding specificity.

4. Other Viral Vectors

Other viral vectors may be employed as expression constructs in the present invention. Vectors derived from viruses such as vaccinia virus (Ridgeway, 1988; Baichwal and Sugden, 1986; Coupar et al., 1988), sindbis virus, cytomegalovirus and/or herpes simplex virus may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and/or pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In certain further embodiments, the gene therapy vector will be HSV. A factor that makes HSV an attractive vector is the size and organization of the genome. Because HSV is large, incorporation of multiple genes and expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and/or can be grown to high titers. Thus, delivery is less of a problem, both in terms of volumes needed to attain sufficient MOI and in a lessened need for repeat dosings.

5. Modified Viruses

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and/or against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

B. Other Methods of DNA Delivery

In various embodiments of the invention, DNA is delivered to a cell as an expression construct. In order to effect expression of a gene construct, the expression construct must be delivered into a cell. As described herein, the preferred mechanism for delivery is via viral infection, where the expression construct is encapsidated in an infectious viral particle. However, several non-viral methods for the transfer of expression constructs into cells also are contemplated by the present invention. In one embodiment of the present invention, the expression construct may consist only of naked recombinant DNA and/or plasmids. Transfer of the construct may be performed by any of the methods mentioned which physically and/or chemically permeabilize the cell membrane. Some of these techniques may be successfully adapted for in vivo and/or ex vivo use, as discussed below.

C. Liposome-Mediated Transfection

In a further embodiment of the invention, the expression construct may be entrapped in a liposome. Liposomes are vesicular structures characterized by a phospholipid bilayer membrane and/or an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and/or entrap water and/or dissolved solutes between the lipid bilayers (Ghosh and Bachhawat, 1991). Also contemplated is an expression construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and/or expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and/or promote cell entry of liposome-encapsulated DNA (Kaneda et al., 1989). In other embodiments, the liposome may be complexed and/or employed in conjunction with nuclear non-histone chromosomal proteins (HMG-1) (Kato et al., 1991). In yet further embodiments, the liposome may be complexed and/or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

The inventors contemplate that neu-suppressing gene products can be introduced into cells using liposome-mediated gene transfer. It is proposed that such constructs can be coupled with liposomes and directly introduced via a catheter, as described by Nabel et al. (1990). By employing these methods, the neu-suppressing gene products can be expressed efficiently at a specific site in vivo, not just the liver and spleen cells which are accessible via intravenous injection. Therefore, this invention also encompasses compositions of DNA constructs encoding a neu-suppressing gene product formulated as a DNA/liposome complex and methods of using such constructs.

As described in U.S. Pat. No. 5,641,484, liposomes are particularly well suited for the treatment of HER2/neu-mediated cancer.

Catatonic liposomes that are efficient transfection reagents for Bik for animal cells can be prepared using the method of Gao et al. (1991). Gao et al. describes a novel catatonic cholesterol derivative that can be synthesized in a single step. Liposomes made of this lipid are reportedly more efficient in transfection and less toxic to treated cells than those made with the reagent Lipofectin. These lipids are a mixture of DC-Chol ("3☐(N-(N'N'-dimethylaminoethane)-carbamoyl cholesterol") and DOPE ("dioleoylphosphatidylethanolamine"). The steps in producing these liposomes are as follows.

DC-Chol is synthesized by a simple reaction from cholesteryl chloroformate and N,N-Dimethylethylenediamine. A solution of cholesteryl chloroformate (2.25 g, 5 mmol in 5 ml dry chloroform) is added dropwise to a solution of excess N,N-Dimethylethylenediamine (2 ml, 18.2 mmol in 3 ml dry chloroform) at 0° C. Following removal of the solvent by evaporation, the residue is purified by recrystallization in absolute ethanol at 4° C. and dried in vacuo. The yield is a white powder of DC-Chol.

Cationic liposomes are prepared by mixing 1.2 μmol of DC-Chol and 8.0 μmol of DOPE in chloroform. This mixture is then dried, vacuum desiccated, and resuspended in 1 ml sterol 20 mM Hepes buffer (pH 7.8) in a tube. After 24 hours of hydration at 4° C., the dispersion is sonicated for 5-10 minutes in a sonicator form liposomes with an average diameter of 150-200 nm.

To prepare a liposome/DNA complex, the inventors use the following steps. The DNA to be transfected is placed in DMEM/F12 medium in a ratio of 15 μg DNA to 50 μl DMEM/F12. DMEM/F12 is then used to dilute the DC-Chol/DOPE liposome mixture to a ratio of 50 μl DMEZM/F12 to 100 μl liposome. The DNA dilution and the liposome dilution are then gently mixed, and incubated at 37° C. for 10 minutes. Following incubation, the DNA/liposome complex is ready for injection.

Liposomal transfection can be via liposomes composed of, for example, phosphatidylcholine (PC), phosphatidylserine (PS), cholesterol (Chol), N-[1-(2,3-dioleyloxy)propyl]-N,N-trimethylammonium chloride (DOTMA), dioleoylphosphatidylethanolamine (DOPE), and/or 3.beta.[N-(N'N'-dimethylaminoethane)-carbamoyl cholesterol (DC-Chol), as well as other lipids known to those of skill in the art. Those of skill in the art will recognize that there are a variety of liposomal transfection techniques that will be useful in the present invention. Among these techniques are those described in Nicolau et al., 1987, Nabel et al., 1990, and Gao et al., 1991. In a specific embodiment, the liposomes comprise DC-Chol. More particularly, the inventors the liposomes comprise DC-Chol and DOPE that have been prepared following the teaching of Gao et al. (1991) in the manner described in the Preferred Embodiments Section. The inventors also anticipate utility for liposomes comprised of DOTMA, such as those that are available commercially under the trademark Lipofectin™, from Vical, Inc., in San Diego, Calif.

Liposomes may be introduced into contact with cells to be transfected by a variety of methods. In cell culture, the liposome-DNA complex can simply be dispersed in the cell culture solution. For application in vivo, liposome-DNA complex are typically injected. Intravenous injection allow liposome-mediated transfer of DNA complex, for example, the liver and the spleen. In order to allow transfection of DNA into cells that are not accessible through intravenous injection, it is possible to directly inject the liposome-DNA complexes into a specific location in an animal's body. For example, Nabel et al. teach injection via a catheter into the arterial wall. In another example, the inventors have used intraperitoneal injection to allow for gene transfer into mice.

The present invention also contemplates compositions comprising a liposomal complex. This liposomal complex will comprise a lipid component and a DNA segment encoding a nucleic acid encoding a mutant form of Bik. The nucleic acid encoding the mutant form of Bik employed in the liposomal complex can be, for example, one that encodes Bik-T145A or Bik-T145D.

The lipid employed to make the liposomal complex can be any of the above-discussed lipids. In particular, DOTMA, DOPE, and/or DC-Chol may form all or part of the liposomal complex. The inventors have had particular success with complexes comprising DC-Chol. In a preferred embodiment, the lipid will comprise DC-Chol and DOPE. While any ratio of DC-Chol to DOPE is anticipated to have utility, it is anticipated that those comprising a ratio of DC-Chol:DOPE between 1:20 and 20:1 will be particularly advantageous. The inventors have found that liposomes prepared from a ratio of DC-Chol:DOPE of about 1:10 to about 1:5 have been useful.

In a specific embodiment, one employs the smallest region needed to enhance retention of Bik in the nucleus of a cell so that one is not introducing unnecessary DNA into cells which receive a Bik gene construct. Techniques well known to those of skill in the art, such as the use of restriction enzymes, will allow for the generation of small regions of Bik. The ability of these regions to inhibit neu can easily be determined by the assays reported in the Examples.

In certain embodiments of the invention, the liposome may be complexed with a hemagglutinatin virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

D. Electroporation

In certain embodiments of the present invention, the expression construct is introduced into the cell via electroporation. Electroporation involves the exposure of a suspension of cells and/or DNA to a high-voltage electric discharge.

Transfection of eukaryotic cells using electroporation has been quite successful. Mouse pre-B lymphocytes have been transfected with human kappa-immunoglobulin genes (Potter et al., 1984), and/or rat hepatocytes have been transfected with the chloramphenicol acetyltransferase gene (Tur-Kaspa et al., 1986) in this manner.

E. Calcium Phosphate and/or DEAE-Dextran

In other embodiments of the present invention, the expression construct is introduced to the cells using calcium phosphate precipitation. HumanKB cells have been transfected with adenovirus 5 DNA (Graham and Van Der Eb, 1973) using this technique. Also in this manner, mouse L(A9), mouse C127, CHO, CV-1, BHK, NIH3T3 and/or HeLa cells were transfected with a neomycin marker gene (Chen and Okayama, 1987), and/or rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and/or erythroleukemia cells (Gopal, 1985).

F. Particle Bombardment

Another embodiment of the invention for transferring a naked DNA expression construct into cells may involve particle bombardment. This method depends on the ability to accelerate DNA-coated microprojectiles to a high velocity allowing them to pierce cell membranes and/or enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten and/or gold beads.

G. Direct Microinjection and/or Sonication Loading

Further embodiments of the present invention include the introduction of the expression construct by direct microinjection and/or sonication loading. Direct microinjection has been used to introduce nucleic acid constructs into *Xenopus* oocytes (Harland and Weintraub, 1985), and/or LTK-fibroblasts have been transfected with the thymidine kinase gene by sonication loading (Fechheimer et al., 1987).

H. Adenoviral Assisted Transfection

In certain embodiments of the present invention, the expression construct is introduced into the cell using adenovirus assisted transfection. Increased transfection efficiencies have been reported in cell systems using adenovirus coupled systems (Kelleher and Vos, 1994; Cotten et al., 1992; Curiel, 1994).

V. Combination Treatments

In order to increase the effectiveness of a therapeutic gene product encoded by a construct comprising a promoter of the invention, it may be desirable to combine these compositions with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Therapy with the methods and compositions of the present invention can be used in conjunction with chemotherapeutic, radiotherapeutic, immunotherapeutic therapy, surgery, hormonal therapy, or additional gene therapy with other pro-apoptotic or cell cycle regulating agents. Gene therapy with the inventive promoters and/or gene therapy in addition to the inventive compositions and methods may utilize inducers of cellular proliferation; antisense sequences for inducers of cellular proliferation; inhibitors of cellular proliferation, such as p53, p16, Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, Bik/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) or MCC; and/or regulators of programmed cell death, such as those that counteract Bcl-2 function and promote cell death (e.g., Bax, Bak, Bik, Bim, Bid, Bad, Harakiri).

VI. Pharmaceutical Preparations

Pharmaceutical compositions of the present invention comprise an effective amount of a construct comprising control sequences of the present invention that regulate expression of a therapeutic gene product and, in specific embodiment one or more additional agents, dissolved or dispersed in a pharmaceutically acceptable carrier or excipient. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one construct comprising the inventive control sequences that regulate expression of a therapeutic polynucleotide and, in some embodiments one or more additional active ingredients, will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated. In a specific embodiment, the mutant Bik composition is administered in a liposome.

The therapeutic construct comprising the tissue-specific control sequences may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, intraperitoneally, subcutaneously, intravesicularlly, mucosally, intrapericardially, orally, topically, locally, using aerosol, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The therapeutic construct may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols, mouthwashes, or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the Bik mutant form is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, mouthwashes, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Breast Cancer Tissue-Specific Expression

Current breast cancer (BC) therapies, such as chemotherapy (CT) and radiotherapy have low selectivity for tumor cells and side effects for normal tissues. To minimize the side effects, these therapies are generally given in an intermittent manner, allowing normal cells to recover between treatment cycles. However, during the recovery period, some surviving cancer cells become more resistant to the treatment because of gene mutation. Consequently, cancer recurrence or progression may occur. Tumor-targeting gene therapy can minimize treatment side effects and the risk of developing resistance by acting on the tumor-specific signaling pathways. In the present invention, breast cancer-specific promoters are used for breast cancer-targeting gene therapy of the exemplary therapeutic polynucleotide, mutant Bik.

The tumorigenesis and progression of breast cancer involve a series of genetic changes. The specifically activated genes in tumors are good targets of therapies. As the first step, the present inventors collected and reviewed published data from cDNA microarray and SAGE, and identified six genes specifically upregulated in breast cancer cells as shown in Table 1.

TABLE 1

Genes upregulated specifically in breast cancer cells.

| Gene | T/N | PCI (Max = −0.4) |
|---|---|---|
| Transferrin receptor | >20 | −0.3 |
| B-Myb | >20 | ND |
| Ceruloplasmin | >10 | −0.35 |
| X-box Binding protein 1 | >8 | ND |
| γ-glutamyl hydrolase conjugase | >20 | −0.33 |
| Topoisomerase IIα | >20 | ND |

T/N, gene expression ratio of tumor to normal cells. PCI, prognostic correlation index. The negative value of PCI indicates worse prognosis. The maximum value of negative PCI is −0.4.

Among them, the promoters of transferrin receptor (TR), B-Myb, ceruloplasmin, and topoisomerase IIα (topoIIα) were subcloned into luciferase reporter vectors and tested using reporter assays with normal and cancer cell lines. TopoIIα and TR promoters have the highest activity in breast cancer cells relative to normal breast epithelial 184A1 cells.

Therefore, the present inventors further pursued breast cancer-specific cis-elements in these two promoters.

TopoIIα catalyzes topological changes of DNA to release its tension generated during replication, transcription, and chromosome segregation. It is also the target of several anti-cancer agents, such as anthracyclines (e.g. etoposide and doxorubicin). Many studies have shown that topoIIα level correlates with the sensitivity of cancer cells to anthracyclines. In addition, topoIIα is a poor prognostic marker for breast cancer, brain tumors, hepatoma, etc. The regulation of topoIIα expression is strictly cell cycle-dependent: its mRNA level and promoter activity are very low at G0/G1 phase, begin to rise in late S phase, and reach peak at G2/M phase. TopoIIα is a TATA-less promoter containing five Inverted CCAAT Boxes (ICB) and two GC boxes. It is regulated by heat shock, cell cycle stages and p53. NF-Y (also known as CBF) binds to ICBs in the promoter and is required for topoIIα transcription during cell cycle. Taken together, this indicates that the topoIIα promoter responds to oncogenic signaling, in some embodiments, and ICB sites and their binding factors could play a very important role in its BC-specific activity.

In one embodiment of the present invention, transferrin receptor is utilized in composite promoters for the present invention. TR is a membrane receptor that interacts with iron-bound transferrin, facilitating the transport of iron across the cell membrane. A higher TR mRNA level correlates with poor differentiation, greater invasiveness, and high proliferative index of breast cancer cells. In vitro studies have demonstrated that antisense oligonucleotide targeting TR mRNA can specifically inhibit the growth of human breast cancer cells without affecting normal breast cells, indicating TR plays a crucial role in breast cancer development. Even though regulation in mRNA stability is the primary determinant of TR expression in normal cells, many studies revealed that TR transcription is highly activated in proliferating cells and by several oncogenic signals. The core region of TR promoter contains a TATA box, GC box, AP-1/CRE site, and HRE, which responds to hypoxia. Signals like proliferation, hypoxia, iron shortage, and differentiation can activate this segment of TR promoter.

As shown below, the present inventors utilized these exemplary breast cancer-specific CT90 and CTR116 promoters in conjunction with a polynucleotide encoding a mutant Bik polypeptide, in particular embodiments comprised in liposomes. The exemplary CT90-driving BikDD therapeutic vector (CT90-BikDD) selectively killed BC cells in vitro and suppressed the growth of breast tumor xenograft in a mouse model. Taken together, these results indicated that CT90 and CTR116 are effective, strong breast cancer-specific promoters that are useful to control mutant Bik gene expression in breast cancer-targeting gene therapy.

Identification of Core BC-Specific Segments in topoIIα Promoter

Figure 2:
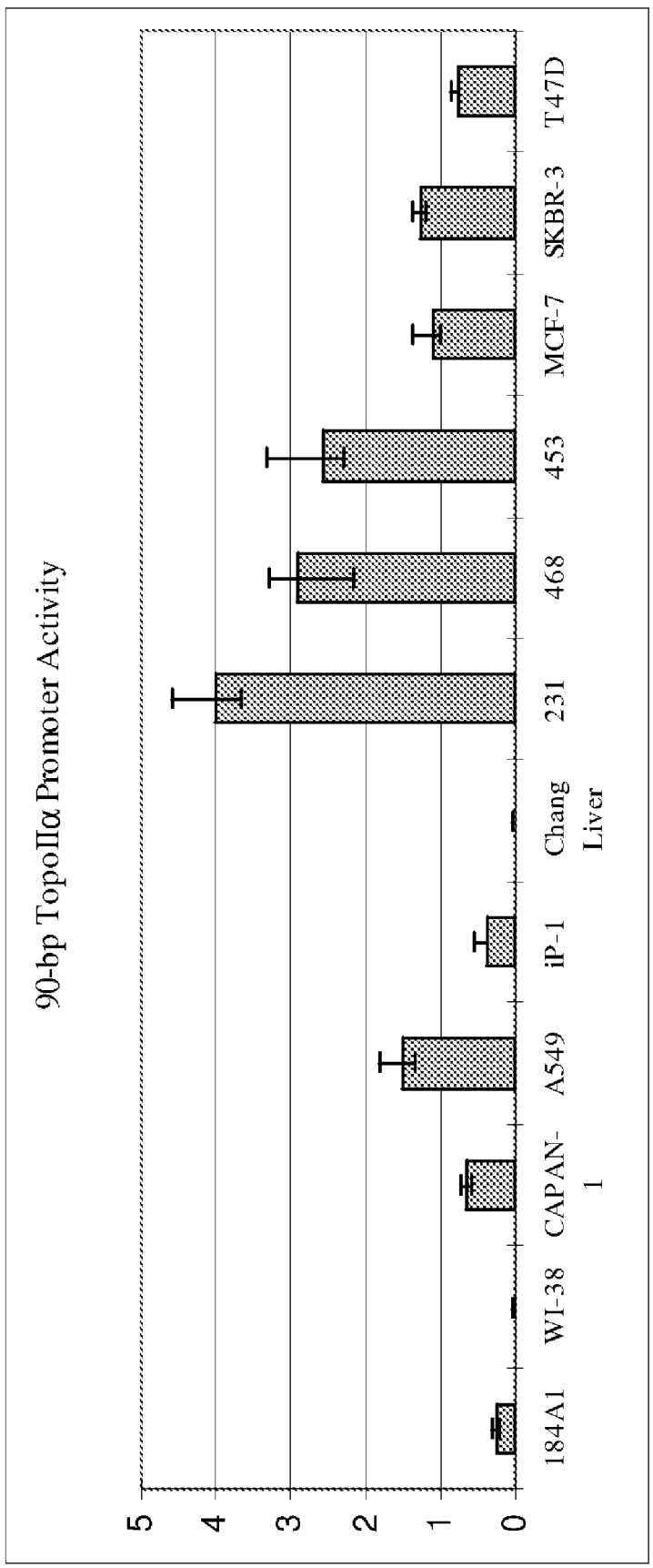
FIG. 2 demonstrates the activity of full-length (FL) topoIIα promoter with luciferase reporter assay in cell lines described in FIG. 10.

To identify one or more segments comprising the cis-elements required for its breast cancer-specificity, the present inventors generated a series of topoIIα promoter deletion mutants by, for example, polymerase chain reaction (PCR). Each mutant contained different number of ICB site(s) ranging from one to five and was subcloned into luciferase expression vector. These reporter constructs were then transiently transfected in various cell lines, and their promoter activities were examined using a luciferase reporter assay. A 580-bp (referred to as full-length) promoter had the highest activity among all the deletion mutants and was activated mostly in breast cancer cells (FIG. 1). However, the shortest promoter segment, which spanned 90 base pairs from the transcription start site and comprised the first ICB site, possessed minimal promoter activity and still retained breast cancer specificity (FIG. 2). This result indicated that the 90-bp segment comprised core breast cancer-specific elements.

Enhancement of topoIIα Promoter Activity with CMV Enhancer Sequence

Figure 3:
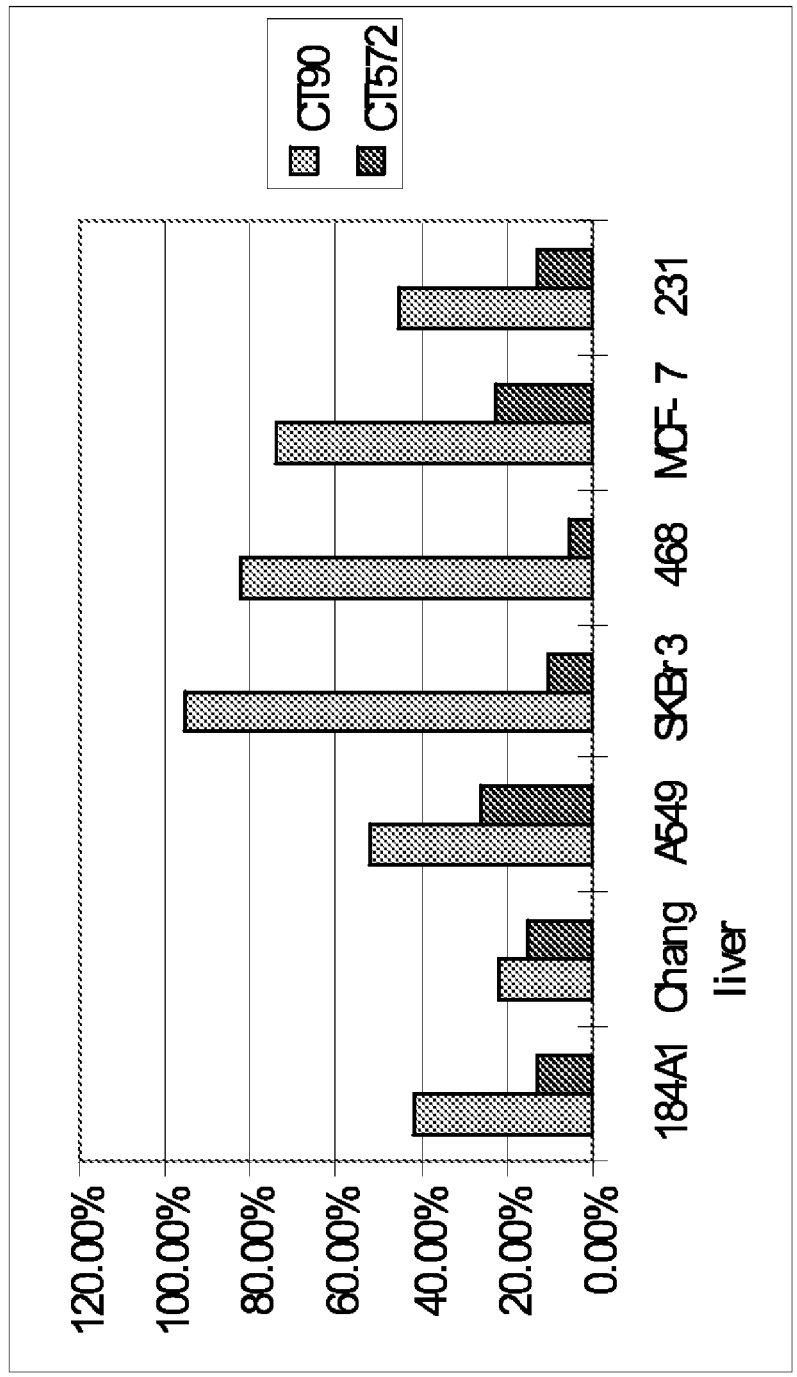
FIG. 3 shows in vitro luciferase expression between CT572 and CT90 in different cell lines by transient transfection, % means compared with the luciferase activity of CMV-PGL3 vector in individual cell line.
Figure 4:
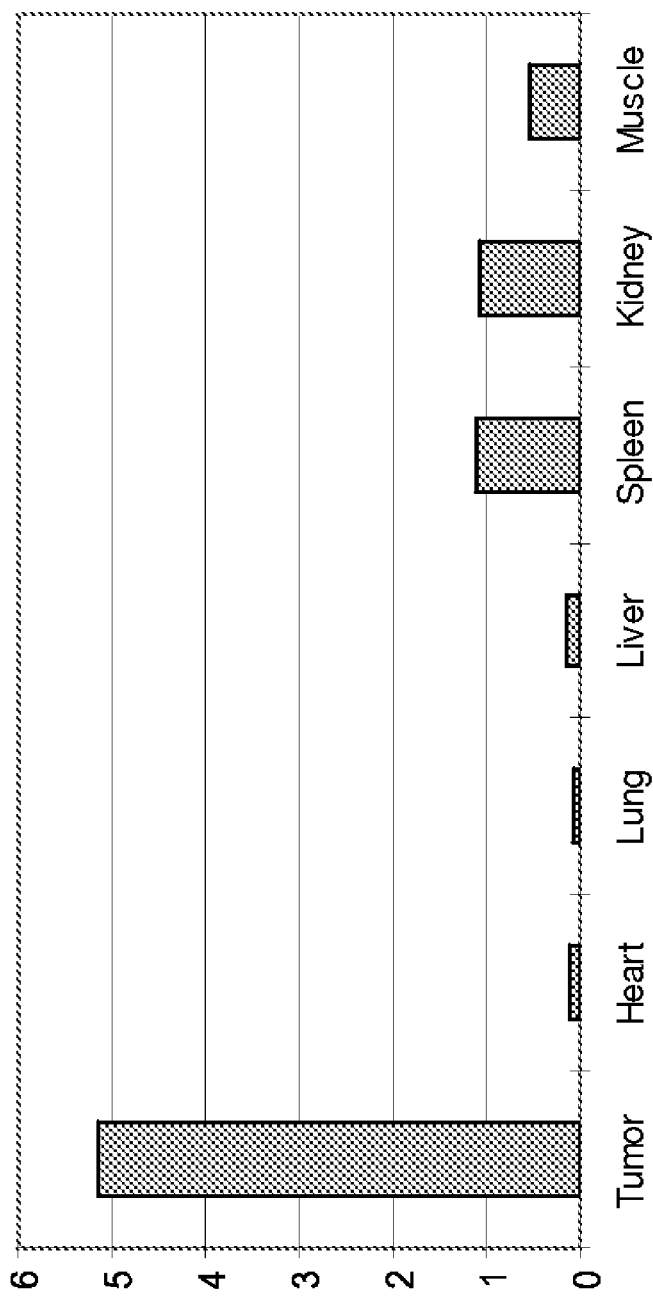
FIG. 4 demonstrates the CT90 promoter activity relative to CMV promoter (CT90/CMV) in tissues of MDA-MB-231 tumor-bearing mice. The promoter activity in each tissue was determined in luciferase reporter assay as described in the text.

The activities of all the topoIIα promoter deletion mutants were as low as less than 10% of CMV promoter activity. To enhance the promoter activity for clinical application, the present inventors obtained the exemplary CMV enhancer sequence from the pCDNA3.1 plasmid by PCR, connected it directly upstream of the full-length and 90-bp topoIIα promoter deletion mutants, and then subcloned it into luciferase reporter vectors. Two exemplary composite promoters were referred to as CT572 and CT90, respectively. Compared to the original promoter deletion mutants, the activity of CT572 and CT90 was dramatically elevated and comparable to the CMV promoter, but still retained their breast cancer specificity (FIG. 3). CT90 promoter has a much higher activity than CT572, and it is nearly strong as the CMV promoter in some cell lines (FIG. 3). Therefore, CT90 was utilized for the in vivo test. Breast cancer MDA-MB-231 cells were inoculated into mammary fat pad of nude mice. Four weeks after inoculation, each mouse in the experiment group received 50 μg of liposome-complexed CT90-luciferase vector delivered by intravenous injection from tail vein, and CMV-luciferase vector was given to mice in the control group. Forty-eight hours after injection, the mice were sacrificed, and the promoter activity was examined by a luciferase assay in tumor, heart, lung, liver, spleen, kidney, and muscle (FIG. 4). CT90 had higher activity than CMV promoter in tumor. However, in normal tissues, the activity of CT90 was much lower than the CMV promoter. This indicated that the CT90 promoter has BC-specific activity in vivo.

Anti-Tumor Effect of CT90-BikDD

Figure 5:
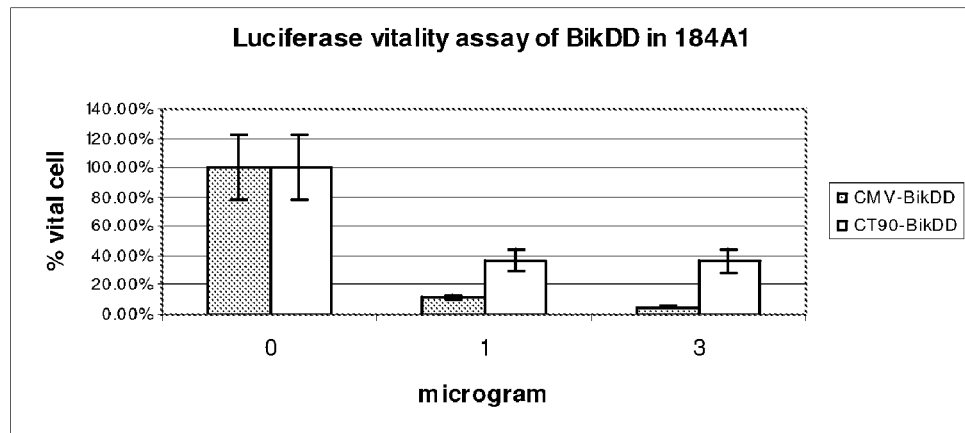
FIG. 5 shows in vitro killing assay of CT90BikDD and CMV-BikDD in different cell lines. The Y-axis value indicates the percentage of vital cells after treatment.
Figure 5:
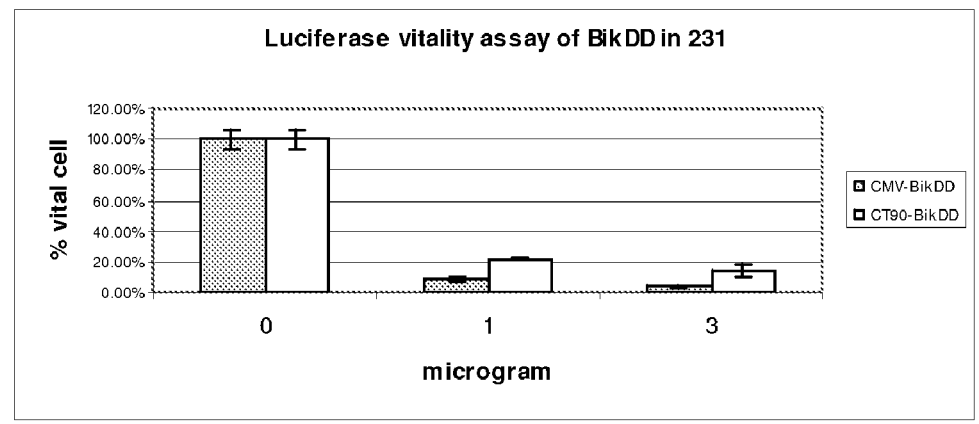
Figure 5:
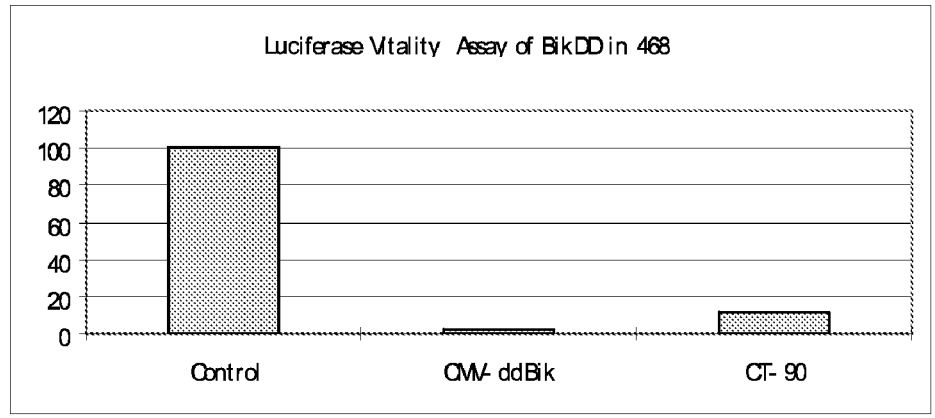

To characterize CT90 in breast cancer-targeting gene therapy, a therapeutic construct in which CT90 drives BikDD expression was generated and is hereinafter referred to as CT90-BikDD. This construct was co-transfected with a luciferase reporter vector into breast cancer cell lines MDA-MB-231 and 468, and the normal breast epithelium cell line 184A1, and then the cell-killing effect was determined by a luciferase vitality assay. The CMV promoter-drivin BikDD vector (CMV-BikDD) and empty vector were used as positive and negative controls, respectively. While CMV-BikDD killed all three cell lines to a nearly equal extent, CT90-BikDD killed breast cancer cells preferentially (FIG. 5), indicating that the killing effect of CT90-BikDD is selective for breast cancer cells. Therefore, CT90 is useful in the breast cancer-targeting gene therapy.

Figure 6:
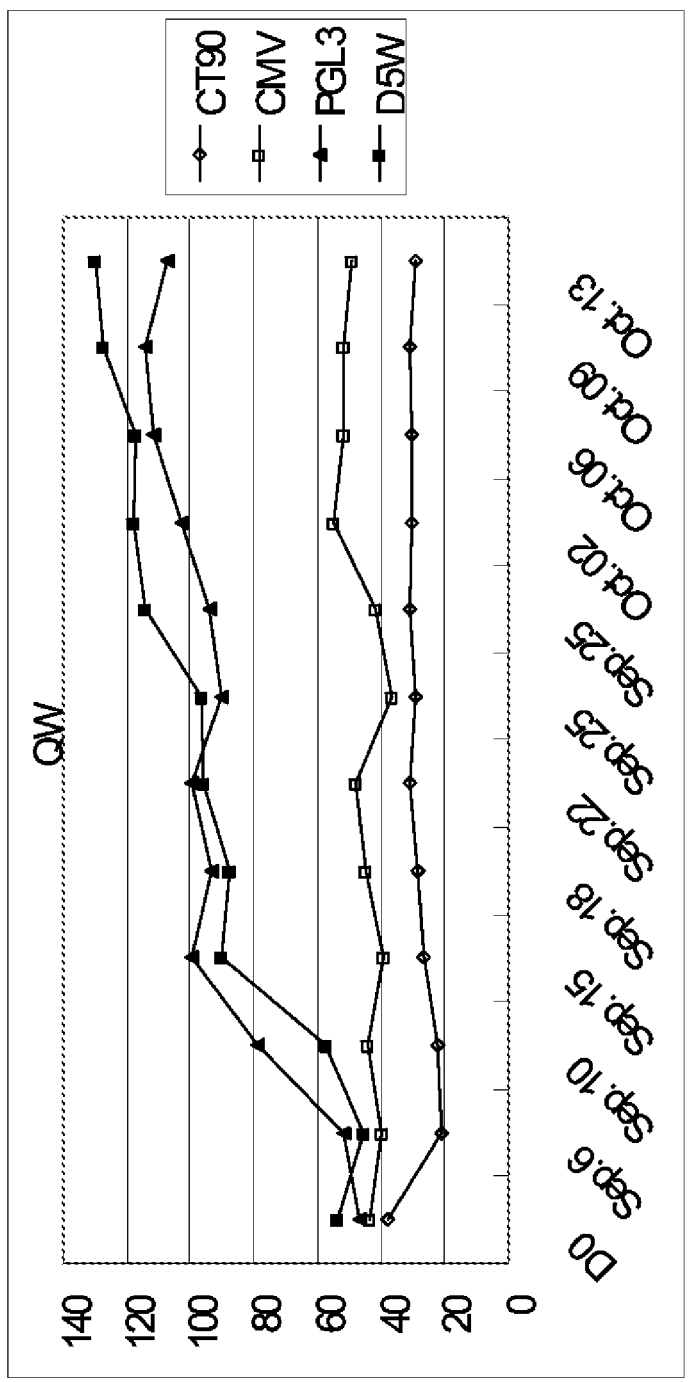
FIG. 6 shows in vivo anti-tumor effect of CT90-BikDD gene therapy. Breast cancer cell line MDA-MB-231 was inoculated $2.5 \times 10^6$ per mouse and mice were treated once per week by liposome-complexed CT0-BikDD, CMV-BikDD, empty vector pGL3, and dextrose buffer D5W as no-treatment control. Tumor size (Y-axis value) was measured twice per week during treatment and showed in the figure. The X-axis indicates the treatment dates.

Next, the anti-tumor effect of this breast cancer-targeting gene therapy was characterized in vivo. One week after inoculating breast cancer MDA-MB-231 cells into mammary fat pads, the nude mice were treated once per week with liposome-complexed CT90-BikDD (therapeutic group), CMV-BikDD (positive control), and CMV-PGL3 (mock treatment), or dextrose buffer D5W as a no-treatment control. Each mouse was intravenously injected with 15 μg of liposome-complexed DNA construct, once per week, and tumor size was measured regularly. The CT90-BikDD group showed a superior tumor suppressive effect compared to CMV-BikDD or CMV-PGL3 (FIG. 6).

Figure 7:
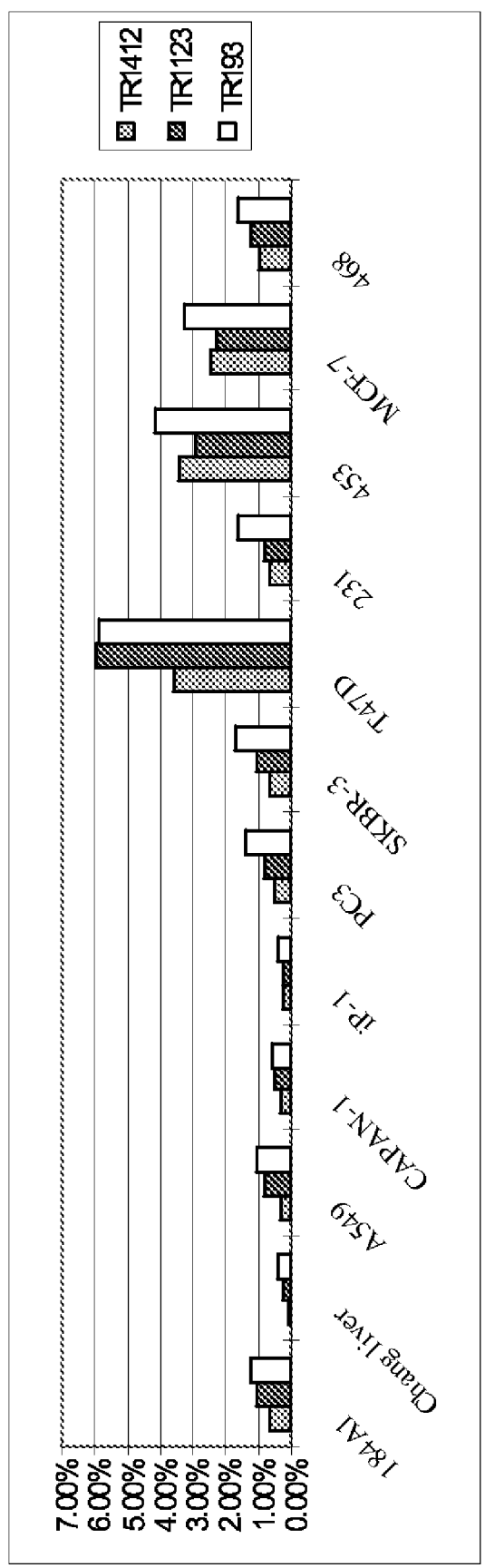
FIG. 7 shows promoter activities of TR deletion mutants normalized by CMV promoter activity in each cell line. The percentage in Y-axis indicates the ratio of TfR promoters over CMV promoter in individual cell lines.

Identification of Core Breast Cancer-Specific Segments in Transferrin Receptor Promoter To identify the segment containing the cis-elements required for its breast cancer-specificity, a series of TR promoter deletion mutants (1412-, 1123-, and 193-bp upstream to the transcription starting site) were generated by PCR and subcloned into a luciferase expression vector. These reporter constructs were then transiently transfected in various cell lines as mentioned above, and their promoter activities were examined using a luciferase reporter assay. The 193-bp segment (187 bp upstream to the transcriptional starting site) had the highest activity and breast cancer specificity in vitro (FIG. 7).

Enhancement of TR Core Promoter Activity with CMV Enhancer Sequence

Figure 8:
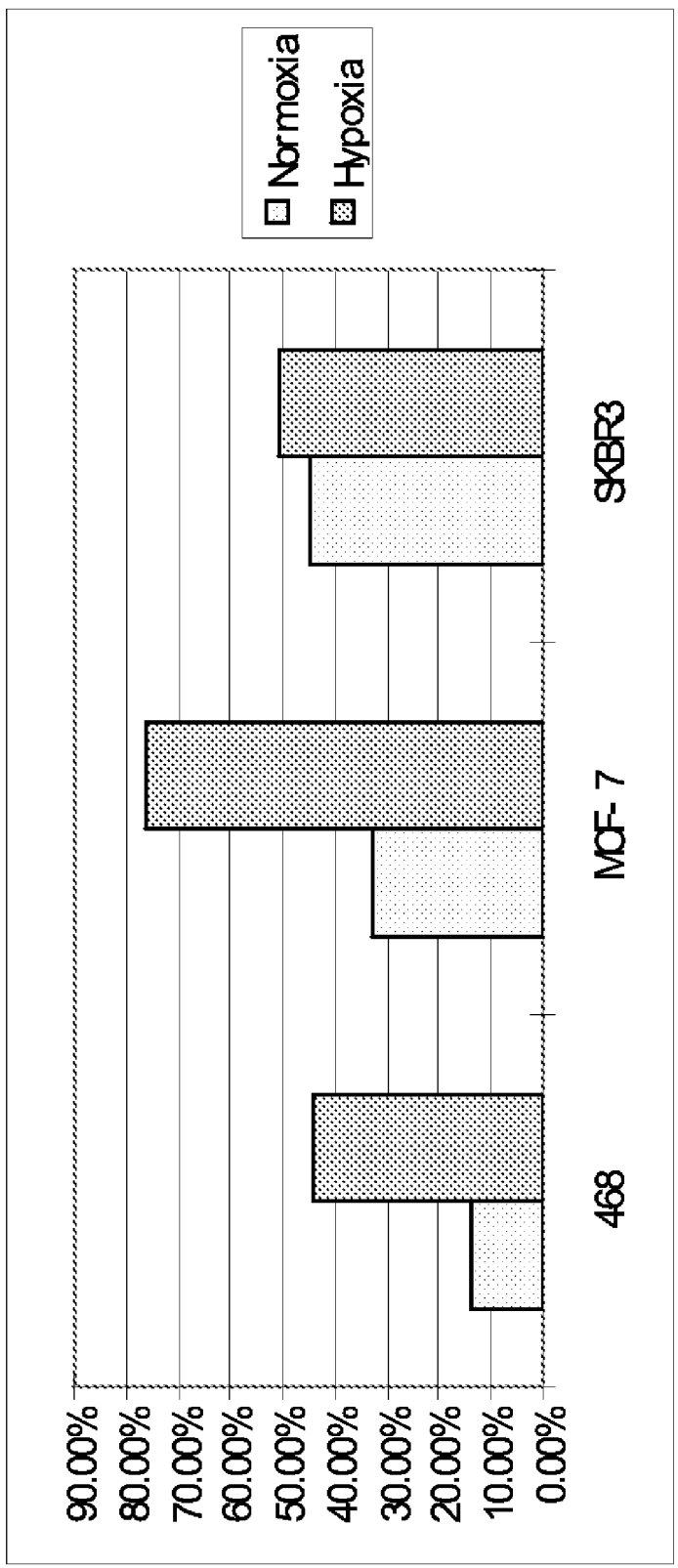
FIG. 8 shows promoter activity of CTR116 normalized by CMV promoter activity in breast cancer cell lines under normoxic and hypoxic condition. The percentage in Y-axis indicated the ratio of TfR116 over CMV promoter activity.

To narrow down the range to a core breast cancer-specific promoter, the 5'-end of the 193-bp segment of the TR promoter was further deleted 116-bp upstream of the transcription start site and connected to a CMV enhancer sequence, as described above for CT90. This composite promoter, herein referred to as CTR116, was subcloned into a luciferase reporter vector and transfected into the cell lines. After transfection, the cells were treated with normoxic or hypoxic conditions (94% $N_2$, 5% $CO_2$, 1% $O_2$ for 20 hours), and the promoter activity of CTR116 was determined by a luciferase assay. Compared to the original deletion mutant promoter, the activity of CTR116 was clearly elevated while retaining its breast cancer specificity. Moreover, its activity can be further induced by hypoxic treatment to become comparable to CMV promoter (FIG. 8). This is the first demonstration that at least part of the TR promoter possesses breast cancer specificity, and a CMV promoter enhancer can enhance its activity without interfering with hypoxia induction.

In further embodiments of the present invention, the respective CT90 and CTR116 elements are narrowed further to identify even smaller segments within that retain breast cancer-specific expression activity. For example, deletion constructs may be made of these respective regions, and their tissue specificity is tested to identify the smaller segments that maintain the ability to direct expression in breast cancer tissue.

Figure 14:
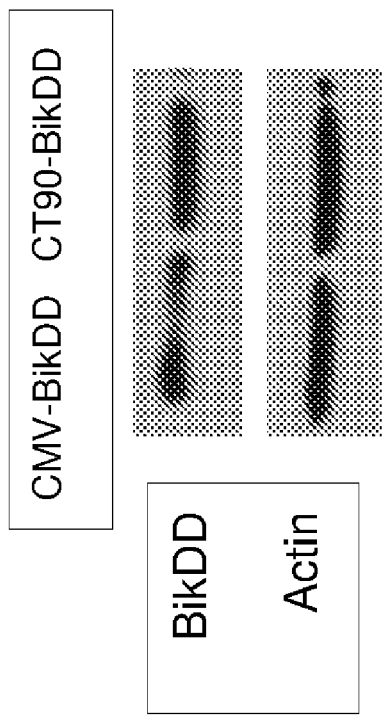
FIG. 14 provides that the CT90 promoter drives expression of BikDD in comparable level to that from the CMV promoter. MCF7 cells were transfected with CMV-BikDD and CT90-BikDD by electroporation method. After 24 hours, cells in each experiment were harvested and lysed for Western blot.

The CT90 Promoter Drives Expression of BikDD in Comparable Level to that from the CMV Promoter To further characterize the activity of the CT90 promoter for inducing gene expression at a similar level as the CMV promoter, which possesses strong activity and is widely used in systemic gene therapy, CT90-BikDD or CMV-BikDD construct were transfected into MCF-7 breast cancer cells by electroporation. 24 hours after transfection, the cells were harvested and lysed for Western blot. As shown in FIG. 14, the expression level of BikDD protein from the CT90 promoter is slightly higher than that from the CMV promoter. This result indicates the CT90 promoter possesses strong activity in breast cancer cells.

Figure 15:
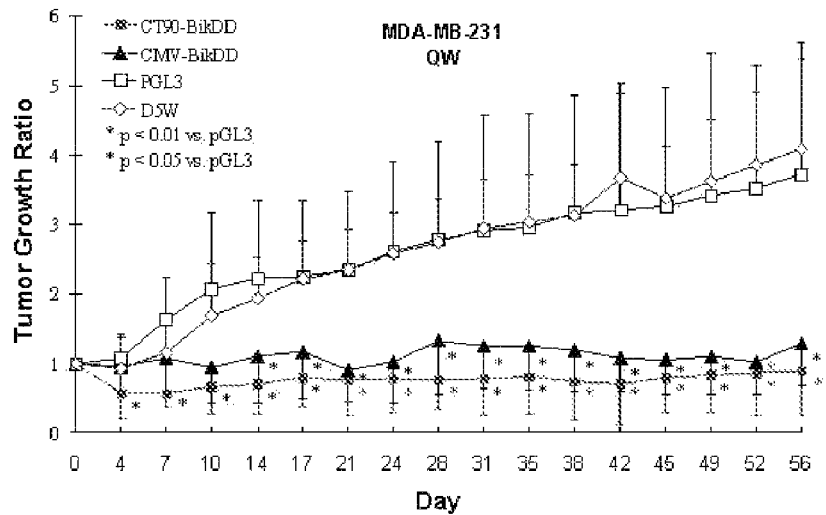
FIG. 15 shows tumor growth during gene therapy treatment. Mice carrying MDA-MB-231 (15A) or MDA-MB-468 (15B) breast cancer xenografts received treatment with 15 μg of lipoplex of CT90-BikDD, CMV-BikDD, empty vector pGL3, or 5% dextrose in water by intravenous injection. Each treatment group had 10 mice. The mice were treated once a week (QW) for 8 weeks, and the tumor size was measured twice a week.
Figure 15:
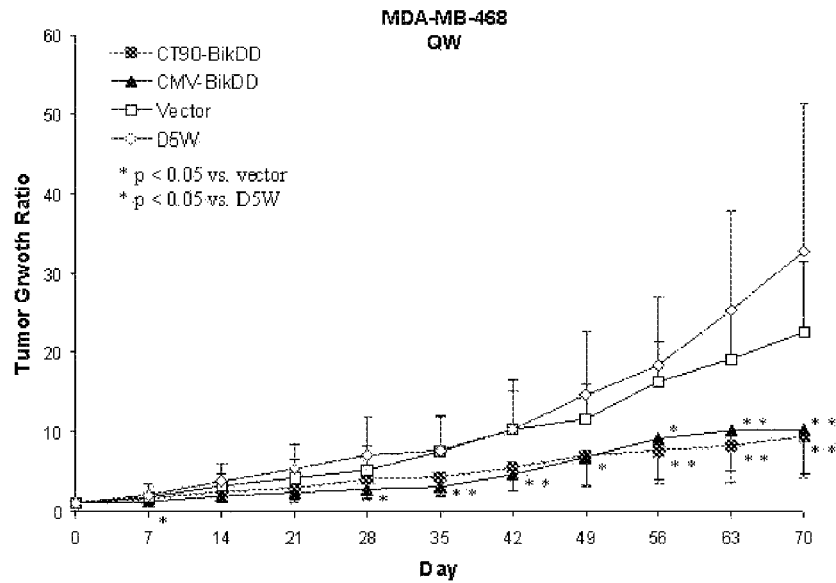
Figure 16:
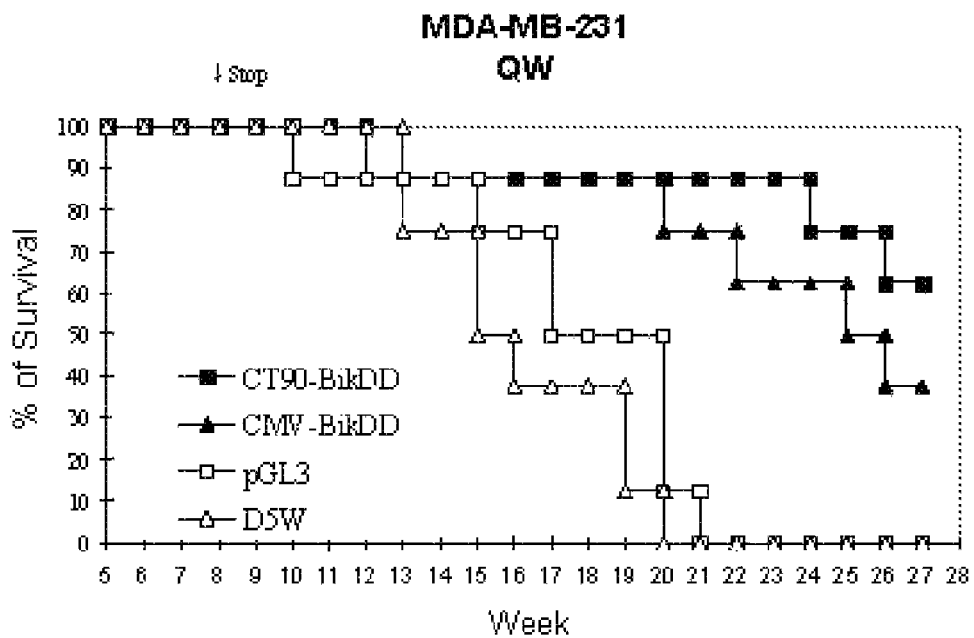
FIG. 16 provides survival records of MDA-MB-231 breast tumor-bearing mice. The treatment was stopped in the eighth week, and the mice were kept alive until reaching morbid status defined by institute regulations. The survival number for each week was recorded and shown in the upper panel. The mean survival time and statistical significance from the Kaplan-Meier analysis and log-rank test are shown in the lower panel. N.S., not significant.

CT90-BikDD Lipoplex Selectively Suppressed Breast Tumor Growth and Prolonged Survival in an Orthotopic Mouse Model To characterize whether systemically delivered liposome-complexed CT90-BikDD (CT90-BikDD lipoplex) could direct selective BikDD expression in vivo, MDA-MB-231 (FIG. 15A) or MDA-MB-468 cells (FIG. 15B) were inoculated in the mammary fat pad of female nude mice to form breast tumors. The tumor bearing mice were then received treatments of liposome-delivered CT90-BikDD, CMV-BikDD, pGL3 vector (mock treatment), or no treatment (D5W), with 8 mice in each treatment group. Lipoplex of different DNA constructs was intravenously injected to mice in the corresponding treatment groups once per week. The tumor growth in CT90-BikDD and CMV-BikDD treatment groups was suppressed significantly ($p<0.05$ in T-test) compared with results in both mock treatment (pGL3) and no treatment (D5W) groups (FIGS. 15A and 15B). As shown in FIG. 15, the mean survival time of mice in CT90-BikDD, CMV-BikDD, pGL3, and D5W groups are 25.25±1.83, 23.25±1.74, 17.5±1.3 and 16.25±0.98 weeks, respectively. Both CT90-BikDD and CMV-BikDD treatments yield significant survival benefit for MDA-MB-231 xenograft-bearing mice compared to the no treatment (D5W) or mock treatment (pGL3) group, indicating that CT90-BikDD provided comparable therapeutic effect as CMV-BikDD (FIG. 16, lower panel).

Figure 17:
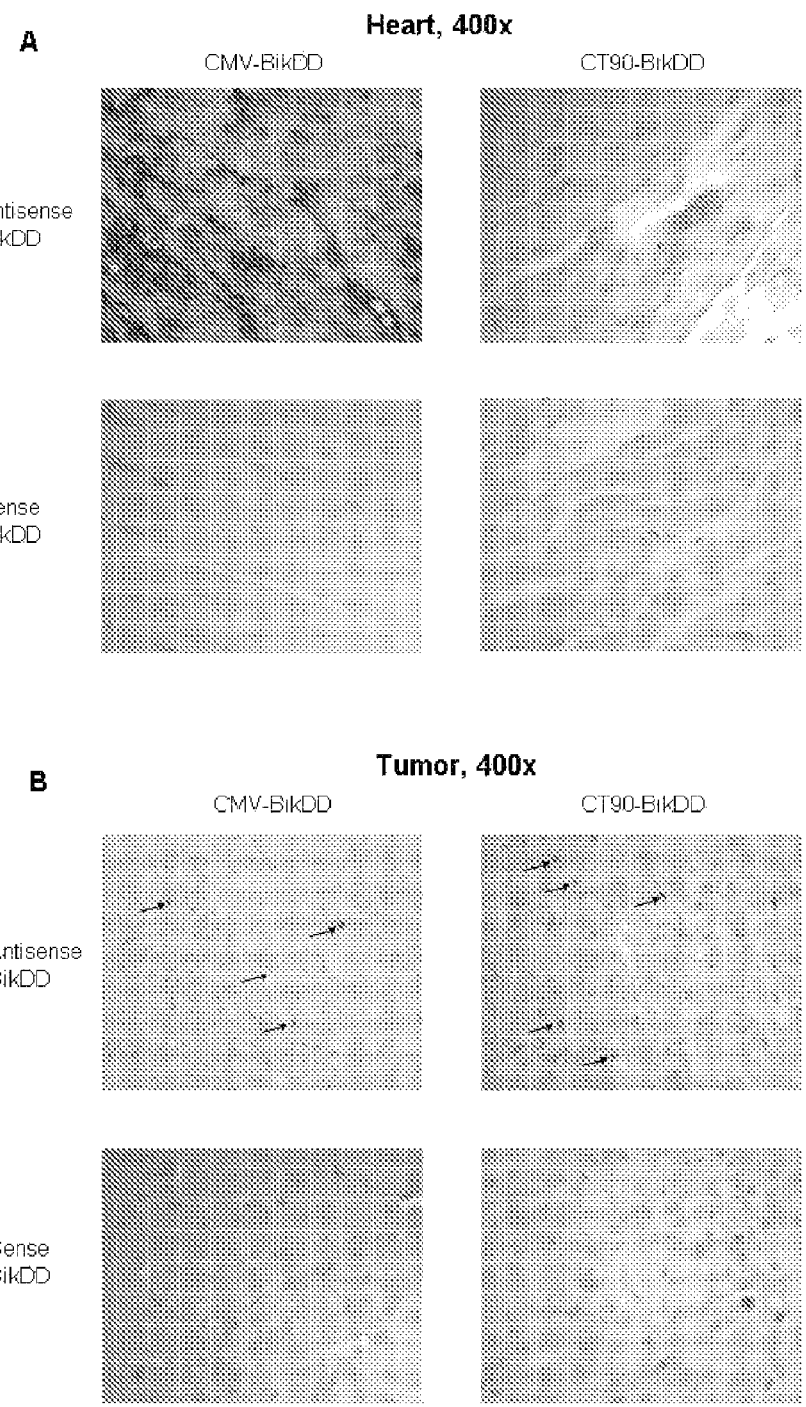
FIG. 17 demonstrates CT90-BikDD directed selective expression of Bik in breast cancer cells in vivo. CT90-BikDD or CMV-BikDD lipoplex was injected into mice carrying MDA-MB-468 breast cancer xenograft. The mice were sacrificed 72 hours after injection, and tumor and heart were removed and fixed. In situ hybridization was performed on the tissue sections to detect BikDD mRNA expression as described in Material and Methods. Shown are representative slides of heart and tumor.

CT90-BikDD Possesses Anti-Tumor Activity and Minimum Side Effect in Normal Tissues The present inventors then further characterize whether the in vivo differential expression profile of CT90-luc and CMV-luc could be reflected by CT90-BikDD and CMV-BikDD. To address this issue, expression of BikDD mRNA in tumor and heart was examined by in situ hybridization (FIG. 17). The deep brown staining all over the heart tissue from a CMV-BikDD-treated mouse indicated a very high expression level of BikDD from CMV promoter (FIG. 17A, upper left panel). On the contrary, CT90-BikDD treatment induced relatively weak BikDD expression in the heart tissues (FIG. 17A, upper right panel). No significant difference in the density and expression level could be detected between the tumor specimens from CT90-BikDD and CMV-BikDD group (FIG. 17B). The negative control using sense BikDD showed no brown staining in these experiments (FIGS. 17A and 17B, lower panels), indicating that the positive signals in the antisense groups came from BikDD expression. These data demonstrate that systemically administrated CT90-BikDD lipoplex can direct the selective BikDD expression in breast tumor. Importantly, expression of BikDD in the normal organ such as heart is much lower in the CT90-BikDD-treated mice than CMV-BikDD-treated mice. Thus, in comparison with CMV-BikDD, CT90-BikDD possesses comparable anti-tumor activity and will have minimum side effects induced by its expression in normal tissues.

Figure 25:
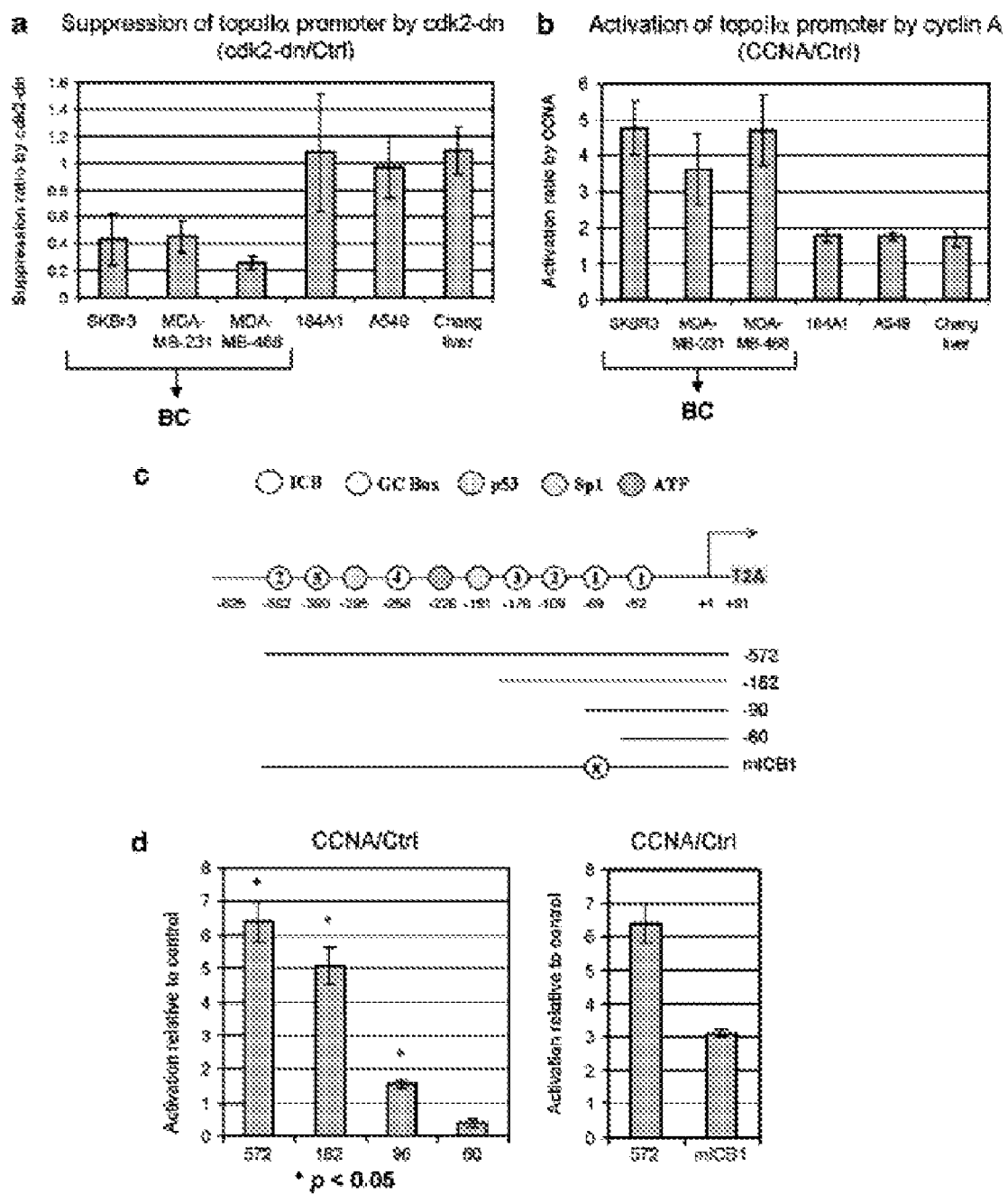
FIG. 25 shows ICBs mediate breast cancer-specific signaling.
Figure 25:
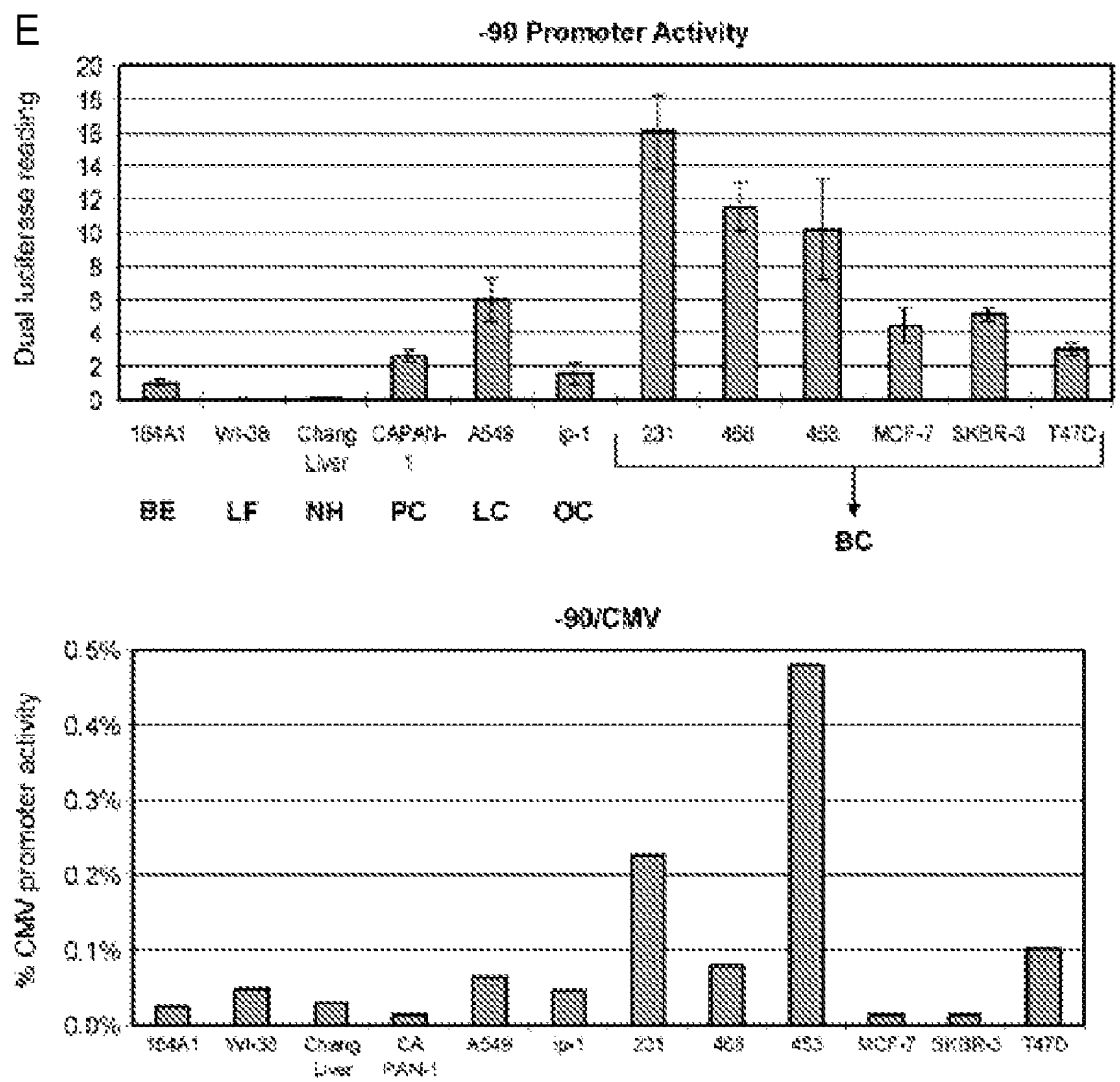
Figure 26:
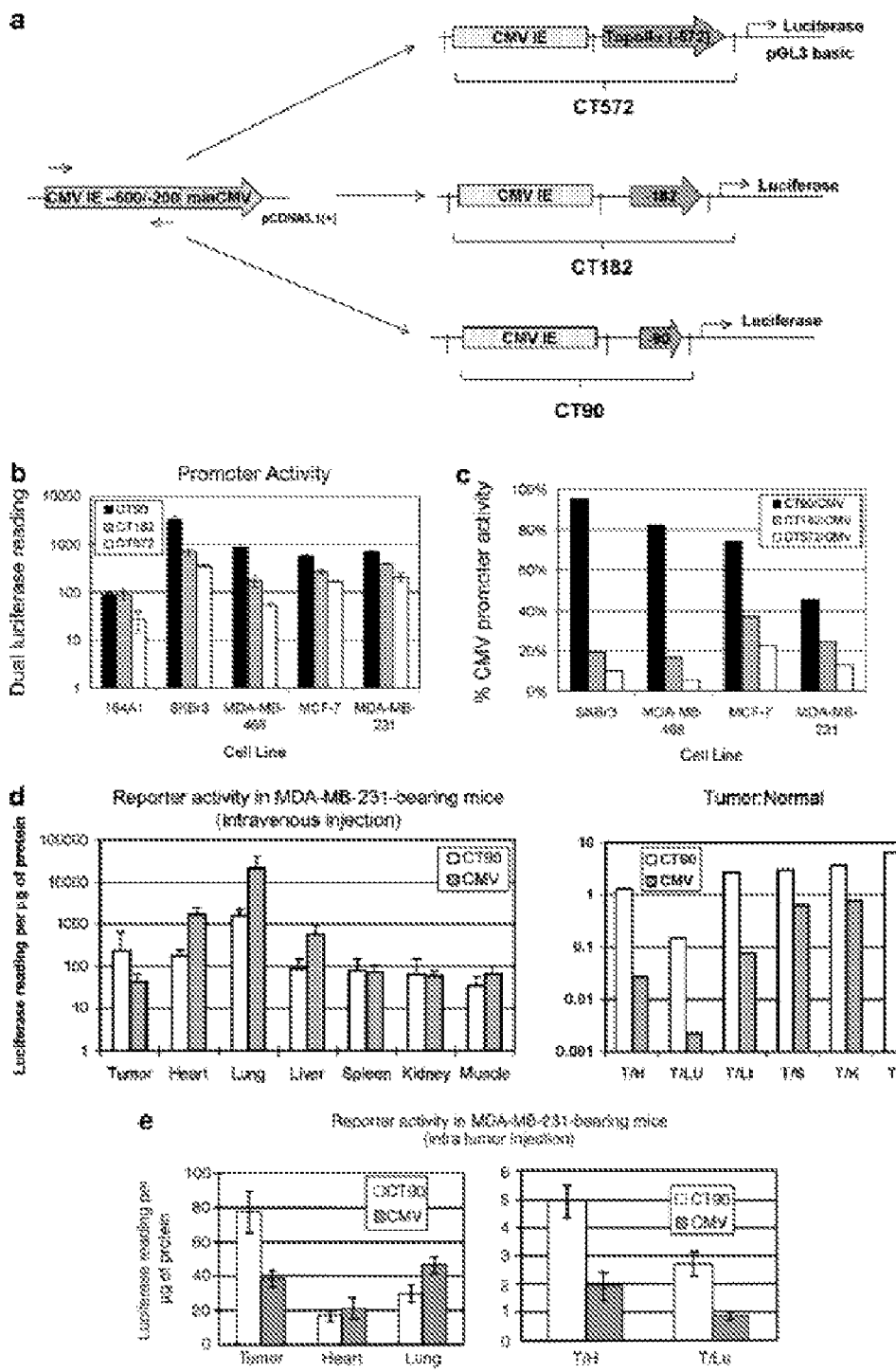
FIG. 26 demonstrates that enhancer sequence of CMV promoter potentiates −90 topoIIα promoter activity specifically in breast cancer cells.

ICB1 Can Mediate Activation of topoIIα Promoter by Cdk2/cyclin A Specifically in Breast Cancer Cells To enhance the basal activity of topoIIα promoter in breast cancer cells, in a specific embodiment a strong enhancer is linked to it. However, in certain aspects due to the possible interference from some of the regulatory elements in the topoIIα promoter, the addition of the strong enhancer might not achieve high basal activity and could even lose breast cancer specificity (see later in FIG. 26). In order to develop a TSP possessing both specificity and high basal activity in breast cancer cells, the present inventors reasoned that a minimal breast cancer-specific element linking to an enhancer would have a better successful opportunity. Thus, we set out to identify a breast cancer-specific element in the topoIIα promoter. To this end, we first explored the possible breast cancer-specific signal to activate topoIIα promoter, then looked for the cis-element that mediated this signaling. TopoIIα expression is upregulated during S phase and peaks during G2/M (Woessner et al., 1991). Since the essential cell-cycle regulator Cdk2 is activated during S and G2 phases (Vermeulen et al., 2003), the present inventors asked whether topoIIα promoter activity might be upregulated by Cdk2. To this end, the regulation of cdk2 on topoIIα promoter activity was examined by cotransfecting a dominant-negative Cdk2 mutant (Cdk2-dn) (van den Heuvel & Harlow, 1993) and topoIIα promoter reporter construct in a reporter assay. Cdk2-dn suppressed topoIIα promoter activity in three different breast cancer cells but not in normal breast epithelial cells (184A1), lung cancer cells (A549), or nonmalignant hepatocytes (Chang liver) (Castagnetta et al., 2003) (FIG. 25A). Since Cdk2 associates with cyclin E and cyclin A in late G1 and S phase, respectively, we investigated which one could activate topoIIα promoter. Expression of cyclin A significantly induced activation of the topoIIα promoter in breast cancer cells but not in other cell types (FIG. 25B). On the contrary, cyclin E had minimum effect on the topoIIα promoter in breast cancer cells (data not shown). These data suggest that cyclin A/Cdk2 activates the topoIIα promoter in a breast cancer-specific manner.

Following the results above, the cyclin A/Cdk2-responding element in the topoIIα promoter might be the potential breast cancer-specific element. To identify this element, we generated a series of deletion mutants of the topoIIα promoter, including −182, −90, −60, which contain three, one, and no ICB(s), respectively (FIG. 25C) (Adachi et al., 2000; Falck et al., 1999; Hochhauser et al., 1992). Their responses to cyclin A activation were examined in the breast cancer cell line SK-BR3 (FIG. 25D, left panel). Cyclin A can activate the full-length promoter as well as its −182 and −90 deletion mutants that harbor at least one ICB (−572, −182, and −90 in left panel of FIG. 2D, p<0.05), but not the −60 deletion mutant which lacks any ICB (−60 in left panel of FIG. 2D). Similar results were obtained when these experiments were performed in other two breast cancer cell lines MDA-MB-468 and MDA-MB-231 (data not shown), indicating ICBs could be important for mediating the cyclin A signal. This point was further supported by the fact that the mutation of ICB1 in full-length topoIIα promoter (FIG. 2C, lowest one) resulted in the greater reduction in the response to cyclin A (FIG. 2E, right panel), suggesting that ICB1 in the topoIIα promoter is required for full response to cyclin A/cdk2 activation and may represent a minimal breast cancer-specific element.

To validate the role of ICB1 in mediating breast cancer specificity of topoIIα promoter, the activity of the −90 deletion mutant was examined in a panel of cell lines since it contains only one ICB site. Similar to the full-length promoter, the −90 promoter activity was higher in most breast cancer cell lines than in other types of cells (FIG. 25E, upper panel), indicating it remains the breast cancer specificity. However, the activity ratio of the −90 promoter to the CMV promoter (−90/CMV) again showed its low basal activity in breast cancer cells (<0.5% in lower panel of FIG. 25E). Since most other regulatory elements have been deleted in the −90 promoter, it may be easier to be engineered into higher basal activity in breast cancer and remains the specificity.

CT90 Promoter, −90 topoIIα Promoter Potentiated with Enhancer Sequence of CMV Promoter, Possesses a Stronger Specific Activity in Breast Cancer Cells In Vitro and In Vivo To enhance basal activity in breast cancer cells, we connected the enhancer sequence of the CMV promoter (CMV enhancer) (Xu et al., 2001) to three ICB-harboring promoters: full-length topoIIα promoter and its −182 and −90 deletion mutants. The composite promoters were designated as CT572, CT182, and CT90, respectively (FIG. 26A). Interestingly, among these composite promoters, CT90 has highest activity in breast cancer cells relative to the normal 184A1 cells (FIG. 26B, the reporter activity is shown by log scale). Moreover, the activity of CT90 is comparable to the CMV promoter in breast cancer cells (FIG. 26C). CT572 and CT182 have lower specificity for breast cancer cells than CT90 (FIG. 26B), and their activities were enhanced in a very limited extent (FIG. 26C), suggesting that some elements other than ICB1 in topoIIα promoter may interfere the CMV enhancer activity.

To test whether CT90 possesses sufficient specificity and activity for systemic liposome gene therapy, we further examine its activity in vivo. The luciferase constructs driven by the CT90 or CMV promoter (CT90-luc and CMV-luc, respectively) were complexed with DOTAP:Chol liposome, then intravenously injected into mice carrying either MDA-MB-231 breast cancer xenograft. The promoter activity in the normal and tumor tissues was determined by reporter assay (upper panels of FIG. 26D). As mentioned earlier, when cationic liposome-DNA complex is administrated through i.v. injection into animal, lung and heart will uptake an essential portion of liposome, resulting in the higher gene expression level in these two organs (Barron, 1999; Li et al., 1998; Lu et al., 2002; Templeton et al., 1997). Likewise, the biodistribution of reporter activities from CMV-luc showed similar pattern: the highest in lung, second and third highest in heart and liver, lower in all other tissues (FIG. 26D, upper panels). This indicates that the reporter activity from CMV-luc represents the gene delivery efficiency of liposome in our animal models. To evaluate the specificity of CT90 in vivo, the liposome uptake efficiency was normalized in different tissues (Barron, 1999; Li et al., 1998; Lu et al., 2002; Templeton et al., 1997) by calculating the activity ratio of CT90 to the CMV promoter (CT90/CMV in the lower panels of FIG. 26D). The normalized CT90 activity was higher in the tumor, but much lower in the normal organs, especially in the major liposome-trapping organs heart, lung, and liver (FIG. 26D). Similar biodistribution of CMV-luc and CT90-luc activity were observed in another mouse model carrying MDA-MB-468 breast cancer xenograft (data not shown). When another liposome SN (Li et al., 2003; Zou et al., 2002) was used to deliver DNA construct, CT90 still showed similar tumor specificity (data not shown). It needs to be mentioned here that the liposome delivery efficiency to spleen, kidney, and muscle is much lower than that to lung, heart, and liver. Therefore, in these experiments, the expression of delivered gene in the latter three organs is minimum and likely negligible in the comparison of promoter activity. To rule out the influence from gene delivery efficiency, the CMV-luc or CT90-luc is delivered by DOTAP: Chol liposome into MDA-MB-231 tumor-bearing mice through intratumoral injection. The luciferase activities from the CT90 promoter are still higher in tumor, and lower in lung or heart, than those from the CMV promoter (FIG. 26E), indicating CT90 is a tumor-specific promoter in vivo. Interestingly, the breast cancer specificity and activity of CT90 in vivo are higher than those in vitro (FIGS. 26C and 26D). Such phenomenon that in vivo liposome delivery increases the promoter specificity compared to in vitro delivery has also been observed in other study (Lu et al., 2002). These results demonstrated that CT90 is a stronger breast cancer-specific promoter that is suitable for breast cancer targeting in the gene therapy setting.

Example 2

Pancreatic Cancer-Specific Expression

The present inventors utilized pancreatic cancer-specific promoter sequences to control expression of a polynucleotide encoding a mutant Bik polypeptide. Exemplary methods and compositions directed to this goal are described in this Example.

Cell Lines

Human pancreatic cancer (PANC-1, CAPAN-1 and AsPC-1), prostate cancer (LNCaP and PC-3) cell lines, immortalized normal lung fibroblast (WI-38) and mammary epithelial (184A1) cells were obtained from the American Type Culture Collection (ATCC, Rockville, Md.). Immortalized human pancreatic cells E6E7 was kindly provided by Dr. Paul Chiao (University of Texas M. D. Anderson Cancer Center, Houston, Tex.). Chang liver cells and ovarian cancer cell line SKOV3.ip1 were also used. PANC-1, CAPAN-1, AsPC-1, WI-38, and SKOV3.ip1 and Chang liver cells were cultured with DMEM/F12 medium supplemented with 10% fetal bovine serum (FBS), penicillin (100 units/ml) and streptomycin (100 mg/ml) (Invitrogen, Carlsbad, Calif.). LNCaP and PC-3 cells were maintained in RPMI 1640 medium (Invitrogen) with 10% (FBS), penicillin and streptomycin. 184A1 cells were maintained in complete mammary epithelium growth medium (MEGM) (Cambrex, Walkersville, Md.) and E6E7 cells in Keratiocyte-SFM supplemented with epidermal growth factor, pituitary extract (Invitrogen).

Constructs

The CCKAR promoters (−726 to +1; primers CCKAR-p1 and CCKAR-p2), uPAR promoter (−812 to +1; primers uPAR-p1, and uPAR-p2), RDC-1 promoter (−881 to +1; primers RDC-p1, and RDC-p2), CTRB1 promoter (−946 to +1; primers CTRB1-p1, and CTRB1-p2) and CPA1 promoter (−1010 to +108; CPA1-p1 and CPA1-p2) were obtained by PCR amplification of PANC-1 genomic DNA using primers shown in Table 2.

TABLE 2

The sequence of potential pancreatic cancer specific promoters

| | |
|---|---|
| CCKAR-p1: | 5'-AGGACCCAGGTACCTATGTTCAAAAGTGCCTC-3' (SEQ ID NO: 1) |
| CCKAR-p2: | 5'-CCTTGCCTGCTGCTTTCCACCAAGTGCT-3' (SEQ ID NO: 2) |
| RDC1-p1: | 5'-CAGGTTGGGAAAATGGTCAGCCCTCCTGAAA-3' (SEQ ID NO: 3) |
| RDC-p2: | 5'-CGTTCTGAGGCGGGCAATCAAATGACCTAT-3' (SEQ ID NO: 4) |
| uPAR-p1 | 5'-CCCGCTAGCCTAATTTTATTTTATTTTTAATTC-3' (SEQ ID NO: 5) |
| uPAR-p2 | 5'-CCCCTCGAGGTATTTTGGAAAAATGTCCTTATCTAG-3' (SEQ ID NO: 6) |
| REG1A-p1 | 5'-CGCACGCGTAGGCATCAGCTCTCTACAATTC-3' (SEQ ID NO: 7) |
| REG1A-p2 | 5'-AGCCTCGAGCAGGATCTGAGATAAGAACCACG-3' (SEQ ID NO: 8) |
| CTRB1-p1 | 5'-ACGGCGCTCGAGTCCATCAGTTCTCATC-3' (SEQ ID NO: 9) |
| CTRB1-p2 | 5'-TTACTTAAGCTTGTGTAGGACGCCTGTC-3' (SEQ ID NO: 10) |

These PCR fragments were subcloned into pCRII-TOPO (Invitrogen) to generate pCRII-TOPO-CCKAR, pCRII-TOPO-uPAR, pCRII-TOPO-RDC1, and pCRII-TOPO-CTRB. All PCR products were verified by sequencing. The promoter fragments were then inserted into the KpnI/XhoI sites of pGL-3 basic (Promega, Madison, Wis.) to obtain plasmids pGL3-CCKAR-Luc, pGL3-uPAR-Luc, pGL3-RDC1-Luc, and pGL3-CTRB1-Luc. The CMV enhancer/promoter-controlled Firefly luciferase gene plasmid pCMV-Luc (comprised of the CMV promoter cloned into the pGL-3 vector). The plasmid pRL-TK, comprising a *Renilla* luciferase reporter gene, was obtained from Promega.

The fragment of WPRE enhancer was released from pGEM-3Z-WPRE (a generous gift from Dr. J. B Uney, University of Bristol, Bristol, UK) by Asp718/SalI digestion and inserted into the SmaI sites of pGL3-basic by blunt ligation to produce intermediate pGL3-Luc-WPRE. Plasmid pGL3-basic was digested with XbaI, Klenow blunted and annealed to the blunted Asp718/SalI WPRE fragment of intermediate pGL3-Luc-WPRE to give pGL3-Luc-WPRE. The SpeI/XhoI-blunted CCKAR fragment of pCRII-TOPO-CCKAR was subcloned into blunted NheI/XhoI site of pGL3-Luc-WPRE, resulting into pGL3-CCKAR-Luc-WPRE. The HindIII/NotI-blunted CCKAR fragment of pCRII-TOPO-CCKAR was subcloned into the MscI/NheI-blunted site of pGL3-TSTA-Luc (a gift of Dr. M. Carey, UCLA School of Medicine, LA) (Zhang L, et al, Cancer Res 2003), obtaining pGL3-CCKAR-TSTA-Luc-WPRE. Finally, the CCKAR fragment of pCRII-TOPO-CCKAR digested with NotI/BglII was inserted into the same site of pGL3-CCKAR-TSTA-Luc-WPRE, producing pGL3-CCKAR-TSTA-Luc-WPRE (pGL3-CTP-Luc).

Transfection

Cells were seeded in 12-well plates at 40-50% confluence at 37° C. with 5% CO2 in corresponding medium as described above, 16 h prior to transfection. Cells were transfected with designated plasmid DNA along with pRL-TK as internal control, using DOTAP:Chol liposome (from N. Templeton, Baylor College of Medicine, Houston, Tex.) according to the recommended method. The non-expression vector, pGL3-basic, was used as a negative control. To compare the activities of transcriptional regulatory elements with each other, the same molar amount of plasmid DNA was used.

Orthotopic Animal Models of Pancreatic Cancer and Systemic Plasmid DNA Delivery

Athymic female BALB/c nu/nu mice (Charles River Laboratories, Wilmington, Mass.), at 6-8 weeks of age, were used as xenograft hosts. Mice were maintained in a specific pathogen-free environment, in compliance with M.D. Anderson Cancer Center rules. AsPC-1 cells in logarithmic-phase growth were trypsinized and washed twice with PBS. For the orthotopic model, mice were anesthetized with Aventin (Sigma) (Xie, Mol. Endocrinl 2004) and placed at the supine position. The abdomen area was cleaned with 70% ethanol, and an upper midline abdomen incision was made. The pancreas was exteriorized and its tail was injected with 50 μl of aliquots of AsPC-1 cells ($1\times10^6$ cells). The incision was closed with wound clips.

Plasmid DNA:liposome complexes were prepared as previously described (Templeton, Nat Biotech 1997). Briefly, DNA and DOTOP:Chol stock were separately diluted in 5% dextrose in water (D5W) at room temperature. The DNA solution was added rapidly at the surface of the liposome solution in equal volume and mixed by pipetting up and down twice. The preparation was made fresh 2 h prior to injection. The nude mice in which tumors reached about 50 mm$^3$ in ectopic model or the same period of time in othotopic model were injected with 100 μl of DNA:liposome complexes containing 50 μg of DNA into the tail vein using a 29-gauge needle, once a day for three consecutive days. Mice were in vivo imaged every day post injection and sacrificed 24 h after last injection.

Luciferase Assays

Transiently transfected cells were lysed and assayed for luciferase activity by using the Dual-Luciferase® Reporter Assay System (Promega, Madison, Wis.) following the manufacturer protocol with a TD 20/20 luminometer (Turner Designs, Sunnyvale, Calif.). The dual luciferase ratio was defined as the Firefly luciferase activity of the tested plasmids over the Renilla luciferase activity of pRL-TK, expressed as the means of triplicate transfections, which were repeated at least four times. Compared to the ratio of CMV activity, the percentage was presented.

To assay tissue-derived luciferase activity, animals were euthanized and dissected. Tissue specimens from tumors and other organs including pancreas, lung, heart, liver, spleen, kidney, brain, intestine, muscle, and ovary, et al. were resected, and homogenized with a PRO 250 homogenizer (Pro Scientific, Inc., Monore, Conn.) in 300 μl of luciferase lysis buffer (Promega) containing $\frac{1}{100}$ diluted protein inhibitor cocktail (Roche). Specimens were centrifuged at 8,000 rpm for 5 min and placed temporarily on ice. Luciferase activity of the supernatants was measured with a Lumat LB9507 luminometer (Berthod, Bad Wildbad, Germany) and the protein concentration was determined using the detergent compatible (DC) protein assay system (Bio-Rad, Hercules, Calif.) with MRX microplate reader (Dynex technologies, Inc., Chantilly, Va.). The luminescence results are reported as relative light units (RLU) per milligram of protein.

Imaging and Quantification of Bioluminescence Data

Mice were anaesthetized with Aventin. D-luciferin (Xenogen, Alemeda, Calif.) (30 mg/ml in PBS) was intraperitoneally injected at 150 mg/kg mouse body weight. Ten min after D-luciferin injection, mice were imaged with an IVIS™ Imaging System (Xenogen), consisting of a cooled CCD camera mounted on a light-tight specimen chamber (dark box), a camera controller, a camera cooling system, and a Windows-based computer system. Imaging parameters were maintained for comparative analysis. Gray scale reflected images and bioluminescence colorized imaged were superimposed and analyzed using the Living Imaging software version 2.11 (Xenogen). A region of interest (ROI) was manually selected over relevant regions of signal intensity. The area of the ROI was kept constant and the intensity was recorded as maximum photon counts within a ROI (Xie et al., 2004). In some experiments after imaging, animals were euthanized and organs of interest were removed, arranged on black, bioluminescence-free paper, and ex vivo imaged within 30 min.

Figure 9:
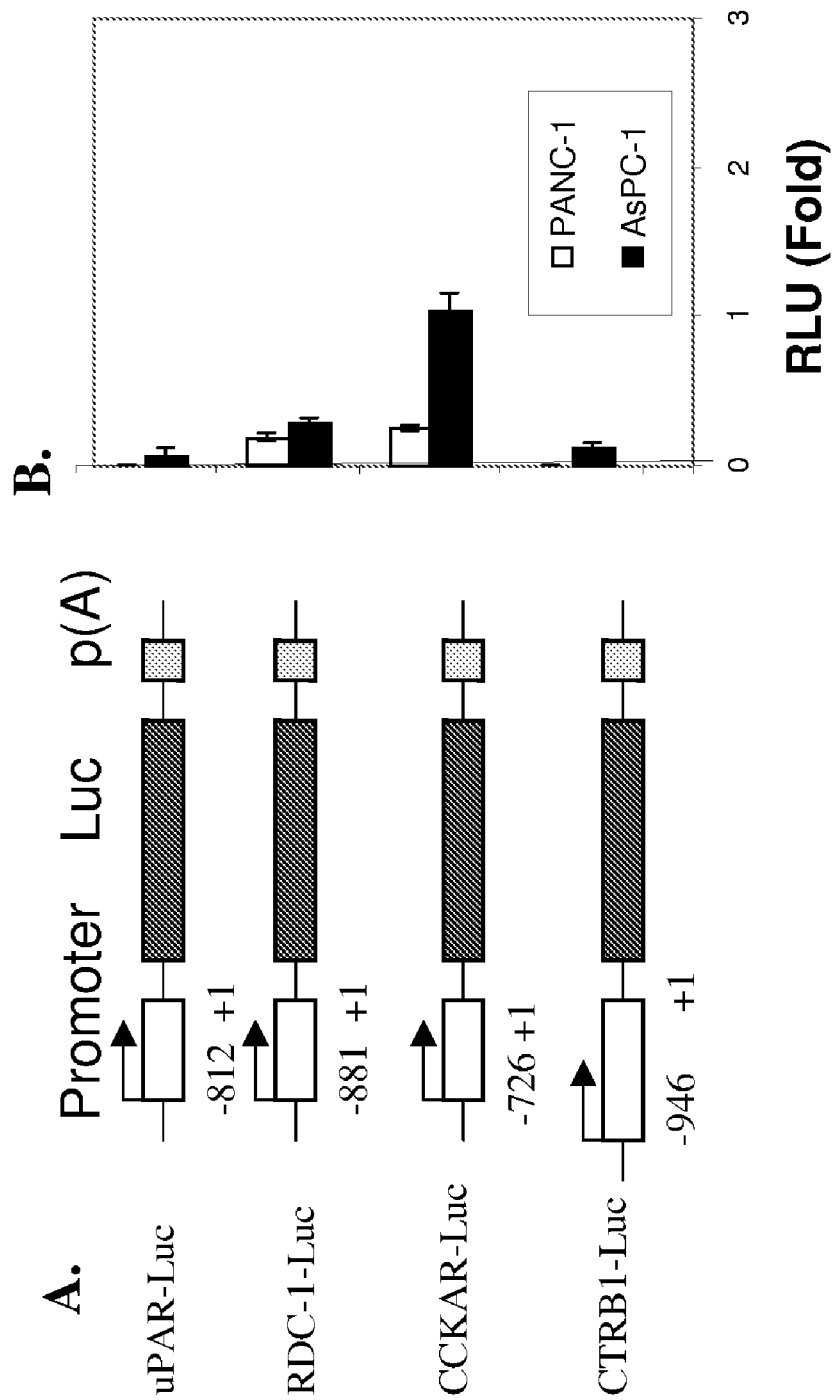
FIGS. 9A and 9B illustrate constructs of pancreatic specific promoters (FIG. 9A) and their respective luciferase assays (FIG. 9B). The data represent mean of four independent experiments; bar, SD.

FIG. 9A illustrates constructs of pancreatic specific promoters. The promoter sequences of human Cholecystoskinin A receptor (CCKAR), orphan G protein-coupled receptor (RDC1), urokinase-type plasminogen activator receptor (uPAR), and chymotrypsinogen B1 (CTRB1) were PCR-amplified and subcloned into the reporter plasmid pGL3-basis, thereby regulating expression of firefly luciferase gene. Cells were transiently co-transfected with similar molar quantities of plasmid DNA with the internal control pRL-TK. As shown in FIG. 9B, forty-eight hours later, dual luciferase ratio was measured and shown as RLU (fold) normalized to the Rellina luciferase.

Pancreatic Cancer-Specific Expression of a Desired Polynucleotide

Figure 10:
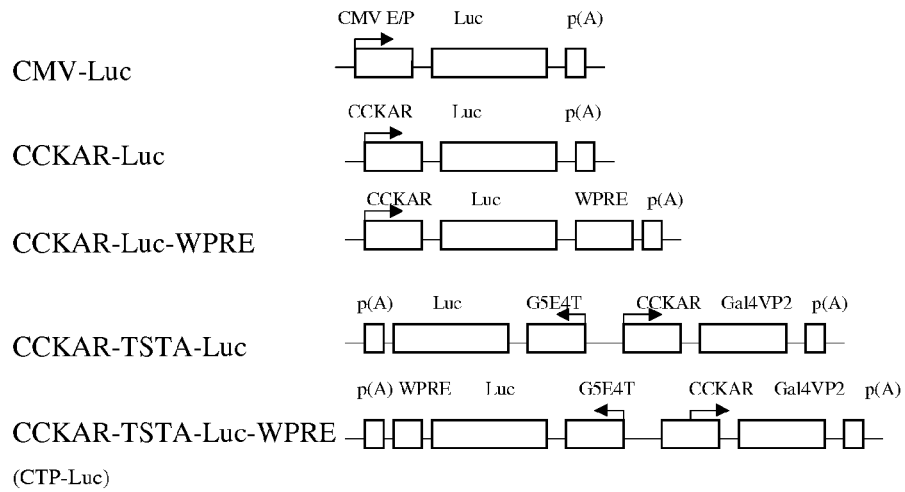
FIG. 10A illustrates a schematic diagram of CCKAR-based and CMV-based constructs, containing the Firefly luciferase reporter gene under the control of the minimal CCKAR promoter without or with WPRE, or CCKAR/TSTA without or with WPRE, or under CMV enhancer/promoter.
FIG. 10B demonstrates activity of constructs transiently transfected into AsPC-1, and PANC-1 pancreatic cancer cells.
FIG. 10C shows the tissue specificity of CCKAR-based promoter composites. The data represent mean of four independent experiments; bar, SD.
Figure 10:
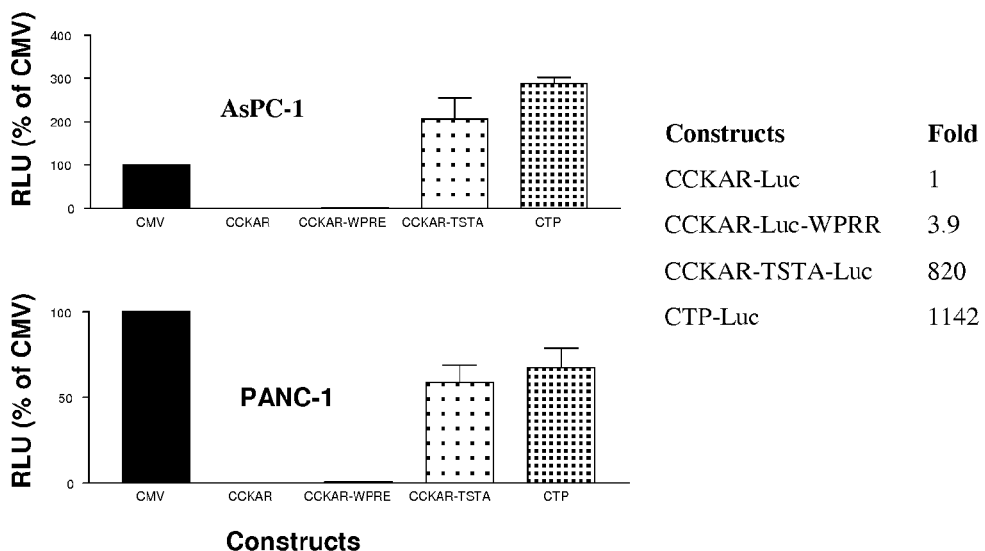
Figure 10:
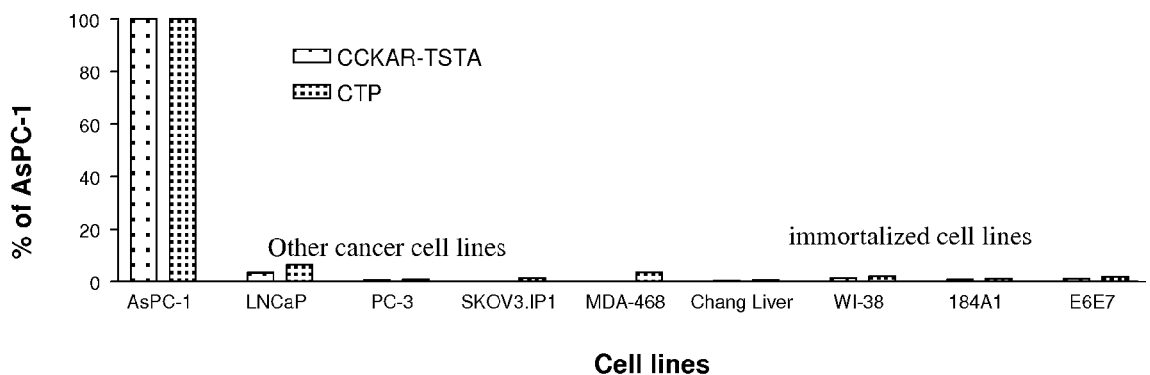

FIG. 10A illustrates a schematic diagram of CCKAR-based and CMV-based constructs, containing the Firefly luciferase reporter gene under the control of the minimal CCKAR promoter without or with WPRE, or CCKAR/TSTA without or with WPRE, or under CMV enhancer/promoter. Gal4VP2: VP2: duplicated HSV1 VP16 immediate early transactivator domain have a highly potent to activate when fused to the GAL4 DNA binding domain. For the G5E4T sequence (SEQ ID NO:22), G5 comprises 5 tandem copies of the 17 bp GAL4 DNA binding site near consensus DNA binding sites. E4T is E4TATA which comprises the adenovirus E4 minimal promoter from −38 to +38 relative to the start site. FIG. 10B demonstrates activity of constructs transiently transfected into AsPC-1, and PANC-1 pancreatic cancer cells. Cells were transiently co-transfected with similar molar quantities of plasmid DNA with the internal control pRL-TK. Forty-eight hours later, dual luciferase ratio was measured and then compared to CMV activity presented as percentage. The data represent the mean of four independent experiments; bar, SD. FIG. 10C shows tissue specificity of CCKAR-based promoter composites. Other cancer cells (LNCaP, PC-3, SKOV3.ip1, MDA-468) and immortalized normal cells (Chang liver, WI-38, 184A1, and E6E7 cells) were transiently co-transfected with the internal control pRL-TK. Forty-eight hours later, dual luciferase ratio was measured. The percentage was presented in comparison to the ratio of the activity in AsPC-1.

Figure 11:
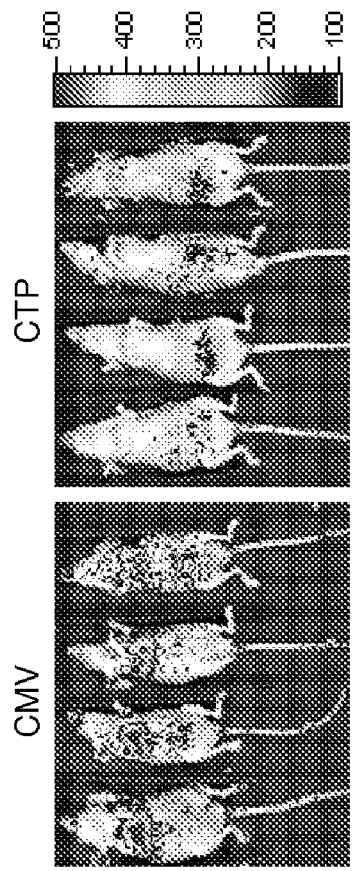
FIG. 11 shows in vivo transgene expression in orthotopic tumor model of AsPC cells after systemic delivery of CTP-Luc and CMV-Luc plasmid DNA.
Figure 11:
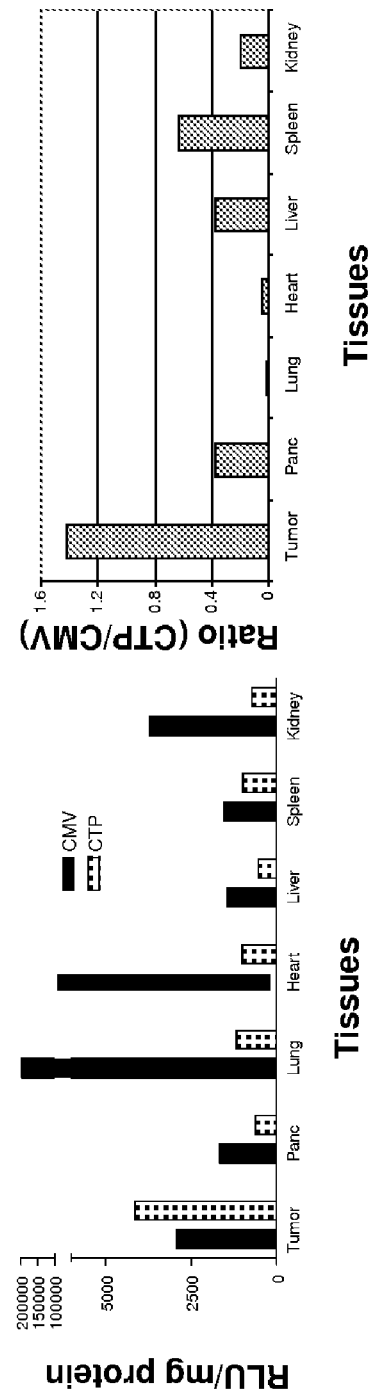

In vivo transgene expression in orthotopic tumor model of AsPC cells after systemic delivery of CTP-Luc and CMV-Luc plasmid DNA is shown in FIG. 11. FIG. 11A shows in vivo imaging of mice. Nude mice bearing subcutaneous AsPC-1 tumor were injected in the tail vein with 50 μg of DNA in DNA (CTP-Luc or CMV-Luc):liposome complexes, once a day for three consecutive days. 24 h after last injection, mice were anesthetized, and imaged for 5 min using an IVIS™ Imaging System 10 minutes following i.p. injection of D-luciferin. The representative imaging of mice are shown. FIG. 11B shows firefly luciferase activity in tissue extracts was quantified with a luminometer and expressed as relative luciferase units per milligram of total protein. The ratio was calculated by comparing the level of luciferase activity of CTP mice to CMV mice.

Figure 18:
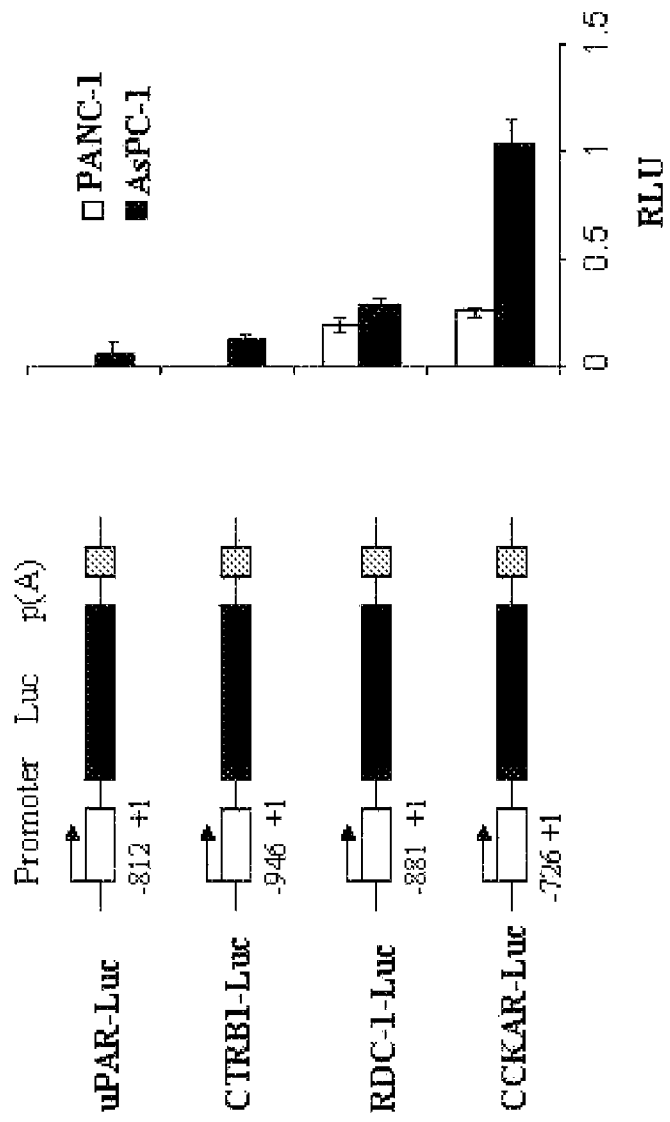
FIG. 18 shows that human cholecystoskinin type-A receptor (CCKAR) promoter is potentially pancreatic cancer-specific.

FIG. 18 shows that human cholecystoskinin type-A receptor (CCKAR) promoter is potentially pancreatic cancer-specific. In FIG. 18A, constructs of candidates for pancreatic cancer-specific promoter. CCKAR, orphan G protein-coupled receptor (RDC1), urokinase-type plasminogen activator receptor (uPAR), and chymotrypsinogen B1 (CTRB1) were polymerase chain reaction-amplified and subcloned into the reporter plasmid pGL3-basic, driving a firefly luciferase gene. In FIG. 18B, PANC-1 and AsPC-1 cells were transiently co-transfected with the plasmid DNA indicated and pRL-TK. Forty-eight hours later, the dual luciferase ratio was measured and shown as relative light units (RLU) normalized to the Renilla luciferase control.

Figure 19:
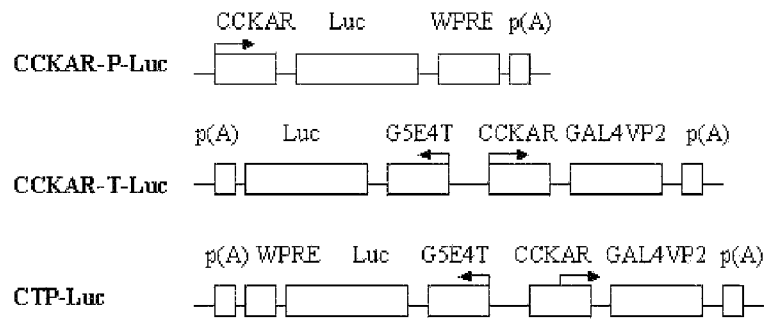
FIG. 19 demonstrates molecular-engineered cholecystoskinin type-A receptor (CCKAR)-based promoters are more active and retain pancreatic cancer specificity.
Figure 19:
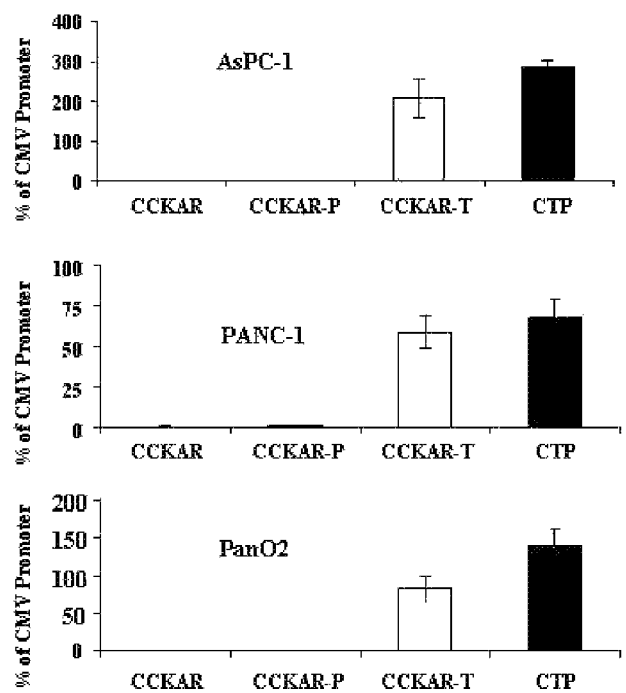
Figure 19:
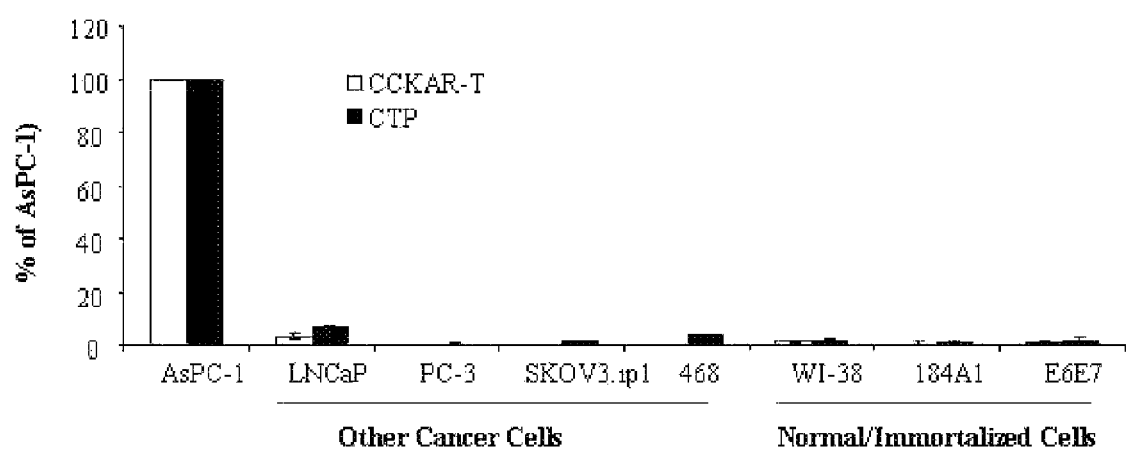

FIG. 19 demonstrates molecular-engineered cholecystoskinin type-A receptor (CCKAR)-based promoters are more active and retain pancreatic cancer specificity. In FIG. 19A, there is a schematic diagram of engineered CCKAR-based constructs including pGL3-CCKAR-Luc-WPRE (CCKAR-P-Luc)), pGL3-CCKAR-TSTA-Luc (CCKAR-T-Luc), and pGL3-CCKAR-TSTA-Luc-WPRE (CTP-Luc). In FIG. 19B, there is activity of CCKAR-based promoters in pancreatic cancer cells. AsPC-1, PANC-1 and PanO2 cells were transiently co-transfected with plasmid DNA and pRL-TK. Forty-eight hours later, the dual luciferase ratio was measured. The percentage relative to the activity of the CMV promoter is shown. The data represent the mean of four independent experiments. In FIG. 19C, there is tissue specificity of CCKAR-based promoter composites. Non-pancreatic cancer (LNCaP, PC-3, SKOV3.ip1, MDA-MB-468, and HeLa), and normal and immortalized (WI-38, 184A1, and E6E7) cell lines were transiently co-transfected with the plasmids indicated and pRL-TK. Forty-eight hours later, the dual luciferase ratio was measured. The percentage relative to the activity in AsPC-1 cells is shown.

Figure 20:
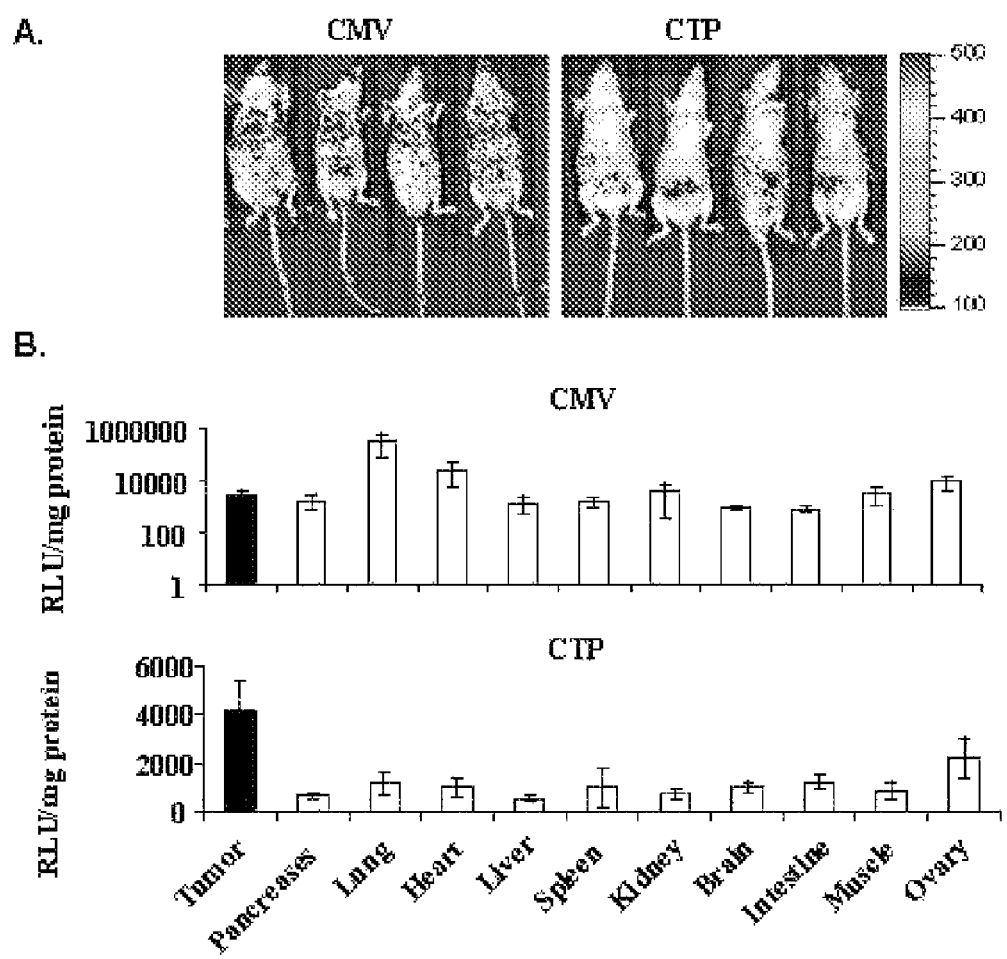
FIG. 20 shows the composite of cholecystokinin-type-A receptor (CCKAR)-two-step-transcriptional activation (TSTA)-woodchuck hepatitis virus posttranscriptional regulatory element (WPRE), CTP, is robust and pancreatic cancer-specific in an orthotopic animal model. Nude mice bearing orthotopic AsPC-1 tumors were give 50 µg of DNA in DNA:liposome complexes via the tail vein once a day for 3 consecutive days.

FIG. 20 shows the composite of cholecystokinin-type-A receptor (CCKAR)-two-step-transcriptional activation (TSTA)-woodchuck hepatitis virus posttranscriptional regulatory element (WPRE), CTP, is robust and pancreatic cancer-specific in an orthotopic animal model. Nude mice bearing orthotopic AsPC-1 tumors were give 50 µg of DNA in DNA: liposome complexes via the tail vein once a day for 3 consecutive days. In FIG. 20A, there is in vivo imaging of mice. Mice were anesthetized and imaged for 5 min using an IVIS imaging system 10 minutes after intraperitoneal injection of D-luciferin. In FIG. 20B, there is tissue distribution of luciferase expression. Tissue specimens from tumors and organs as shown were dissected and measured for luciferase activity with a luminometer. Data were expressed as relative luciferase units per milligram of total protein.

Figure 21:
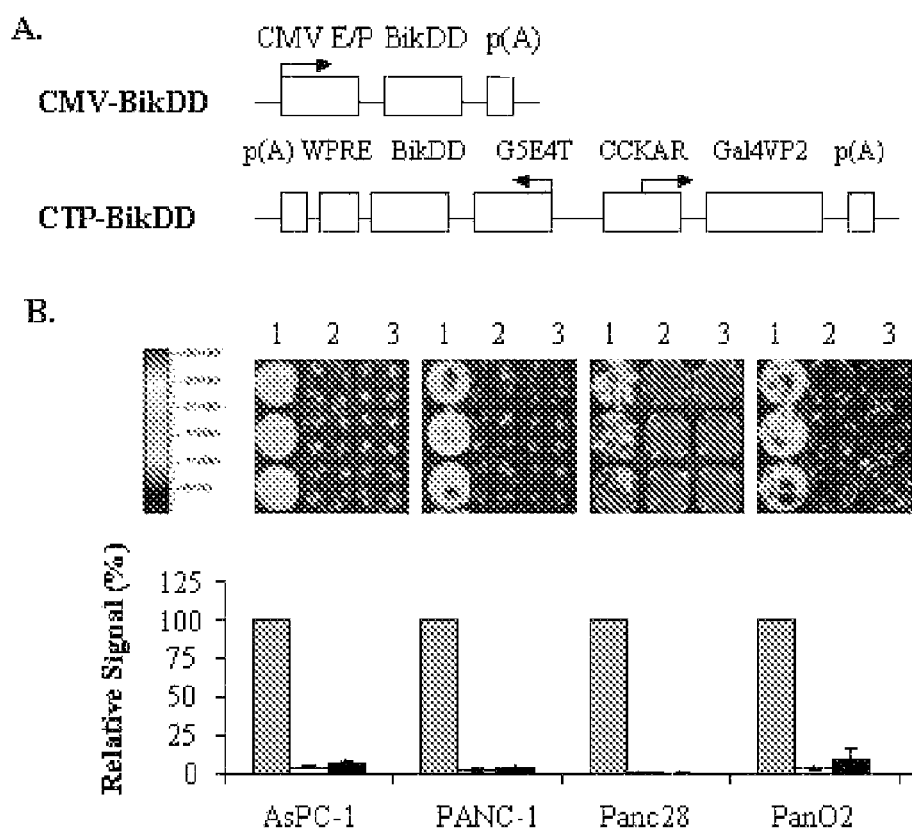
FIG. 21 provides expression of Bik mutant (BikDD) driven by CTP kills pancreatic cancer cells effectively and specifically.

FIG. 21 provides expression of Bik mutant (BikDD) driven by CTP kills pancreatic cancer cells effectively and specifically. In FIG. 20A, there is a schematic diagram of expression constructs in the pUK21 backbone. CMV-BikDD, pUK21-CMV-BikDD; CTP-BikDD, pUK21-CTP-BikDD. In FIG. 20B, the killing effects of BikDD driven by CMV or CTP are provided. A panel of pancreatic cancer (AsPC-1, PANC-1, MDA-Panc28, and PanO2), immortalized human pancreatic epithelial E6E7 cells were co-transfected with 2 µg of pUK21 (negative control), pUK21-CMV-BikDD (positive control), or pUK21-CTP-BikDD, plus 100 ng of pGL3-CMV-Luc. Forty-eight hours after transfection, the luciferase activity was imaged for 2 min using an IVIS imaging system following a 5-minute incubation with 5 ng/ml of D-luciferin. Representative images were shown in the upper panel. The percentage of the signal compared with the negative control (set as 100%) was calculated (lower panel).

In particular embodiments of the present invention, constructs are similarly generated comprising these exemplary pancreatic-specific promoters operatively linked to a polynucleotide encoding a mutant Bik, followed by introduction into a mammal in need of pancreatic cancer therapy treatment based on analogous methods described herein. Parameters are easily optimized by those of skill in the art, such as delivery mode, concentration of composition, and so forth.

In further embodiments of the present invention, the pancreatic cancer-specific elements are narrowed further to identify even smaller segments within that retain pancreatic cancer-specific expression activity. For example, deletion constructs may be made of these respective regions, and their tissue specificity is tested to identify the smaller segments that maintain the ability to direct expression in pancreatic cancer tissue.

Example 3

Prostate Cancer-Specific Expression

The present inventors utilized prostate cancer-specific promoter sequences to control expression of a polynucleotide encoding a mutant Bik polypeptide. Exemplary methods and compositions directed to this goal are described in this Example.

Development of Targeted Gene Therapy for Metastatic and Recurrent Hormonal Refractory Prostate Cancer In specific embodiments, a promoter that regulates expression of mutant Bik in both androgen-dependent and androgen-independent manners is utilized. A skilled artisan recognizes that in prostate cancer gene therapy, prostate specific promoters, like PSA (Greenberg, DeMayo et al., 1995; Spitzweg, Zhang et al., 1999; Latham, Searle et al., 2000; Wu, Matherly et al., 2001), probasin (Greenberg, DeMayo et al., 1995; Zhang, Thomas et al., 2000; Wen, Giri et al., 2003) and hK2 (Xie, Zhao et al., 2001) have been recently developed. The activities of these promoters are androgen-dependent. For patients with advanced, metastatic prostate cancer, hormonal ablation is the primary choice of therapy. However, after chemical castration, the adrenal glands secrete large amounts of the inactive precursor steroids dehydroepiandrosterone and androstenedione as a compensatory source of androgen (Denis, 1996). Furthermore, most androgen-independent prostate adenocarcinoma cells up-regulate AR expression, select for mutant AR with increased steroid responsiveness or reduced steroid specificity, or up-regulate growth factor signaling that can stimulate AR activity (Feldman and Feldman, 2001). Moreover, significant side effects associated with this therapy have led to the more widespread use of intermittent ablation protocols, in which patients are treated with leutinizing hormone releasing hormone agonists for up to 12 months before discontinuing therapy until tumor progression begins to occur (Bruchovsky, Klotz et al. 2000). Thus, for numerous disease stages, patients are often hormonally intact, allowing the use of androgen-responsive vectors to direct expression of therapeutic genes to prostatic tissue.

Androgen-independent prostate cancer (AIPC) is an untreatable form of prostate cancer in which the normal dependence on androgens for growth and survival has been bypassed. AIPC is selected for by androgen ablation therapy (Feldman and Feldman, 2001). It is proposed that malignant androgen- and AR-independent epithelial stem cells 'lurking' in the normal prostate become selected for by therapy. A subset of these AR mutations map to the ligand-binding domain (LBD) and are proposed to cause resistance by altering the response of the receptor such that noncanonical ligands such as estrogen or hydrocortisone, or even androgen receptor antagonists such as flutamide, behave as agonists (Chen, Welsbie et al. 2004). Under these conditions, it is very critical for developing an androgen-independent promoter in suicide gene therapy to completely eradicate metastatic and recurrent hormonal refractory prostate cancer.

The Human Telomerase Reverse Transcriptase (hTERT) Promoter is Cancer-Specific

Over the past several years, the enzyme telomerase reverse transcriptase, responsible for maintaining the telomeric DNA at the end of chromosomes, has been the subject of experimental findings that associate it with a magic bullet against cancer. Telomeres are essential element that protects chromosome ends from degradation and end-to-end fusions, rearrangements and chromosome loss. The absence of telomerase activity in human somatic cells prevents compensation for the loss of telomeric DNA ensuing from the inability of conventional DNA polymerase to fully replicate linear DNA molecule. The resulting shortening of the telomeres limits the cell proliferative lifespan and cell senescence. Cell immortalization in vitro and tumor progression are associated with, and may depend on, activation of telomerase.

There has been much in the literature regarding telomerase activity in different patients with cancer. For example, generally telomerase expression was found in 80-100% of human cancer, but almost all normal cells are negative except for sperm cells or highly proliferating cells. In prostate cancer, about 84% of prostate carcinomas and 100% human prostate cancer cell lines are hTERT-positive (Vasef, Ross et al. 1999). Recently, the hTERT promoter has been used for cancer gene therapy, as well as prostate cancer gene therapy (Gu, Andreeff et al. 2002; Kim, Kim et al. 2003; Irving, Wang et al. 2004).

Two-Step Transcription Amplification (TSTA) Significantly Increases Gene Expression The hTERT promoter increases the safety and effectiveness of gene therapy. However, the activity of this unmodified hTERT promoter is much weaker than that of commonly used non-tissue-specific virus-based promoters, such as the cytomegalovirus (CMV) promoter (Cong, Wen et al. 1999; Gu, Andreeff et al., 2002; Komata, Kondo et al. 2002). One of the amplification approaches using the GAL4-VP16 fusion protein, called a two-step transcriptional amplification (activation) (TSTA) approach, can potentially be used to augment the transcriptional activity of cellular promoters (Iyer, Wu et al. 2001; Zhang, Adams et al. 2002). In this system, the first step involves the tissue-specific expression of the GAL4-VP16 fusion protein. In the second step, GAL4-VP16, in turn, drives target gene expression under the control of GAL4 response elements in a minimal promoter. The use of TSTA can potentially lead to amplified levels of the transgene expression.

WPRE is a Useful Enhancer

To increase the activity of tissue-specific promoters, the present inventors and others used CMV enhancer fused to the minimal tissue-specific promoter. Though the activity was increased, the tissue specificity was decreased (unpublished and (Latham, Searle et al., 2000)). To address this issue, the present inventors utilized the post-transcriptional regulatory element of the woodchuck hepatitis virus (WPRE), which involves modification of RNA polyadenylation, RNA export, and/or RNA translation (Donello, Loeb et al., 1998). Enhancement of WPRE occurred both during transient expression in non-viral vectors and viral vectors (Loeb, Cordier et al., 1999; Glover, Bienemann et al. 2002) and when the gene is stably incorporated into the genome of target cells with no loss of tissue specificity (Lipshutz, Titre et al. 2003). WPRE in the sense orientation cloned between the target gene and the poly(A) sequence stimulated 2- to 7-fold more luciferase expression in vitro and 2- to 50-fold in vivo without the use of the WPRE (Zufferey, Donello et al., 1999; Lipshutz, Titre et al., 2003). Furthermore, long-term transgene expression can be mediated by WPRE-containing adenoviral vectors (Glover, Bienemann et al., 2003). Therefore, the WPRE is an effective tool for increasing and prolonging the expression of transgenes in gene therapy.

TSTA and WPRE Enhance the Activity of hTERT Promoter

To determine whether TSTA and WPRE enhance the activity of hTERT promoter, the present inventors first subcloned a series of TSTA- and WPRE-containing hTERTp-based promoter composites. The hTERTp fragment (nt −378 to +56) (Takakura, Kyo et al., 1999) was PCR-amplified from the DNA extracts of LNCaP cells. The hTERTp fragment was subcloned into pGL3-Basic plasmid to drive the firefly luciferase gene, leading to phTERTp-Luc. The WPRE was then inserted into phTERTp-Luc-Luc, resulting in phTERTp-Luc-WPRE. To employ the TSTA system, hTERTp was substituted for PSA promoter of pTSTA plasmid (Zhang, Johnson et al., 2003), producing phTERTp-TSTA-Luc. Finally, the plasmid phTERTp-TSTA-Luc-WPRE was obtained by inserting the WPRE fragment into phTERTp-TSTA-Luc.

ARR2-Fused hTERTp-Based Promoters can be Stimulated by Androgen

The activity of the different promoter composites are tested in AR-positive and AR-negative prostate cancer cells, as well as normal human endothelial cells (HUVEC), which were transiently co-transfected with similar molar quantities of plasmid DNA with the internal control pRL-TK. pGL3-Basic without enhancer/promoter was used for negative control. Forty-eight hours later, dual luciferase ratio was measured and then compared to CMV activity presented as percentage.

In particular, LNCaP cells or PC-3 cells were transiently co-transfected with similar molar quantities of plasmid DNA with the internal control pRL-TK. Forty-eight hours later; dual luciferase ratio was measured and then compared to CMV activity presented as percentage. The data represent means of four independent experiments; bar, SD. FIG. 12C shows tissue specificity of hTERTp-based composites. The lung fibroblast cells WI-38 were transiently co-transfected with the indicated plasmids and the internal control pRL-TK. Forty-eight hours later, dual luciferase ratio was measured. The percentage was presented in comparison to the ratio of the activity in AsPC-1.

Figure 12:
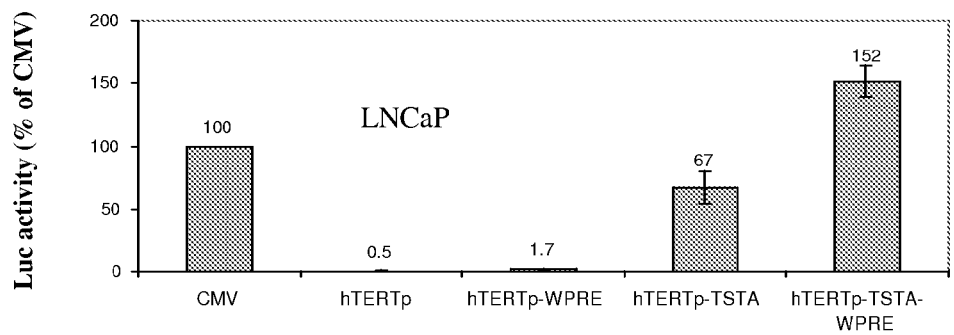
FIG. 12 demonstrates a comparison of firefly luciferase activity under the control of the CMV enhancer/promoter or hTERTp-based promoter composites. Firefly luciferase reporter plasmid constructs comprising a CMV enhancer/promoter or hTERTp without or with WPRE, or hTERTp/TSTA without or with WPRE were tested in LNCaP cells (FIG. 12A), PC-3 prostate cancer cells (FIG. 12B), or WI38 cells (FIG. 12C). The data represent mean of four independent experiments; bar, SD.
Figure 12:
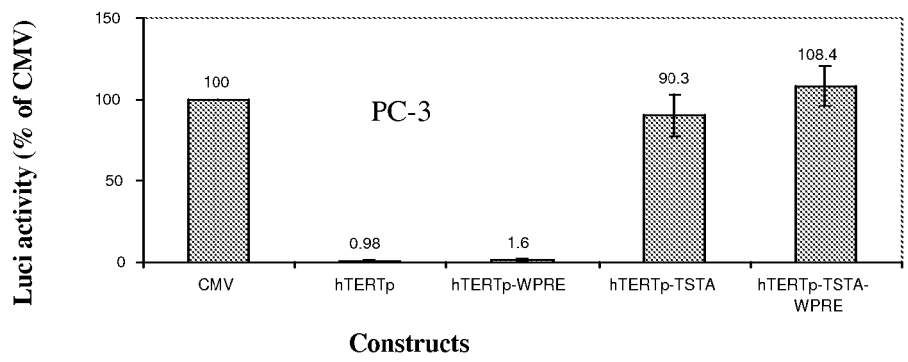
Figure 12:
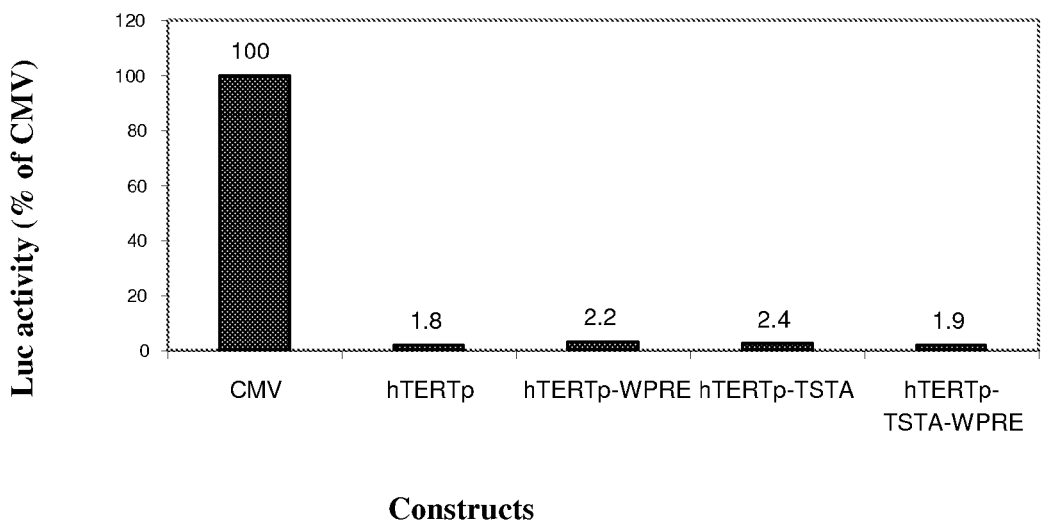

As shown in FIG. 12, the hTERTp is active in both LNCaP cell and PC-3 cells, but its activity was very weak compared to CMV enhancer/promoter. However, WPRE increased the activity by about 2-fold. Surprisingly, TSTA system can boost the activity to 67% of CMV activity in LNCaP cell and 90% in PC-3 cells. For the TSTA system in combination with WPRE, the activity is comparable to CMV in PC-3 and is even 1.5-fold higher in LNCaP cells. In contrast, its activity remains undetectable in WI-38 cells (data not shown).

Figure 13:
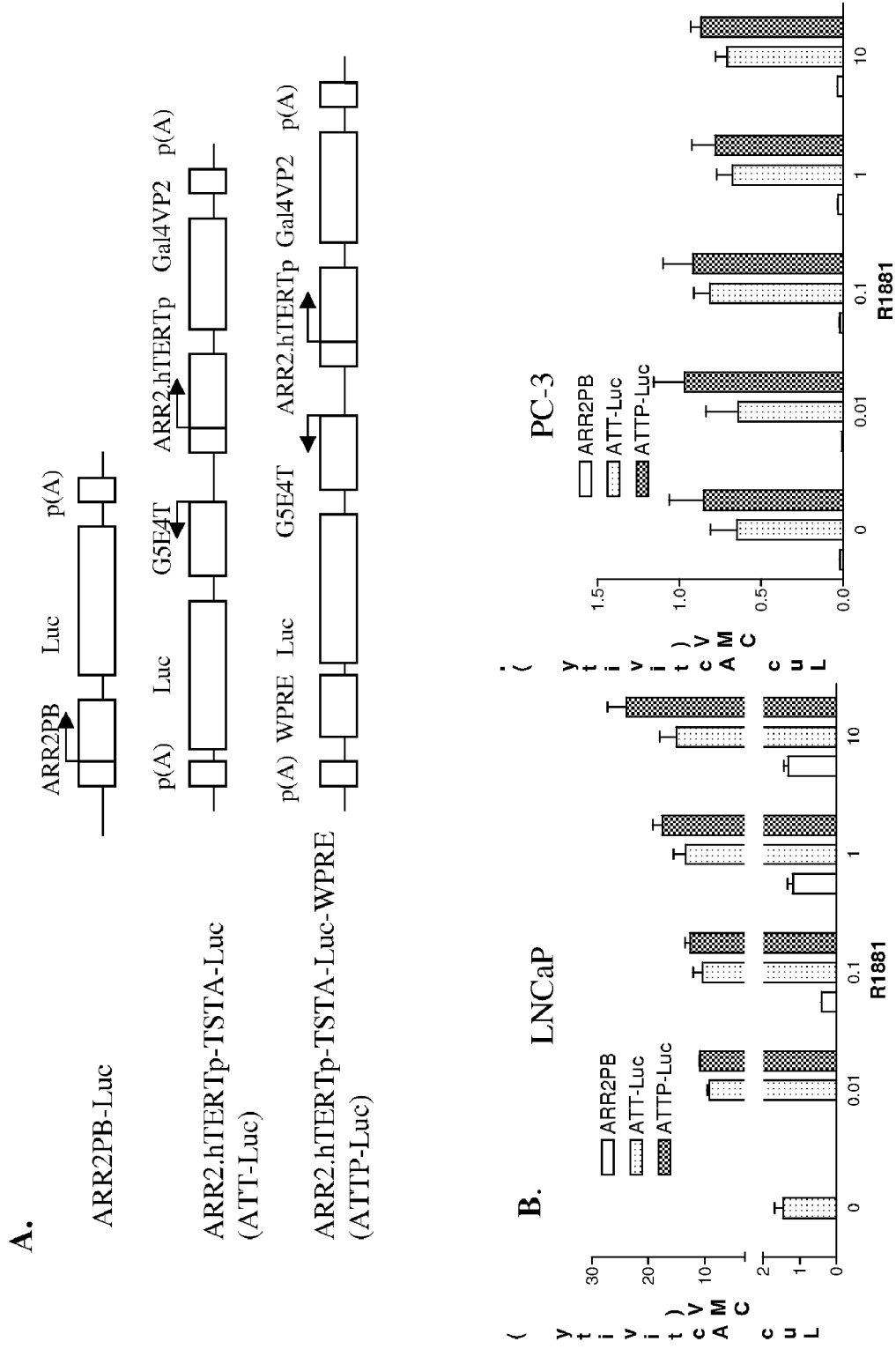
FIG. 13 shows increased activity of androgen-responsive hTERTp-based promoter composites.

In most cases of recurrent prostate cancers, the AR gene is amplified and/or AR is overexpressed (Visakorpi T, Nat Genet 1995 (Chen, Welsbie et al. 2004)). Therefore, it should also greatly improve the effective index if the activity of this system can be stimulated by androgen. To accomplish this goal, the ARR2 element derived from plasmid ARR2PB (Zhang, Thomas et al. 2000; Xie, Zhao et a/2001) was fused to the hTERTp promoter of phTERTp-TSTA-Luc and phTERTp-TSTA-Luc-WPRE, to produce plasmid pARR2.hTERTp-TSTA-Luc and pARR2.hTERTp-TSTA-Luc-WPRE (FIG. 13A). LNCaP cells and PC-3 cells were transiently co-transfected with similar molar quantities of plasmid DNA with the internal control pRL-TK and stimulated with 0.01, 0.1, 1, and 10 nM concentrations of nonmetabolized androgen analog R1881 for two days in medium containing charcoal/dextran-treated FBS. Thereafter, dual luciferase ratio was measured and then compared to CMV activity presented as percentage, as described above. As expected, the activity of ARR2.hTERTp-TSTA and ARR2.hTERTp-TSTA-WPRE composites was increased in an androgen-dependent manner by 10-fold higher than CMV in LNCaP cells, without there being significant change in PC-3 cells.

In further embodiments of the present invention, the respective prostate cancer-specific elements are narrowed further to identify even smaller segments within that retain prostate cancer-specific expression activity. For example, deletion constructs may be made of these respective regions, and their tissue specificity is tested to identify the smaller segments that maintain the ability to direct expression in prostate cancer tissue.

TSTA and WPRE Enhance the Activity of the hTERT Promoter

Figure 22:
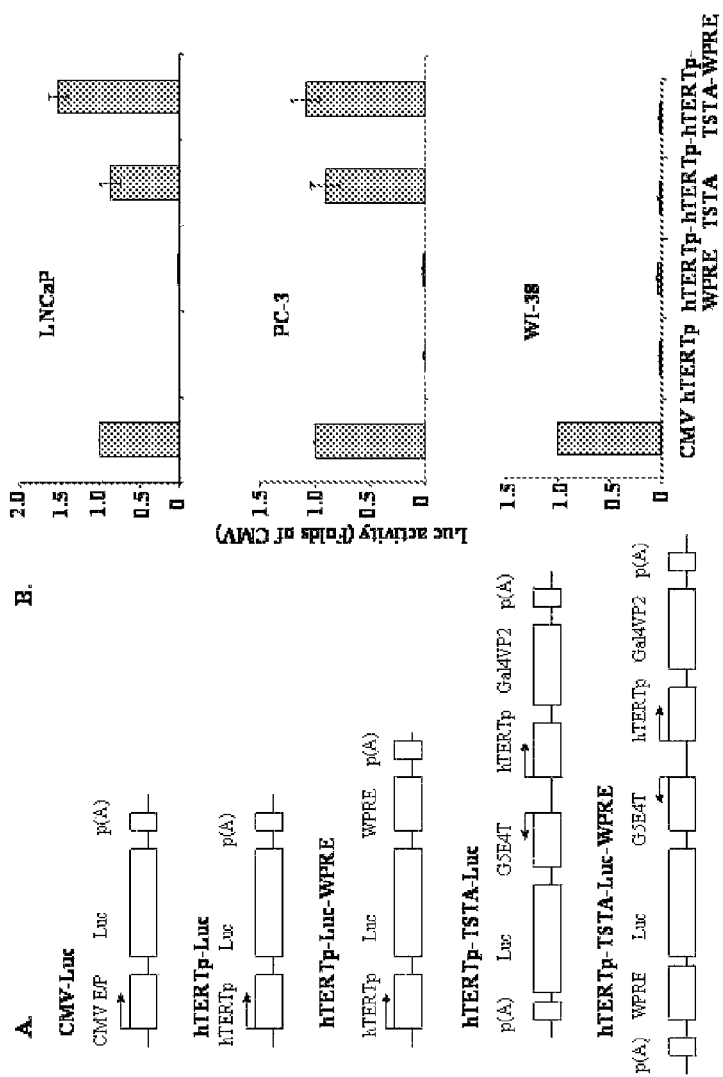
FIG. 22 shows a comparison of firefly luciferase activity under the control of CMV promoter and hTERTp-based promoter composites.

In FIG. 22, there is comparison of firefly luciferase activity under the control of CMV promoter and hTERTp-based promoter composites. FIG. 22A shows a schematic diagram of reporter constructs. FIG. 22B shows that prostate cancer LNCaP and PC-3, and normal human fibroblast WI-38 cells lines were transiently co-transfected with reporter plasmid DNA and the internal control vector pRL-TK. 48 h later, the dual luciferase ratio was measured. Shown are the luciferase activities (folds) in relative to the CMV promoter (setting at 1). The hTERTp activity is increased in both LNCaP and PC-3 cells through the TSTA system, and is further enhanced by WPRE (FIG. 22B). In combination with TSTA and WPRE, the activity of hTERTp-TSTA-WPRE is comparable to or even 1.5-fold greater than that of the CMV promoter, in PC-3 and LNCaP cells, respectively. Importantly, its activity remains silent in human normal lung fibroblast cells WI-38 and in normal tissue of the mouse model further confirmed later.

The cis-acting ARR2 element further boosts the activity of TSTA- and WPRE-modified hTERTp in response to androgen stimulation in vivo. In most cases of recurrent or metastatic prostate cancer through ADPC to AIPC, the AR gene is amplified and/or AR is overexpressed and still able to bind to androgen (or androgen analog) following by binding to the androgen responsive element (ARE), resulting in transcriptional activation (Chen et al., 2004; Visakorpi et al., 1995). In this regard, the therapeutic index should be greatly improved if the promoter contains an ARE, which binds to the androgen (or androgen analog)/AR complexes, leading to stimulation of the therapeutic gene expression.

Figure 23:
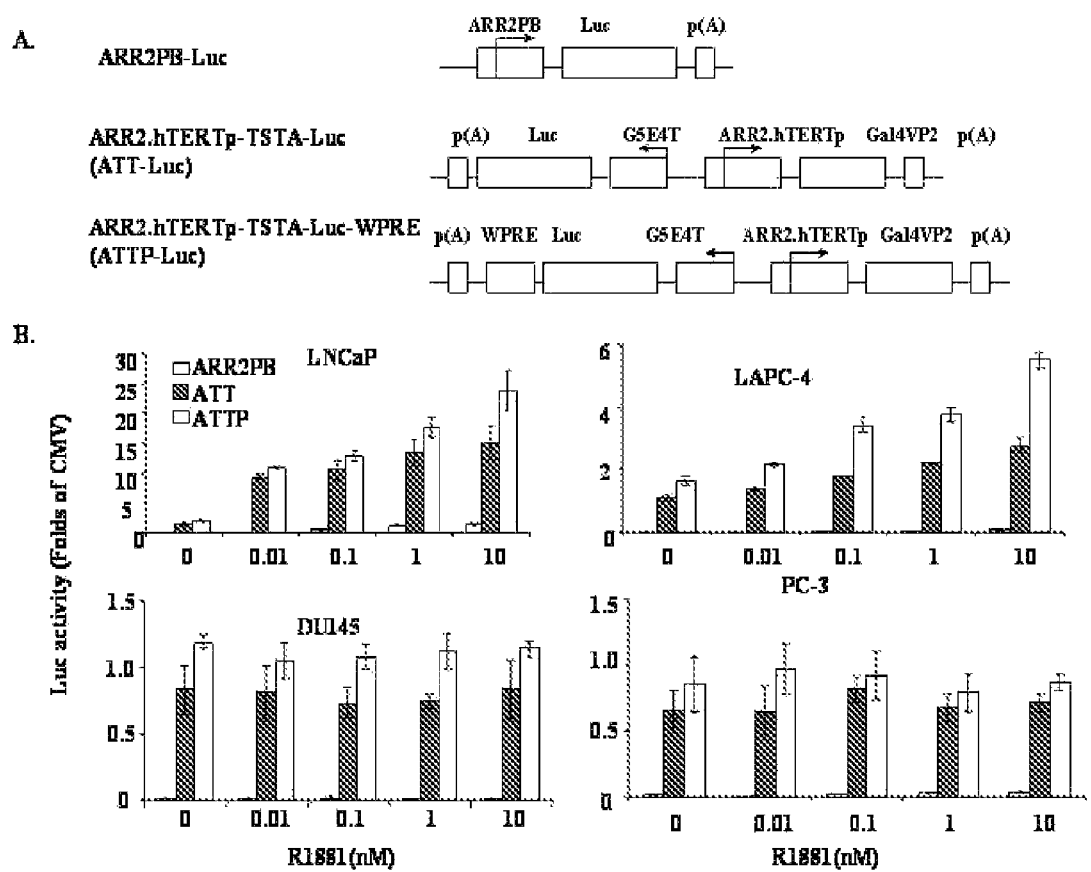
FIG. 23 demonstrates that a cis-acting ARR2 element further boosts TSTA- and/or WPRE modified hTERTp in response to androgen stimulation.

To accomplish this goal, the ARR2 element (androgen-receptor responsive element 2), which is derived from ARR2PB (Xie et al., 2001; Zhang et al., 2000), was fused to upstream of hTERTp in our newly constructed systems, to generate ATT-Luc (pGl3-ARR2.hTERTp-TSTA-Luc) and ATTP-Luc (pGl3-ARR2.hTERTp-TSTA-Luc-WPRE) (FIG. 23A). ARR2PB-Luc (pGl3-ARR2PB-Luc) was used as a control and CMV-Luc as a reference tool. The cells were transiently co-transfected with the constructs and the internal control vector pRL-TK and incubated with increasing concentrations of androgen analog, R1881. Indeed, the activities of ATT and ATTP composites were increased in an androgen-dependent manner, up to 15- and 25-fold greater in AR+ADPC LNCaP cells and up to 2.8- and 5.5-fold in AR+AIPC LAPC-4 cells, respectively, than that of the CMV promoter (FIG. 23B). ARR2 does not interfere with the transcriptional activities of hTERTp-TSTA and hTERTp-TSTA-WPRE in PC-3 and LNCaP cells (FIG. 22B and FIG. 23B), and their specificity in normal cells (data not shown). Compared with ATTP and ATT, ARR2PB is much less active in AR+ (LNCaP and LAPC-4) and almost inactive in AR− (PC-3 and DU145) cells (FIG. 23B). Thus, the newly generated ATTP and ATT are highly active in all four cell lines tested, which activities are comparable in AR− AIPC (PC-3 and DU145) cells to, and much stronger in AR+ ADPC (LNCaP) and AR+ AIPC(LAPC-4) cells than that of the CMV promoter, and importantly remain silent in the normal cells.

Figure 24:
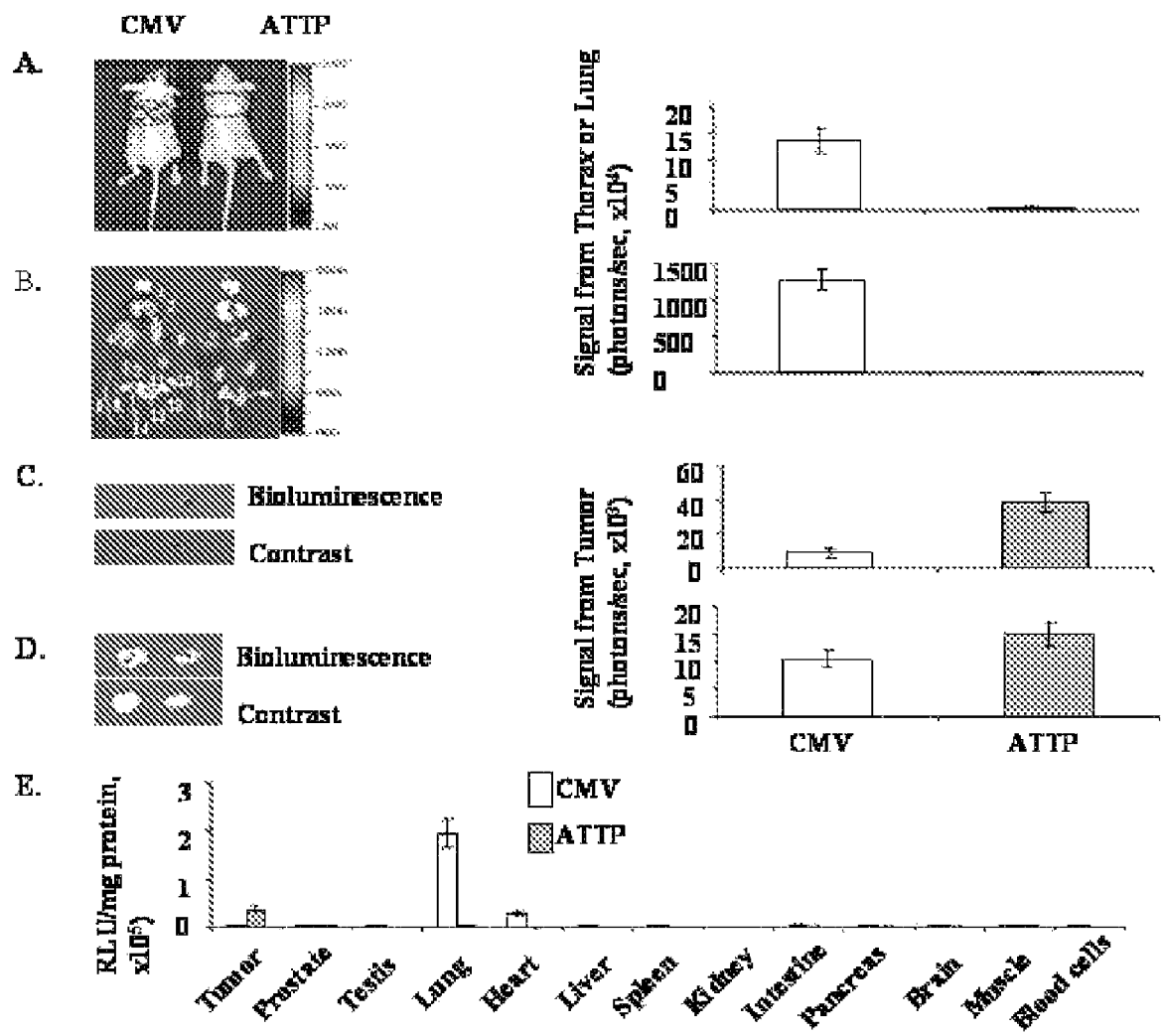
FIG. 24 demonstrates in vivo luciferase expression in LNCaP and PC-3 xenografts after systemic delivery of plasmid DNA. Male nude mice bearing s.c LNCaP tumors were i.v. injected with DNA (CMV-Luc or ATTP-Luc):liposome complexes. Mice were anesthetized, and imaged for 2 min with an IVIS™ imaging system following an i.p. injection of D-luciferin. The imaging shown is 24 h after the last injection.

ATTP is robust in ADPC and AIPC xenografts in vivo. To further determine whether the activity and specificity of ATTP would be maintained in vivo, the present inventors established male BABL/c nu/nu mouse models of s.c. LNCaP and PC-3 xenografts. Mice bearing LNCaP or PC-3 tumors were i.v. injected with 50 μg of pGL3-ATTP-Luc and pGL3-CMV-Luc in DNA:liposome complexes, once a day for three consecutive days. Mice-bearing LNCaP tumors were in vivo imaged with a non-invasive imaging system (Xie et al., 2004) for two minutes every day and sacrificed 24 h after the last injection. Bioluminescent imaging showed very brilliant light spots in the area of the thorax (lung/heart) of mice treated with CMV-Luc, but almost none in the same area of mice treated with ATTP-Luc (FIG. 24A). To further characterize the source of the light, the mice were sacrificed immediately after live imaging, and their major organs were dissected to be imaged ex vivo. The present inventors verified that the strongest photo-emitting organ was the lung of mice treated with CMV-Luc, whereas the signal from the lungs of mice treated with ATTP-Luc was undetectable (FIG. 24B). To increase signal strength by prolonging photon-exciting time, the dissected tumors were then immediately imaged for 10 min. The tumors from mice treated with ATTP-Luc produced much stronger signal than ones from mice treated with CMV-Luc (P, 0.002) (FIG. 24C). Consistent with the in vivo and ex vivo imaging results, the luciferase activities from lungs and hearts of mice treated with CMV-Luc were significantly greater than that of mice treated with ATTP-Luc. In contrast, the luciferase activity from tumors of mice treated with ATTP-Luc was 14.5-fold greater than that of the tumors of mice with CMV-Luc (P, 0.004) (FIG. 24E). The cancer-specific index (the luciferase activity of tumors to lung) (Chen et al., 2004) was 14.3 for ATTP-Luc in contrast to 0.012 for CMV-Luc in the LNCaP tumor model. Due to the fact that PC-3 cells are AR− the signal from PC-3 tumors treated with ATTP-Luc was not as great as that from LNCaP tumors. However, the signal from the PC-3 tumors of mice treated with ATTP-Luc was still stronger than that of mice treated with CMV-Luc (FIG. 24D) and the cancer-specific index (3.9) of ATTP-Luc is still much better that that (0.015) of CMV-Luc (data not shown). Taken together, the "chimeric" ATTP is able to direct a gene of interest to the prostate tumor (both AR+ and AR−) at least as efficiently as that of the CMV promoter in the AR− prostate cancer, and much more efficiently in AR+ prostate cancer whereas there is almost no expression in normal cells.

Example 4

In Vitro Testing of Cancer-Specific Promoters

A construct(s) comprising the inventive promoters operably linked to a respective therapeutic polynucleotide are tested in vitro. For example, the control sequences are selected, in some embodiments based on previously generated data suggesting the sequence is effective in a desired tissue or cell. In other embodiments, control sequences are selected without prior knowledge of potential effectiveness. The control sequence to be tested is operably linked to a reporter sequence, such as one whose expression and/or gene product may be monitored, including by color, light, or fluorescence, for example. Examples of reporter genes include luciferase or β-galactosidase. Additional control sequences of any kind may also be added to the construct, including transcriptional or post-transcriptional control sequences, minimal promoters, and so forth. The construct to be tested and its one or more appropriate controls are then introduced into a desired cell and assayed for expression. In particular embodiments, the construct to be tested generates expression at such levels as determined by the skilled artisan to be effective in the desired cell or tissue in which it resides.

Example 5

In Vivo Testing of Cancer-Specific Promoters

A construct(s) comprising the inventive promoters operably linked to a respective therapeutic polynucleotide as it relates to its anti-tumor activity is tested in an animal study. The construct is delivered by a vector, such as in a liposome or on a plasmid or viral vector, into nude mice models to test for its anti-tumor activity. Once the anti-tumor activity is demonstrated, potential toxicity is further examined using immunocompetent mice, followed by clinical trials.

In a specific embodiment, the preferential growth inhibitory activity of a construct comprising the inventive promoter operably linked to a therapeutic polynucleotide is tested in an animal. Briefly, and by example only, HER-2/neu overexpressing breast cancer cell lines (such as SKBR3 and MDA-MB361) are administered into mammary fat-pad of nude mice to generate a breast xenografted model. After the tumors reach a particular size, the construct of the present invention or its control is intravenously injected into the mouse in an admixture with an acceptable carrier, such as liposomes. The tumor sizes and survival curve from these treatments are compared and statistically analyzed. In a preferred embodiment, the constructs comprising the promoters of the invention preferentially inhibit the growth of a tumor tissue-specifically compared to that of wild-type p21.

Example 6

Clinical Testing with Cancer-Specific Promoters

This example is concerned with the development of human treatment protocols using constructs comprising the cancer-specific promoters of the invention alone or in combination with other anti-cancer drugs. The anti-cancer drug treatment using constructs comprising the cancer-specific promoters of the invention will be of use in the clinical treatment of various cancers. Such treatment will be particularly useful tools in anti-tumor therapy, for example, in treating patients with the respective breast, prostate, and pancreatic cancers, such as those that are resistant to conventional chemotherapeutic regimens.

The various elements of conducting a clinical trial, including patient treatment and monitoring, will be known to those of skill in the art in light of the present disclosure. The following information is being presented as a general guideline for use in establishing the constructs comprising the cancer-specific promoters of the invention in clinical trials.

Patients with advanced, metastatic breast, prostate, or pancreatic cancers chosen for clinical study will typically be at high risk for developing the cancer, will have been treated previously for the cancer which is presently in remission, or will have failed to respond to at least one course of conventional therapy. In an exemplary clinical protocol, patients may undergo placement of a Tenckhoff catheter, or other suitable device, in the pleural or peritoneal cavity and undergo serial sampling of pleural/peritoneal effusion. Typically, one will wish to determine the absence of known loculation of the pleural or peritoneal cavity, creatinine levels that are below 2 mg/dl, and bilirubin levels that are below 2 mg/dl. The patient should exhibit a normal coagulation profile.

In regard to the constructs comprising the cancer-specific promoters of the invention and other anti-cancer drug administration, a Tenckhoff catheter, or alternative device may be placed in the pleural cavity or in the peritoneal cavity, unless such a device is already in place from prior surgery. A sample of pleural or peritoneal fluid can be obtained, so that baseline cellularity, cytology, LDH, and appropriate markers in the fluid (CEA, CA15-3, CA 125, PSA, p38 (phosphorylated and un-phosphorylated forms), Akt (phosphorylated and un-phosphorylated forms) and in the cells (constructs comprising the cancer-specific promoters of the invention) may be assessed and recorded.

In the same procedure, the constructs comprising the cancer-specific promoters of the invention may be administered alone or in combination with the other anti-cancer drug. The administration may be in the pleural/peritoneal cavity, directly into the tumor, or in a systemic manner, for example. The starting dose may be about 0.05 mg/kg body weight. Three patients may be treated at each dose level in the absence of grade >3 toxicity. Dose escalation may be done by 100% increments (0.5 mg, 1 mg, 2 mg, 4 mg) until drug related grade 2 toxicity is detected. Thereafter dose escalation may proceed by 25% increments. The administered dose may be fractionated equally into two infusions, separated by six hours if the combined endotoxin levels determined for the lot of the constructs comprising the cancer-specific promoters of the invention, and the lot of anti-cancer drug exceed 5 EU/kg for any given patient.

The constructs comprising the cancer-specific promoters of the invention and/or the other anti-cancer drug combination, may be administered over a short infusion time or at a steady rate of infusion over a 7 to 21 day period. The constructs comprising the cancer-specific promoters of the invention infusion may be administered alone or in combination with the anti-cancer drug. The infusion given at any dose level will be dependent upon the toxicity achieved after each. Hence, if Grade II toxicity was reached after any single infusion, or at a particular period of time for a steady rate infusion, further doses should be withheld or the steady rate infusion stopped unless toxicity improved. Increasing doses of the constructs comprising the cancer-specific promoters of the invention, in combination with an anti-cancer drug will be administered to groups of patients until approximately 60% of patients show unacceptable Grade III or IV toxicity in any category. Doses that are ⅔ of this value could be defined as the safe dose.

Physical examination, tumor measurements, and laboratory tests should, of course, be performed before treatment and at intervals of about 3-4 weeks later. Laboratory studies should include CBC, differential and platelet count, urinalysis, SMA-12-100 (liver and renal function tests), coagulation profile, and any other appropriate chemistry studies to determine the extent of disease, or determine the cause of existing symptoms. Also appropriate biological markers in serum should be monitored e.g. CEA, CA 15-3, p38 (phosphorylated and non-phosphorylated forms) and Akt (phosphorylated and non-phosphorylated forms), p185, etc.

To monitor disease course and evaluate the anti-tumor responses, it is contemplated that the patients should be examined for appropriate tumor markers every 4 weeks, if initially abnormal, with twice weekly CBC, differential and platelet count for the 4 weeks; then, if no myelosuppression has been observed, weekly. If any patient has prolonged myelosuppression, a bone marrow examination is advised to rule out the possibility of tumor invasion of the marrow as the cause of pancytopenia. Coagulation profile shall be obtained every 4 weeks. An SMA-12-100 shall be performed weekly. Pleural/peritoneal effusion may be sampled 72 hours after the first dose, weekly thereafter for the first two courses, then every 4 weeks until progression or off study. Cellularity, cytology, LDH, and appropriate markers in the fluid (CEA, CA15-3, CA 125, ki67 and Tunel assay to measure apoptosis, Akt) and in the cells (Akt) may be assessed. When measurable disease is present, tumor measurements are to be recorded every 4 weeks. Appropriate radiological studies should be repeated every 8 weeks to evaluate tumor response. Spirometry and DLCO may be repeated 4 and 8 weeks after initiation of therapy and at the time study participation ends. An urinalysis may be performed every 4 weeks.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least 1 month with no tumor sites showing enlargement. Similarly, a mixed response may be defined by a reduction of the product of perpendicular diameters of all measurable lesions by 50% or greater with progression in one or more sites.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

PATENTS

U.S. Pat. No. 4,683,202
U.S. Pat. No. 4,797,368
U.S. Pat. No. 4,879,236
U.S. Pat. No. 5,139,941
U.S. Pat. No. 5,220,007
U.S. Pat. No. 5,284,760
U.S. Pat. No. 5,354,670
U.S. Pat. No. 5,366,878
U.S. Pat. No. 5,389,514
U.S. Pat. No. 5,635,377
U.S. Pat. No. 5,641,484
U.S. Pat. No. 5,670,488
U.S. Pat. No. 5,789,166
U.S. Pat. No. 5,798,208
U.S. Pat. No. 5,830,650
U.S. Pat. No. 5,871,986
U.S. Pat. No. 5,925,565
U.S. Pat. No. 5,928,906
U.S. Pat. No. 5,935,819

PUBLICATIONS

Adachi, N., Nomoto, M., Kohno, K. & Koyama, H. (2000). Gene, 245, 49-57.

Anderson, L. M., Krotz, S., Weitzman, S. A., and Thimmapaya, B. (2000). Breast cancer-specific expression of the Candida albicans cytosine deaminase gene using a transcriptional targeting approach. Cancer Gene Ther 7, 845-852.

Barron, L. G., Szoka Jr., F. C. (1999). Non-viral vectors for gene therapy. Huang, L., Hung, M.-C., Wagner, E. (ed.). Academic Press: San Diego, Calif., pp 229-266.

Bartke, T., Siegmund, D., Peters, N., Reichwein, M., Henkler, F., Scheurich, P., and Wajant, H. p53 upregulates cFLIP, inhibits transcription of NF-kappaB-regulated genes and induces caspase-8-independent cell death in DLD-1 cells, Oncogene. 20: 571-80, 2001.

Boyd, J. M., Gallo, G. J., Elangovan, B., Houghton, A. B., Malstrom, S., Avery, B. J., Ebb, R. G., Subramanian, T., Chittenden, T., Lutz, R. J., and et al. Bik, a novel death-inducing protein shares a distinct sequence motif with Bcl-2 family proteins and interacts with viral and cellular survival-promoting proteins, Oncogene. 11: 1921-8, 1995.

Chen, C. D., D. S. Welsbie, C. Tran, S. H. Back, R. Chen, R. Vessella, M. G. Rosenfeld, and C. L. Sawyers, Molecular determinants of resistance to antiandrogen therapy. Nat Med, 2004. 10(1): p. 33-39.

Chen, J. S., J. C. Liu, L. Shen, K. M. Rau, H. P. Kuo, Y. M. Li, D. Shi, Y. C. Lee, K. J. Chang, and M. C. Hung, Cancer-specific activation of the surviving promoter and its potential use in gene therapy. Cancer Gene Ther, 2004.

Daniel, P. T., Pun, K. T., Ritschel, S., Sturm, I., Holler, J., Dorken, B., and Brown, R. Expression of the death gene Bik/Nbk promotes sensitivity to drug-induced apoptosis in corticosteroid-resistant T-cell lymphoma and prevents tumor growth in severe combined immunodeficient mice, Blood. 94: 1100-7, 1999.

Desagher, S., Osen-Sand, A., Montessuit, S., Magnenat, E., Vilbois, F., Hochmann, A., Journot, L., Antonsson, B., and Martinou, J. C. Phosphorylation of bid by casein kinases I and II regulates its cleavage by caspase 8, Mol. Cell. 8: 601-11, 2001.

Emami, K. H. and Carey, M. (1992) A synergistic increase in potency of a multimerized VP16 transcriptional activation domain. EMBO J. 11:5005-5012.

Fuernkranz, H. A., Schwob, J. E., and Lucas, J. J. (1991) Differential issue localization of oviduct and erythroid transferrin receptors. Proc. Natl. Acad. Sci. USA 88:7505-7508.

Han, J., Sabbatini, P., and White, E. Induction of apoptosis by human Nbk/Bik, a BH3-containing protein that interacts with E1B 19K, Mol Cell Biol. 16: 5857-64, 1996.

Hochhauser, D., Stanway, C. A., Harris, A. L., Hickson, I. D. (1992) Cloning and characterization of the 5' flanking region of the human topoisomerase II alpha gene. J. Biol. Chem. 267(26): 18961-5.

Iyer, M., Wu, L., Carey, M., Wang, Y., Smallwood, A., and Gambhir, S. S. (2001). Two-step transcriptional amplification as a method for imaging reporter gene expression using weak promoters. Proc. Natl. Acad. Sci. 98:14595-14600.

Katabi, M. M., Chan, H. L., Karp, S. E., and Batist, G. (1999). Hexokinase type II: a novel tumor-specific promoter for gene-targeted therapy differentially expressed and regulated in human cancer cells. Hum Gene Ther 10, 155-164.

Klumpp, S. and Krieglstein, J. Serine/threonine protein phosphatases in apoptosis, Curr Opin Pharmacol. 2: 458-62, 2002.

Li, S., Rizzo, M. A., Bhattacharya, S. & Huang, L. (1998). Gene Ther, 5, 930-7.

Li, Y. M., Wen, Y., Zhou, B. P., Kuo, H. P., Ding, Q. & Hung, M. C. (2003). Cancer Res, 63, 7630-3.

Lu, H., Zhang, Y., Roberts, D. D., Osborne, C. K., and Templeton, N. S. (2002). Enhanced gene expression in breast cancer cells in vitro and tumors in vivo. Mol Ther 6, 783-792.

Maeda, T., J, O. W., Matsubara, H., Asano, T., Ochiai, T., Sakiyama, S., and Tagawa, M. (2001). A minimum c-erbB-2 promoter-mediated expression of herpes simplex virus thymidine kinase gene confers selective cytotoxicity of human breast cancer cells to ganciclovir. Cancer Gene Ther 8, 890-896.

Mathai, J. P., Germain, M., Marcellus, R. C., and Shore, G. C. Induction and endoplasmic reticulum location of BIK/NBK in response to apoptotic signaling by E1A and p53, Oncogene. 21: 2534-44, 2002.

Mo, Y. Y., Ameiss, K. A., and Beck, W. T. (1998) Overexpression of human DNA topoisomerase II alpha by fusion to enhanced green fluorescent protein. Biotechn. 25(6):1052-7.

Nettelbeck, D. M., Jerome, V. and Muller, R. (2000) Gene therapy: designer promoters for tumour targeting. Trends Genet. 16:174-181.

Panaretakis, T., Pokrovskaja, K., Shoshan, M. C., and Grander, D. Activation of Bak, Bax, and BH3-only Proteins in the Apoptotic Response to Doxorubicin, J Biol Chem. 277: 44317-26, 2002.

Puthalakath, H. and Strasser, A. Keeping killers on a tight leash: transcriptional and post-translational control of the pro-apoptotic activity of BH3-only proteins, Cell Death Differ. 9: 505-12, 2002.

Qiao, J., Doubrovin, M., Sauter, B. V., Huang, Y., Guo, Z. S., Balatoni, J., Akhurst, T., Blasberg, R. G., Tjuvajev, J. G., Chen, S. H., and Woo, S. L. (2002). Tumor-specific transcriptional targeting of suicide gene therapy. Gene Ther 9, 168-175.

Sadowski I, Ma J, Triezenberg S, Ptashne M. GAL4-VP16 is an unusually potent transcriptional activator. Nature. 1988 Oct. 6; 335(6190):563-4.

Sato, M., Johnson, M., Zhang, L., Zhang, B., Le, K., Gambhir, S. S., Carey, M., Wu, L. (2003) Optimization of adenoviral vectors to direct highly amplified prostate-specific expression for imaging and gene therapy. Mol. Ther. 8(5): 726-737.

Shindelman, J. E., Ortmeyer, a. E., and Sussman, H. H. (1981) Demonstration of the Transferrin Receptor in human breast cancer tissue. Potential marker for identifying dividing cells. Int. J. Cancer 27:329-334.

Shterman, N., Kupfer, B., and Moroz, C. (1991) Comparison of Transferrin Receptors, Iron Content and Isoferritin profile in normal and malignant human breast cell lines. Pathobiol. 59:19-25.

Templeton, N. S., Lasic, D. D., Frederik, P. M., Strey, H. H., Roberts, D. D. & Pavlakis, G. N. (1997). Nat Biotechnol, 15, 647-52.

Theodorakis, P., Lomonosova, E., and Chinnadurai, G. Critical requirement of BAX for manifestation of apoptosis induced by multiple stimuli in human epithelial cancer cells, Cancer Res. 62: 3373-6, 2002.

Verma, S., Zhao, L., and Chinnadurai, G. Phosphorylation of the Pro-Apoptotic Protein BIK: Mapping of Phosphorylation sites and Effect on Apoptosis, J Biol. Chem. 17: 17, 2000.

Visakorpi, T., E. Hyytinen, P. Koivisto, M. Tanner, R. Keinanen, C. Palmberg, A. Palotie, T. Tammela, J. Isola, and O. P. Kallioniemi, In vivo amplification of the androgen receptor gene and progression of human prostate cancer. Nat Genet, 1995. 9(4): p. 401-6.

Wang, H. G., Pathan, N., Ethell, I. M., Krajewski, S., Yamaguchi, Y., Shibasaki, F., McKeon, F., Bobo, T., Franke, T. F., and Reed, J. C. Ca2+-induced apoptosis through calcineurin dephosphorylation of BAD, Science. 284: 339-43, 1999.

Xie X, Luo Z, Slawin K M, Spencer D M. The EZC-prostate model: noninvasive prostate imaging in living mice. Mol. Endocrinol. 2004 March; 18(3):722-32.

Xie, X., X. Zhao, Y. Liu, J. Zhang, R. J. Matusik, K. M. Slawin, and D. M. Spencer, Adenovirus-mediated tissue-targeted expression of a caspase-9-based artificial death switch for the treatment of prostate cancer. Cancer Res, 2001. 61(18): p. 6795-804.

Zhang, L., Adams, J. Y., Billick, E., Ilagan, R., Iyer, M., Le, K., Smallwood, A., Gambhir, S. S., Carey, M., Wu, L. (2002) Molecular engineering of a two-step transcription amplification (TSTA) system for transgene delivery in prostate cancer. Mol. Ther. 5(3): 223-232.

Zhang, J., T. Z. Thomas, S. Kasper, and R. J. Matusik, A small composite probasin promoter confers high levels of prostate-specific gene expression through regulation by androgens and glucocorticoids in vitro and in vivo. Endocrinology, 2000. 141(12): p. 4698-710.

Zou, Y., Peng, H., Zhou, B., Wen, Y., Wang, S. C., Tsai, E. M., and Hung, M. C. Systemic tumor suppression by the proapoptotic gene bik, Cancer Res. 62: 8-12, 2002.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. A polynucleotide construct comprising a prostate cancer-specific control sequence, said control sequence comprising at least two of the following sequences:
   a prostate tissue-specific control sequence;
   a cancer-specific control sequence; and
   a two-step transcriptional amplification (TSTA) sequence, said TSTA sequence including a DNA binding domain and an activation domain, wherein said prostate tissue-specific control sequence comprises SEQ ID NO:17.

2. A polynucleotide construct comprising a prostate cancer-specific control sequence, said control sequence comprising at least two of the following sequences:
   a prostate tissue-specific control sequence;
   a cancer-specific control sequence; and
   a two-step transcriptional amplification (TSTA) sequence, said TSTA sequence including a DNA binding domain and an activation domain, wherein said prostate tissue-specific control sequence comprises SEQ ID NO:17 and wherein said cancer tissue-specific control sequence comprises SEQ ID NO:18.

3. A polynucleotide construct comprising a prostate cancer-specific control sequence, said control sequence comprising at least two of the following sequences:
   a prostate tissue-specific control sequence;
   a cancer-specific control sequence; and
   a two-step transcriptional amplification (TSTA) sequence, said TSTA sequence including a DNA binding domain and an activation domain, wherein said cancer tissue-specific control sequence comprises SEQ ID NO:18.

4. The construct of claim 1, wherein the DNA binding domain is Gal1, Gal4, or LexA.

5. The construct of claim 1, wherein the activation domain is VP2 or VP16.

6. The construct of claim 1, wherein the TSTA sequence is GAL4-VP2 or GAL4-VP16.

7. The construct of claim 1, wherein said control sequence is operably linked to a polynucleotide encoding a therapeutic gene product.

8. The construct of claim 7, wherein the therapeutic gene product is an inhibitor of cell proliferation, a regulator of programmed cell death, or a tumor suppressor.

9. The construct of claim 1, further defined as being comprised in a liposome.

10. A polynucleotide construct of any one of claim 1, 2 or 3 further comprising a post transcriptional regulatory sequence.

11. The construct of claim 10, wherein the post-transcriptional regulatory sequence is a woodchuck hepatitis virus post-transcriptional regulatory element (WPRE) sequence.

\* \* \* \* \*